United States Patent
Baker

(10) Patent No.: US 9,956,274 B2
(45) Date of Patent: *May 1, 2018

(54) METHOD TO GENERATE ANTIBODIES TO ION CHANNELS

(71) Applicant: UCB Biopharma SPRL, Brussels (BE)

(72) Inventor: Terence Seward Baker, Wraysbury (GB)

(73) Assignee: UCB Biopharma SPRL, Brussels (BE)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/991,048

(22) Filed: Jan. 8, 2016

(65) Prior Publication Data

US 2016/0193309 A1 Jul. 7, 2016

Related U.S. Application Data

(63) Continuation of application No. 13/523,104, filed on Jun. 14, 2012, now Pat. No. 9,234,037, which is a continuation of application No. 13/504,259, filed as application No. PCT/EP2010/066279 on Oct. 27, 2010, now Pat. No. 9,067,995.

(60) Provisional application No. 61/255,202, filed on Oct. 27, 2009.

(30) Foreign Application Priority Data

Dec. 22, 2009 (GB) .................................. 0922435.3

(51) Int. Cl.
| | | |
|---|---|---|
| C12N 5/07 | (2010.01) |
| A61K 39/395 | (2006.01) |
| A61K 39/00 | (2006.01) |
| A61K 38/12 | (2006.01) |
| C07K 16/00 | (2006.01) |
| C07K 14/705 | (2006.01) |
| C07K 16/28 | (2006.01) |

(52) U.S. Cl.
CPC ........ *A61K 39/0005* (2013.01); *C07K 14/705* (2013.01); *C07K 16/28* (2013.01); *A61K 2039/545* (2013.01); *A61K 2039/6081* (2013.01); *A61K 2039/62* (2013.01); *C07K 2317/14* (2013.01); *C07K 2317/20* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,741,900 A | 5/1988 | Alvarez |
| 4,816,397 A | 3/1989 | Boss |
| 5,219,996 A | 6/1993 | Bodmer |
| 5,223,409 A | 6/1993 | Ladner |
| 5,403,484 A | 4/1995 | Ladner |
| 5,427,908 A | 6/1995 | Dower |
| 5,516,637 A | 5/1996 | Huang |
| 5,545,806 A | 8/1996 | Lonberg |
| 5,569,825 A | 10/1996 | Lonberg |
| 5,571,698 A | 11/1996 | Ladner |
| 5,580,717 A | 12/1996 | Dower |
| 5,585,089 A | 12/1996 | Queen |
| 5,625,126 A | 4/1997 | Lonberg |
| 5,633,425 A | 5/1997 | Lonberg |
| 5,658,727 A | 8/1997 | Barbas |
| 5,661,016 A | 8/1997 | Lonberg |
| 5,677,425 A | 10/1997 | Bodmer |
| 5,698,426 A | 12/1997 | Huse |
| 5,733,743 A | 3/1998 | Johnson |
| 5,750,753 A | 5/1998 | Kimae |
| 5,770,429 A | 6/1998 | Lonberg |
| 5,780,225 A | 7/1998 | Wigler |
| 5,821,047 A | 10/1998 | Garrard |
| 5,969,108 A | 10/1999 | McCafferty |
| 6,331,415 B1 | 12/2001 | Cabilly |
| 7,456,187 B2 | 11/2008 | Ford |
| 7,521,541 B2 | 4/2009 | Eigenbrot |
| 7,670,771 B2 | 3/2010 | Leppert |
| 8,734,798 B2 | 5/2014 | Finney |
| 8,926,977 B2 | 1/2015 | Miller |
| 8,986,954 B2 | 3/2015 | Finney |
| 9,067,995 B2 | 6/2015 | Baker |
| 9,234,037 B2 | 1/2016 | Baker |
| 9,266,953 B2 | 2/2016 | Finney |
| 2003/0194751 A1 | 10/2003 | Dubin |
| 2004/0191265 A1 | 9/2004 | Schenerman |
| 2007/0041972 A1 | 2/2007 | Rother |

(Continued)

FOREIGN PATENT DOCUMENTS

| | | |
|---|---|---|
| EP | 0438474 B1 | 5/1996 |
| EP | 0463151 B1 | 6/1996 |

(Continued)

OTHER PUBLICATIONS

Li et al. Cyclization strategies in peptide derived drug design. Current Topics in Medicinal Chemistry. 2:325-341, 2002.*
Chioni et al. A novel polyclonal antibody specific for the Nav1.5 voltage-gated Na+ channel 'neonatal' splice form. Journal of Neuroscience Methods. 147:88-98, 2005.*
Bekele-Acuri et al. Generation and characterization of subtype-specific monoclonal antibodies to K+ channel alpha- and beta-subunit polypeptides. Neuropharmacology. 35(7):851-865, 1996.*
Schulz-Utermoehl et al. Affinity and Potency of Proinhibitory Antipeptide Antibodies Against CYP2D6 is Enhanced Using Cyclic Peptides as Immunogens. Drug Metabolism and Disposition, 2000; 28(5):544-551.*

(Continued)

*Primary Examiner* — Vanessa L. Ford
*Assistant Examiner* — Sandra E Dillahunt
(74) *Attorney, Agent, or Firm* — Saul Ewing Arnstein & Lehr, LLP

(57) ABSTRACT

The present invention provides a method for generating a functionally modifying antibody to an ion channel comprising immunizing a host with a cyclic peptide comprising at least part of an extracellular sequence of said ion channel.

19 Claims, 24 Drawing Sheets

(56) References Cited

U.S. PATENT DOCUMENTS

| | | |
|---|---|---|
| 2009/0053227 A1 | 2/2009 | Gately |
| 2011/0135662 A1 | 6/2011 | Finney |
| 2012/0259096 A1 | 10/2012 | Miller |
| 2012/0263727 A1 | 10/2012 | Baker |
| 2012/0263728 A1 | 10/2012 | Baker |
| 2014/0342406 A1 | 11/2014 | Finney |
| 2015/0203571 A1 | 7/2015 | Miller |
| 2015/0232553 A1 | 8/2015 | Finney |

FOREIGN PATENT DOCUMENTS

| | | |
|---|---|---|
| EP | 0546073 B1 | 9/1997 |
| EP | 0996622 B1 | 10/2002 |
| WO | 9002809 A1 | 3/1990 |
| WO | 9109967 A1 | 7/1991 |
| WO | 9110737 A1 | 7/1991 |
| WO | 9201047 A1 | 1/1992 |
| WO | 9202551 A1 | 2/1992 |
| WO | 9218619 A1 | 10/1992 |
| WO | 9222583 A2 | 12/1992 |
| WO | 9311236 A1 | 6/1993 |
| WO | 9515982 A2 | 6/1995 |
| WO | 9520401 A1 | 8/1995 |
| WO | 9749805 A2 | 12/1997 |
| WO | 9820734 A1 | 5/1998 |
| WO | 9825971 A1 | 6/1998 |
| WO | 9903859 A1 | 1/1999 |
| WO | 0062800 | 10/2000 |
| WO | 03048208 A2 | 6/2003 |
| WO | 03050531 A2 | 6/2003 |
| WO | 2004051268 A1 | 6/2004 |
| WO | 2004106377 A1 | 12/2004 |
| WO | 2005003169 A2 | 1/2005 |
| WO | 2005003170 A2 | 1/2005 |
| WO | 2005003171 A2 | 1/2005 |
| WO | 2005113605 A1 | 12/2005 |
| WO | 2005117984 A2 | 12/2005 |
| WO | 2007023298 | 3/2007 |
| WO | 2007041972 A1 | 4/2007 |
| WO | 2007109324 A2 | 9/2007 |
| WO | 2008038024 A1 | 4/2008 |
| WO | 2008090958 A1 | 7/2008 |
| WO | 2009033027 A2 | 3/2009 |
| WO | 2010035012 A1 | 4/2010 |

OTHER PUBLICATIONS

Saito et al. Sodium channel mutatiuon in irritable bowel syndrome:evidence for an ion channel. American Journal of Gastrointestinal Liver Physiology, 2008;296:211-218.*

Vajdos et al. Comprehensive Functional Maps of the Antigenbinding Site of an Anti-ErbB2 Antibody Obtained with Shotgun Scanning Mutagenesis. J Mol Biol. Jul. 5, 2002;320(2):415-28.*

Brown et al. Tolerance to Single, but Not Multiple, Amino Acid Replacements in Antibody V, CDR2. J Immunol. May 1996;156(9):3285-91.*

Black et al. Expression of Nav1.7 in DRG neurons extends from peripheral terminals in the skin to central preterminal banches and terminals in the dorsal horn. Mol. Pain. 8:82; 2012.*

Saito et al. American Journal of Physiology Gastrointestinal and Liver Physiology. 296(2):G211-18, published online Dec. 4, 2008.*

Adair, J,R., et al., "Therapeutic antibodies," Drug Design Reviews—Online, 2005, vol. 2, No. 3, pp. 209-217.

Alonso, A., et al., 'Subthreshold Na1-dependent theta-like rhythmicity in stellate cells of entorhinal cortex layer II', Nature, vol. 342, pp. 175-177, 1989.

Ames, R.S., et al., "Conversion of Murine Fobs Isolated from a Combinatorial Phage Display Library to Full Length Immunoglobulins," J. Immunol. Methods, vol. 184, No, 2, pp. 177-186, 1995.

Angal, S., et al. "A single amino acid substitution abolishes the heterogeneity of chimeric mouse/human (IgG4) antibody", Molecular Immunology, vol. 30, No. 1, pp. 105-108, 1993.

Anger, T., et al., 'Medicinal Chemistry of Neuronal Voltage-Gated Sodium Channel Blockers', J. Med. Chem., vol. 44, No. 2, pp. 115-137, 2001.

Babcook, J., et al., "A novel strategy for generating monoclonal antibodies from single, isolated lymphocytes producing antibodies of defined specificities," Proc. Natl. Acad. Sci. USA, vol. 93, No. 15, pp. 7843-7848, 1996.

Barlos; K., et al., 'Solid phase synthesis of partially protected and free peptides containing disulphide bonds by simultaneous cysteine oxidation-release from 2-chlorotrityl resin', International Journal of Peptide and Protein Res., vol. 38, No. 6, pp. 562-568, 1991.

Benes, J., et al.,'Anticonvuisant and Sodium Channel-Blocking Properties of Novel 10,11-Dihydro-5H-dibenz[b,t]azepine-5-carboxamide Derivatives,' J. Med. Chem., vol. 42, pp. 2582-2587, 1999.

Benham, Christopher D., "Simple Recipe for Blocking Ion Channels," Nature Biotechnology, 2005, vol. 23, No. 1, pp. 1234-1235.

Bird, R.E., et al., "Single-chain antigen-binding proteins," Science, vol. 242, No. 4877, pp. 423-426, 1988.

Black, J.A. et al., 'Multiple Sodium Channel Isoforms and Mitogen-Activated Protein Kinases are Present in Painful Human Neuromas,' Annals of Neurology, vol. 64, No, 6, pp. 644-653, 2008.

Black, J.A., et al., 'Expression of Nav1.7 in DRG Neurons Extends from Peripheral Terminals in the Skin to Central Preterminal Branches and Terminals in the Dorsal Horn,' Molecular Pain, vol. 3, No. 82, pp. 1-11, 2012.

Bossu, J.L., et al.. 'Patch-Clamp Study of the Tetrodotoxin-Resistant Sodium Current in Group C Sensory Neurones', Neuroscience Letters, vol. 51, pp. 241-246, 1984.

Brinkmann, U., et al., "Phage Display of Disulfide-Stabilized FV Fragments," J. Immunol. Methods, vol. 182, No. 1, pp. 41-50, 1995.

Burton, D.R., et al., "Human Antibodies from Combinatorial Libraries," Advances in Immunology, vol. 57, pp. 191-280, 1994.

Casset, F, et al., 'A Peptide Mimetic of an Anti-CD4 Monoclonal Antibody by Rational Design,' Biochemical and Biophysical Research Communications, vol. 307, pp. 198-205, 2003.

Chapman, A., 'PEGylated antibodies and antibody fragments for improved therapy: a review', Advanced Drug Delivery Reviews, vol. 54, No. 4, pp. 531-545, 2002.

Chapman, A.P., et al., 'Therapeutic antibody fragments with prolonged in vivo half-lives', Nature Biotechnology, vol. 17, pp, 780-783, 1999.

Chen et al.. 'Selection and Analysis of an Optimized Anti-VEGF Antibody: Crystal Structure of an Affinity-matured Fab in Complex with Antigen,' J. Mol. Biol., vol. 293, pp. 865-881 (1999).

Chothia, C. and Lesk, A.M., "Canonical Structures for the Hypervariable Regions of Immunoglobulins," J. Mol. Biol., vol. 196, pp. 901-917, 1987.

Co-pending U.S. Appl. No. 14/547,291, filed Nov. 19, 2014.

Co-pending U.S. Appl. No, 15/014,145, filed Feb. 3, 2016.

Cole, S.P.C., et al., "The EBV-hybridoma technique and its application to human lung cancer," Monoclonal Antibodies and Cancer Therapy, vol. 27, (UCLA Symposia on Molecular and Cellular Biology, New Series, R.A. Reisfeld and S. Sell (eds.)), pp. 77-96, Alan R. Liss, Inc., N.Y., 1985.

Cox, J.J., et al., 'An SCN9A channelopathy causes congenital inability to experience pain', Nature, vol. 444, No. 7121, pp, 894-898, 2006.

Cummins, T. R., et al., 'Electrophysiological Properties of Mutant Nav1.7 Sodium Channels in a Painful Inherited Neuropathy', The Journal of Neuroscience, 24(38), pp. 8232-8236, 2004.

Cummins, Theodore R. et al., "The roles of sodium channels in nociception: implications for mechanisms of pain," Pain. Oct. 2007, vol. 131, No. 3, pp. 243-257.

De Genst, E., et al., 'Molecular basis for the preferential cleft recognition by dromedary heavy-chain antibodies', PNAS, vol. 103, No. 12, pp. 4586-4591, 2006.

De Pascalis, R. et al., 'Grafting of 'Abbreviated' Complementary-Determining Regions Containing Specificity-Determining Residues Essential for Ligand Contact to Engineer a Less Immuogenic Humanized Monoclonal Antibody,' Journal of Immunology, vol. 169, pp. 3076-3084, 2002.

(56) References Cited

OTHER PUBLICATIONS

Decanniere, K., et al., 'Canonical antigen-binding loop structures in immunoglobulins: more structures, more canonical classes?', J. Mol. Biol., vol. 300, No. 1, pp. 83-91, 2000.
Dellemijn, Paul, 'Are opioids effective in relieving neuropathic pain?', International Association for the Study of Pain, 80(3), pp. 453-462, 1999.
Desmyter, et al., 'Crystal structure of a camel single-domain VH antibody fragment in complex with lysozyme', Nat. Struct. Biol., vol, 3, pp. 803-811, 1996.
Dib-Hajj, et al., 'Genetics and Molecular Pathophysiology of Nav1.7-Related Pain Syndromes', Advances in Genetics, vol. 63, pp. 85-110, 2008.
Dib-Hajj, et al., 'Voltage-Gated Sodium Channels' Therapeutic Targets for Pain, American Academy of Pain Medicine, vol. 10, No. 7, pp. 1260-1269, 2009.
Doyle, D.A., et al., The Structure of the Potassium Channel: Molecular Basis of $K^+$ Conduction and Selectivity, Science, vol. 280, No. 5360, pp. 69-77, 1998.
Dworkin, R.H., 'An Overview of Neuropathic Pain: Syndromes, Symptoms, Signs and Several Mechanisms,' Clinical J. Pain, vol. 18, No. 6, pp. 343-349, 2002.
Frampton, J. E., et al., 'Pregabalin—In the Treatment of Painful Diabetic Peripheral Neuropathy', Adis Drug Profile, 64(24), pp. 2813-2820, 2004.
French, C.R., et al., 'A Threshold Sodium Channel in Pyramidal Cells in Rat Hippocampus', Neuroscience Letters, vol. 56, pp. 289-294, 1985.
Gilly, W.F., et al., 'Properties of appropriately and inappropriately expressed sodium channel in squid giant axon and its somata', J. Neurosci., vol. 9; No. 4, pp. 1362-1374, 1989.
Gilly, W.F., et al., 'Threshold channels—a novel type of sodium channel in squid giant axon', Nature, vol. 309, pp. 448-450, 1984.
Goldberg, et al., 'Loss-of-function mutations in the Nav1.7 gene underlie congenital indifference to pain in multiple human populations', Clinical Genetics, vol. 71, No. 4; pp. 311-319, 2007.
Gomes. P., et al., 'Antigenicity modulation upon peptide cyclization: application to the GH loop of foot-and-mouth disease virus strain C1-Barcelona', Vaccine, 19(25-26), pp. 3459-3466, 2001.
Gonoi, T., et al., 'Voltage Clamp Analysis of Tetrodotoxin-sensitive and --insensitive Sodium Channels in Rat Muscle Cells Developing in Vitrol', J. Neurosci., vol. 5, No. 9, pp. 2559-2564, 1985.
Gross, M.F., 'Aryl sulfonamide tetralin inhibitors of the Kv1.5 ion channel', Bioorganic & Medicinal Chemistry Letters, vol. 19, No. 11, pp. 3063-3066, 2009.
Gurrath, M., et al., 'Conformation/activity studies of rationally designed potent anti-adhesive RGD peptides', Eur. J. Biochem., vol. 210, No. 3, pp. 911-921, 1992.
Hamers-Casterman, C., et al., 'Naturally Occurring Antibodies Devoid of Light Chains,' Nature, vol. 363, pp. 446-448, 1993.
Harris, R.J., "Processing of C-terminal lysine and arginine residues of proteins isolated from mammalian cell culture," Journal of Chromatography, vol. 705, No. 1, pp. 129-134, 1995.
He, J.X., et al., 'An efficient strategy for the large-scale synthesis of head-to-tail cyclic peptides', Letters in Peptide Science, vol. 1, No. 1, pp. 25-30, 1994.
Hill, R.A., et al., 'Hydroxyl-substituted sulfonylureas as potent inhibitors of specific [3H] glyburide binding to rat brain syriabtosornes', Bioorg Med Chem, vol. 11, No. 9, pp. 2099-2113, 2003.
Holliger, P., et al., "Engineered antibody fragments and the rise of single domains," Nature Biotechnology, vol. 23, No. 9, pp. 1126-1136, Sep. 2005.
Hoyt, .B., et al., 'Benzazepinone Nav1.7 blockers: potential treatments for neuropathic pain', Bioorg. Med. Chem. Lett., vol. 17, No. 22, pp. 6172-6177, 2007.
Ikeda, S.R., et al., 'Na+ and Ca+ currents of acutely isolated adult rat nodose ganglion cells', J. Neurophysiol., vol. 55, pp. 527-539, 1986.

International Search Report based on PCT/EP2010/066274 dated Feb. 10, 2011.
International Search Report based on PCT/EP2010/066276 dated Feb. 10, 2011.
International Search Report based on PCT/EP2010/066279 dated Feb. 7, 2011.
Izumiya, N., et al., 'Synthesis of biologically active cyclic peptides', Biopolymers, vol. 20, No. 9, pp. 1785-1791, 1981.
Jarvis, Michael F. et al., "A-803467, a potent and selective Nav1.8 sodium channel blocker, attenuates neuropathic and inflammatory pain in the rat," PNAS, vol. 104, No. 20, May 15, 2007, pp. 8520-8525.
Jiang, Y., et al., 'The principle of gating charge movement in a voltage-dependent $K^+$ channel', Nature, vol. 423, No. 33, pp. 42-48, 2003.
Jones, S.W., 'Sodium Currents in Dissociated Bull-Frog Sympathetic Neurones', J. Physiol., vol. 389, pp. 605-627, 1987.
Kashmiri, S.V.S., et al., 'SDR grafting—a new approach to antibody humanization', Methods, vol. 36, pp. 25-34, 2005.
Kessler, H., et al., "Design of conformationally restricted cyclopeptides for the inhibition of cholate uptake of hepatocytes", Computer-Aided Drug Design, Methods and Applications, (Perun, T. J. & Propst, C. L., eds), pp. 461-484, Marcel Dekker, New York, 1989.
Kettleborough, C.A., et al., "Isolation of tumor cell-specific single-chain Fv from immunized mice using phage-antibody libraries and the reconstruction of whole antibodies from these antibody fragments," Eur. J. Immunol., vol. 24, No. 4, pp. 952-958, 1994.
Klionsky, L., et al., A Polyclonal Antibody to the Prepare Loop of Transient Receptor Potential Vanilloid Type 1 Blocks Channel Activation, The Journal of Pharmacology and Experimental Therapeutics, vol. 319, No. 1, pp. 192-198, 2006.
Kohler, G. et al., Continuous cultures of fused cells secreting antibody of predefined specificity, Nature, Aug. 7, 1975, pp. 495-497, vol. 256, nature Publishing Group.
Kostyuk, P.G., et al., 'Ionic currents in the somatic membrane of rat dorsal root ganglion neurons. I. Sodium currents'. 1, vol. 6, No. 12, pp. 2423-2430, 1981.
Kozbor, D., et al., "The production of monoclonal antibodies from human lymphocytes," Immunology Today, vol. 4, No. 3, pp. 72-79, 1983.
Lauwereys, M., et al.. 'Potential enzyme inhibitors derived from dromedary heavy-chain antibodies', EMBO Journal, vol. 17, pp. 3512-3520, 1998.
Leong, S.R., et al., 'Adapting pharmacokinetic properties of a humanized anti-interleukin-8 antibody for therapeutic applications using site-specific pegylation', Cytokine, vol. 16, No. 3; pp. 106-119, 2001.
Liao, Yaping Joyce, et al., "Anti-Ca2+ channel antibody attenuates Ca2+ currents and mimics cerebellar ataxia in vivo," Proc. Natl. Acad. Sci. USA, 2008, vol. 105, No. 7, pp. 2705-2710.
Liu, J.L., et al., 'Isolation of anti-toxin single domain antibodies from a semi-synthetic spiny dogfish shark display library', BMC Biotechnology, vol. 7:78, 2007.
Llinas, et al., 'Electrophysiological properties of in vitro Purkinje cell dendrites in mammalian cerebellar slices', J. Physiol, (Lond.), vol. 305, pp. 197-213, 1980.
Long, S.B., et al., 'Crystal Structure of a Mammalian Voltage-Dependent Shaker Family $K^+$ Channel', Science, vol. 309, No. 5736, pp. 897-903, 2005.
MacCullum, et al., 'Antibody-antigen interactions: Contact analysis and binding site topography', J. Mol. Biol. 1996, vol. 262, No. 5, pp. 732-745, 1996.
McGowan, et al., 'A Peripherally Acting Nav1.7 Sodium Channel Blocker Reverses Hyperalgesia and Allodynia on Rat Models of inflammatory and Neuropathic Pain', Anesthesia and Analgesia, vol. 109, No. 3, pp. 951-958, 2009.
Meiri, H. et al., 'Monoclonal Antibodies Associated with Sodium Channel Block Nerve Impulse and Stain Nodes of Ranvier,' Brain Research, vol. 310, No. 1, pp. 168-173, 1984.
Meiri, H., 'Detection of cell surface sodium channels by monoclonal antibodies—could the channels become exposed to the external

(56) References Cited

OTHER PUBLICATIONS surface and 'down regulated' by binding to antibodies?', Brain Research, vol. 368, Issue 1, pp. 188-192, Mar. 1986.
Mountain, A., et al., "Engineering antibodies for therapy," Biotechnol. Genet. Eng. Rev., vol. 10, pp. 1-142, 1992.
Muyidermans, S., et al., 'Recognition of antigens by single-domain antibody fractions: the superfluous luxury of paired domains', Trends in Biochem. Sci., vol. 26, pp. 230-235, 2001.
Namaka, et al., 'A Treatment Algorithm for Neuropathic Pain', Clinical Therapeutics, vol. 26, No. 7, pp. 951-979, 2004.
Naylor, J. et al., "Production of a specific extracellular inhibitor of TRPM3 channels," British Journal of Pharmacology, 2009, vol. 155, No. 4, pp. 567-573.
Nguyen, V,K., et al., 'Functional heavy-chain antibodies in Camelidae', Adv. Immunol., vol. 79, pp. 261-296, 2001.
Nygren, P., et al., 'Scaffolds for engineering novel binding sites in proteins', Current Opinion in Structural Biology, vol. 7, No. 4, pp. 463-469, 1997.
Orlandi, et al., 'Cloning immunoglobulin variable domains for expression by the polymerase chain reaction', PNAS USA, vol. 86, pp. 3833-3837, May 1989.
Persic, L., et al., "An integrated vector system for the eukaryotic expression of antibodies or their fragments after selection from phage display libraries," Gene, vol. 187, No. 1, pp. 9-18, 1997.
Pullar, S. et al., 'Pharmacotherapy for Neuropathic Pain: Progress and Prospects,' Drug News Perspect., vol. 16, No. 9, pp. 622-630, 2003.
Rasband, M.N., et al., 'Distinct potassium channels on pain-sensing neurons', PNAS, vol. 98, No. 23, pp. 13373-13378, 2001.
Related U.S. Appl. No. 12/913,145, filed Oct. 27, 2010, now U.S. Pat. No. 8,734,798 dated May 27, 2014.
Related U.S. Appl. No. 13/504,234, filed Jun. 28, 2012, now U.S. Pat. No. 8,926,977, dated Jan. 6, 2015.
Related U.S. Appl. No. 13/504,259, filed Jul. 6, 2012, now U.S. Pat. No. 9,067,995, dated Jun. 30, 2015.
Related U.S. Appl. No. 13/523,104, filed Jun. 14, 2012, now U.S. Pat. No. 9,234,037, dated Jan. 12, 2016.
Related U.S. Appl. No. 14/285,721, filed May 23, 2014, now U.S. Pat. No. 8,986,954, dated Mar. 24, 2015.
Related U.S. Appl. No. 14/585,406, filed Dec. 30, 2014, now U.S. Pat. No. 9,266,953, dated Feb. 23, 2016.
Renfrey S., et al., 'The painful reality', Nature Reviews, vol. 2, pp. 175-176, Mar. 2003.
Riechmann, et al., 'Reshaping human antibodies for therapy', Nature, vol. 332, pp. 323-324, 1988.
Rudikoff, Stuart et al., 'Single amino acid substitution altering antigen-binding specificity,' Proc. Natl. Acad. Sci, USA, 79:1979-1983, Mar. 1982.
Saerens, D.. et al., Single Domain Antibodies Derived from Dromedary Lymph Node and Peripheral Blood Lymphocytes Sensing Conformational Variants of Prostate-specific Antigen, J. Biol. Chem., vol. 279, No. 50, pp. 51965-51972, 2004.

Schmalhofer, W.A., et al., 'ProTx-II, a Selective Inhibitor of Na.sub.v1.7 Sodium Channels, Blocks Action Potential Propagation in Nociceptors', Mol Pharmacol, vol. 74, pp. 1476-1484, 2008.
Stanfield, R.L., et al., 'Crystal Structure of a Shark Single-Domain Antibody V Region in Complex with Lysozyme', Science, vol. 305, No. 5691, pp. 1770-1773, 2004.
Tao, M., et al., 'Structural Features of Human Immunoglobulin G that Determine Isotype-specific Differences in Complement Activation', J. Exp. Med, vol. 178, pp. 661-667, 1993.
Tao. M.. et al., 'The Differential Ability of Human IgG1 and IgG4 to Activate Complement is Determined by the COOH-terminal Sequence of the C.sub.H2 Domain', J. Exp. Med, vol. 173, pp. 1025-1028, 1991.
Tarnawa, I., et al., 'Blockers of voltage-gated sodium channels for the treatment of central nervous system diseases', Recent Patents on CNS Drug Discovery, vol. 2, pp. 57-78, 2007.
Teruya K., et al., In Peptides, Structure and Function, Proceedings of the Eighth American Peptide Symposium, Eds. V.J. Hruby and D.H. Rick, Pierce Chemical Company, Rockford, Illinois, pp. 127-130, 1983.
Tickle, S., et al., 'High-Throughput Screening for High Affinity Antibodies', Journal of the Association for Laboratory Automation, vol. 14, pp. 303-307, 2009.
Toniolo, C., 'Conformationally Restricted Peptides Through Short-Range Cyclizations', Int. J. Pept. Protein Res., vol. 35, pp. 287-300, 1990.
Translation of Japanese Examination Report dated Oct. 22, 2014 for Japanese Application No. 2012-535812.
Valero, M.L. et al., 'Cyclic Peptides as Conformationally Restricted Models of Viral Antigens: Application to Foot-and-Mouth Disease Virus,' Biomedical Peptides, Proteins & Nucleic Acids, vol. 1, No. 3, pp. 133-140, 1995.
Vaughan, et al., 'Human antibodies by design,' Nature Biotechnology, vol. 16, No. 6, pp. 535-539, 1998.
Verma, R., et al., "Antibody engineering: comparison of bacterial, yeast, insect and mammalian expression systems," Journal of Immunological Methods, vol. 216, Nos. 1-2, pp. 165-181, 1998.
Ward, E.S., et al., "Binding activities of a repertoire of single irnrnunoglobulin variable domains secreted from *Escherichia coil*," Nature, vol. 341, No. 6242, pp. 544-546, Oct. 12, 1989.
Weiss, R.E., et al., 'Functional differences between two classes of sodium channels in developing rat skeletal muscle', Science, vol. 233, pp. 361-364, 1986.
Wu et al., 'Humanization of a Murine Monoclonal Antibody by Simultaneous Optimization of Framework and CDR Residues,' J. Mol. Biol., vol. 294, pp. 151-162 (1999).
Yang, J., et al., '3-(4-Phenoxyphenyl)pyrazoles: A Novel Class of Sodium Channel Blockers', J. Med. Chem., vol. 47, No. 6, pp. 1547-1552, 2004.
Zucker, L.S., et al., 'Chimeric Human-Mouse IgG Antibodies with Shuffled Constant Region Exons Demonstrate that Multiple Domains Contribute to in Vivo Half-Life', Cancer Research, vol. 58, pp. 3905-3908, 1998.

\* cited by examiner

Figure 1b
Domain A (SEQ ID NO: 65)
MAMLPPPGPQSFVHFTKQSLALIEQRIAERKSKEPKEEKKDDDEEAPKPSSDLEAGKQLPFIYGDIPP
GMVSEPLEDLDPYYADKKTFIVLNKGKTIFRFNATPALYMLSPFSPLRRISIKILVHSLFSMLIMCTI
LTNCIFMTMNNPPDWTKNVEYTFTGIYTFESLVKILARGFCVGEFTFLRDPWNWLDFVVIVFAYLTEF
VNLGNVSALRTFRVLRALKTISVIPGLKTIVGALIQSVKKLSDVMILTVFCLSVFALIGLQLFMGNLK
HKCFRNSLENNETLESIMNTLESEEDFRKYFYYLEGSKDALLCGFSTDSGQCPEGYTCVKIGRNPDYG
YTSFDTFSWAFLALFRLMTQDYWENLYQQTLRAAGKTYMIFFVVVIFLGSFYLINLILAVVAMAYEEQ
NQANIEEAKQKELEFQQMLDRLKKEQEEAEAIAAAAAEYTSIRRSRIMGLSESSSETSKLSSKSAKER
RNRRKKKNQKKLSSGEEKGDAEKLSKSESEDSIRRKSFHLGVEGHRRAHEKRLSTPNQSPLSIRGSLF
SARRSSRTSLFSFKGRGRDIGSETEFADDEHSIFGDNESRRGSLFVPHRPQERRSSNISQASRSPPML
PVNGKMHSAVDCNGVVSLVDGRSALMLPNGQLLPEVIIDKATSDDSGTTNQIHKKRRCSSYLLSEDML
NDPNLRQRAMSRASILTNTVEELEESRQKCPPWWYRFAHKFLIWNCSPYWIKFKKCIY

Domain B (SEQ ID NO: 66)
FIVMDPFVDLAITICIVLNTLFMAMEHHPMTEEFKNVLAIGNLVFTGIFAAEMVLKLIAMDPYEYFQV
GWNIFDSLIVTLSLVELFLADVEGLSVLRSFRLLRVFKLAKSWPTLNMLIKIIGNSVGALGNLTLVLA
IIVFIFAVVGMQLFGKSYKECVCKINDDCTLPRWHMNDFFHSFLIVFRVLCGEWIETMWDCMEVAGQA
MCLIVYMMVMVIGNLVVLNLFLALLLSSFSSDNLTAIEEDPDANNLQIAVTRIKKGINYVKQTLREFI
LKAFSKKPKISREIRQAEDLNTKKENYISNHTLAEMSKGHNFLKEKDKISGFGSSVDKHLMEDSDGQS
FIHNPSLTVTVPIAPGESDLENMNAEELSSDSDSEYSKVRLNRSSSSECSTVDNPLPGEG
EEAEAEPMNSDEPEACFTDGCVRRFSCCQVNIESGKGKIWWNIRKTCYK

Domain C (SEQ ID NO: 67)
IVEHSWFESFIVLMILLSSGALAFEDIYIERKKTIKIILEYADKIFTYIFILEMLLKWIAYGYKTYFT
NAWCWLDFLIVDVSLVTLVANTLGYSDLGPISLRTLRALRPLRALSRFEGMRVVVNALIGAIPSIMNV
LLVCLIFWLIFSIMGVNLFAGKFYECINTTDGSRFPASQVPNRSECFALMNVSQNVRWKNLKVNFDNV
GLGYLSLLQVATFKGWTIIMYAAVDSVNVDKQPKYEYSLYMYIYFVVFIIFGSFFTLNLFIGVIIDNF
NQQKKKLGGQDIFMTEEQKKYYNAMKKLGSKKPQKPIPRPGNKIQGCIFD

Domain D (SEQ ID NO: 68)
LVTNQAFDISIMVLICLNMVTMMVEKEGQSQHMTEVLYWINVVFIILFTGECVLKLISLRHYYFTVGW
NIFDFVVVIISIVGMFLADLIETYFVSPTLFRVIRLARIGRILRLVKGAKGIRTLLFALMMSLPALFN
IGLLLFLVMFIYAIFGMSNFAYVKKEDGINDMFNFETFGNSMICLFQITTSAGWDGLLAPILNSKPPD
CDPKKVHPGSSVEGDCGNPSVGIFYFVSYIIISFLVVVNMYIAVILENFSVATEESTEPLSEDDFEMF
YEVWEKFDPDATQFIEFSKLSDFAAALDPPLLIAKPNKVQLIAMDLPMVSGDRIHCLDILFAFTKRVL
GESGEMDSLRSQMEERFMSANPSKVSYEPITTTLKRKQEDVSATVIQRAYRRYRLRQNVKNISSIYIK
DGDRDDDLLNKKDMAFDNVNENSSPEKTDATSSTTSPPSYDSVTKPDKEKYEQDRTEKEDKGKDSKES
KK

Figure 1c
Nav1.7 (SEQ ID NO: 69)

MAMLPPPGPQSFVHFTKQSLALIEQRIAERKSKEPKEEKKDDDEEAPKPSSDLEAGKQLPFIYGDIPP
GMVSEPLEDLDPYYADKKTFIVLNKGKTIFRFNATPALYMLSPFSPLRRISIKILVHSLFSMLIMCTI
LTNCIFMTMNNPPDWTKNVEYTFTGIYTFESLVKILARGFCVGEFTFLRDPWNWLDFVVIVFAYLTEF
VNLGNVSALRTFRVLRALKTISVIPGLKTIVGALIQSVKKLSDVMILTVFCLSVFALIGLQLFMGNLK
HKCFRNSLENNETLESIMNTLESEEDFRKYFYYLEGSKDALLCGFSTDSGQCPEGYTCVKIGRNPDYG
YTSFDTFSWAFLALFRLMTQDYWENLYQQTLRAAGKTYMIFFVVVIFLGSFYLINLILAVVAMAYEEQ
NQANIEEAKQKELEFQQMLDRLKKEQEEAEAIAAAAAEYTSIRRSRIMGLSESSSETSKLSSKSAKER
RNRRKKKNQKKLSSGEEKGDAEKLSKSESEDSIRRKSFHLGVEGHRRAHEKRLSTPNQSPLSIRGSLF
SARRSSRTSLFSFKGRGRDIGSETEFADDEHSIFGDNESRRGSLFVPHRPQERRSSNISQASRSPPML
PVNGKMHSAVDCNGVVSLVDGRSALMLPNGQLLPEVIIDKATSDDSGTTNQIHKKRRCSSYLLSEDML
NDPNLRQRAMSRASILTNTVEELEESRQKCPPWWYRFAHKFLIWNCSPYWIKFKKCIYFIVMDPFVDL
AITICIVLNTLFMAMEHHPMTEEFKNVLAIGNLVFTGIFAAEMVLKLIAMDPYEYFQVGWNIFDSLIV
TLSLVELFLADVEGLSVLRSFRLLRVFKLAKSWPTLNMLIKIIGNSVGALGNLTLVLAIIVFIFAVVG
MQLFGKSYKECVCKINDDCTLPRWHMNDFFHSFLIVFRVLCGEWIETMWDCMEVAGQAMCLIVYMMVM
VIGNLVVLNLFLALLLSSFSSDNLTAIEEDPDANNLQIAVTRIKKGINYVKQTLREFILKAFSKKPKI
SREIRQAEDLNTKKENYISNHTLAEMSKGHNFLKEKDKISGFGSSVDKHLMEDSDGQSFIHNPSLTVT
VPIAPGESDLENMNAEELSSDSDSEYSKVRLNRSSSSECSTVDNPLPGEGEEAEAEPMNSDEPEACFT
DGCVRRFSCCQVNIESGKGKIWWNIRKTCYKIVEHSWFESFIVLMILLSSGALAFEDIYIERKKTIKI
ILEYADKIFTYIFILEMLLKWIAYGYKTYFTNAWCWLDFLIVDVSLVTLVANTLGYSDLGPISLRTLR
ALRPLRALSRFEGMRVVVNALIGAIPSIMNVLLVCLIFWLIFSIMGVNLFAGKFYECINTTDGSRFPA
SQVPNRSECFALMNVSQNVRWKNLKVNFDNVGLGYLSLLQVATFKGWTIIMYAAVDSVNVDKQPKYEY
SLYMYIYFVVFIIFGSFFTLNLFIGVIIDNFNQQKKKLGGQDIFMTEEQKKYYNAMKKLGSKKPQKPI
PRPGNKIQGCIFDLVTNQAFDISIMVLICLNMVTMMVEKEGQSQHMTEVLYWINVVFIILFTGECVLK
LISLRHYYFTVGWNIFDFVVVIISIVGMFLADLIETYFVSPTLFRVIRLARIGRILRLVKGAKGIRTL
LFALMMSLPALFNIGLLLFLVMFIYAIFGMSNFAYVKKEDGINDMFNFETFGNSMICLFQITTSAGWD
GLLAPILNSKPPDCDPKKVHPGSSVEGDCGNPSVGIFYFVSYIIISFLVVVNMYIAVILENFSVATEE
STEPLSEDDFEMFYEVWEKFDPDATQFIEFSKLSDFAAALDPPLLIAKPNKVQLIAMDLPMVSGDRIH
CLDILFAFTKRVLGESGEMDSLRSQMEERFMSANPSKVSYEPITTTLKRKQEDVSATVIQRAYRRYRL
RQNVKNISSIYIKDGDRDDDLLNKKDMAFDNVNENSSPEKTDATSSTTSPPSYDSVTKPDKEKYEQDR
TEKEDKGKDSKESKK

Figure 3e
(a)
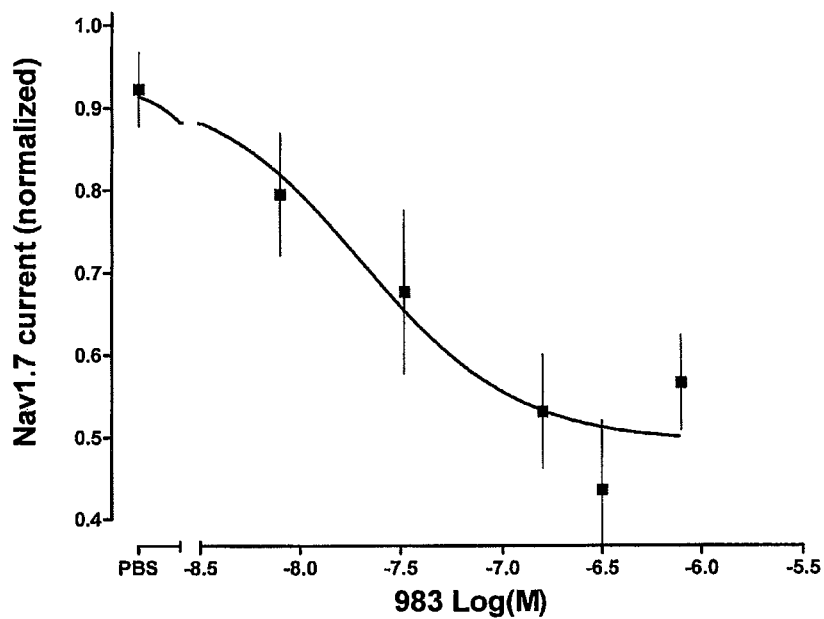
(b)
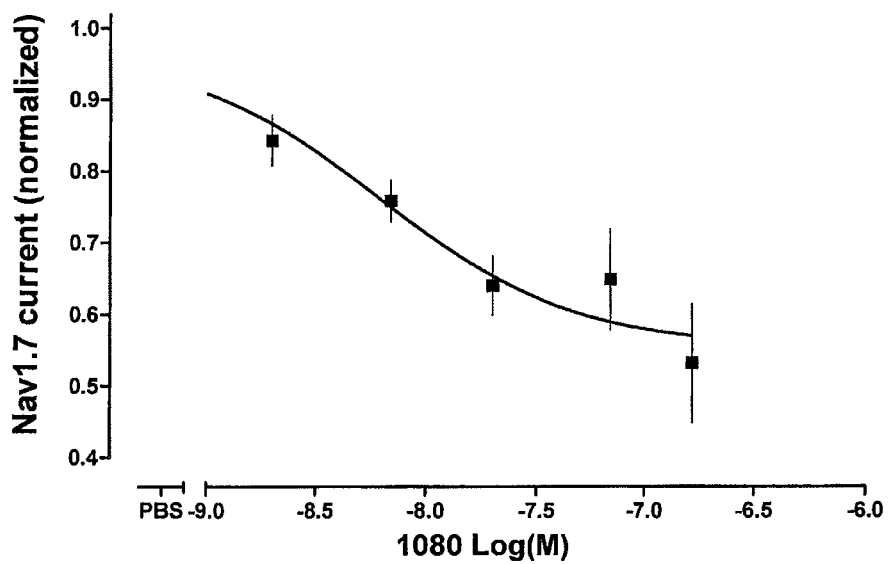

Figure 6

Light DNA CA167_00914 (SEQ ID NO: 1)
```
GCCTATGATA TGACCCAGAC TCCAGCCTCT GTGGAGGTAG CACAGTCACC ATCAATTGCC AGGCCAGTGA GAGCATTGGC
ACTGCATTAG CCTGGTATCA GCAGAAACCA GGGCAGCCTC CCAAGCTCCT GATCTACAAG GCATCCACTC TGGAATCTGG
CGGTTCAAAG GCGGTGGATC TGGGACACAG TTCACTCTCA CCATCAGCGG CGTGCAGTGT GACGATGCTG CCACTTACTA
GGTGAAACTG CAAATAGAAT TGATAATGCT TTCGGCGAGT GGACCGAGGT GGTCGTCAAA
```

Heavy DNA CA167_00914 (SEQ ID NO: 2)
```
CAGTCGGTGG AGGAGTCCGG CCTGGGTCCG GGTCGCCTG TTCACTCTCA CCATCAGCGG CGTGCAGTGT GACGATGCTG CCACTTACTA CCTCAGTCGC
AATGCAATGA CCTGGGTCCG CCAGGCTCCA GGGAAGGGGC TGGAATACAT CGCATACATT AATACTAGGG GTGACACATC CTACGCGAAC
TGGGCGAAAG GCCGATTCAC CATCTCCAAA ACCTCGACCA CGGTGGATCT GAAAATGACC AGTCTGACAA CCGAGGACAC GGCCACCTAT
TTCTGTGTTC ATGGTTATAA TCCCTGTAAG TTGTGGGGGC AAGGCACCCT GGTCACCGTC TCG
```

Light Protein CA167_00914 (SEQ ID NO: 3)
```
AYDMTQTPAS VEVAVGGTVT INCQASESIG TALAWYQQKP GQPPKLLIYK ASTLESGVPS RFKGGGSGTQ FTLTISGVQC DDAATYYCQQ
GETANRIDNA FGGGTEVVVK
```

Heavy Protein CA167_00914 (SEQ ID NO: 4)
```
QSVEESGGRL VTPGTPLILT CTVSGIDLSR NAMTWVRQAP GKGLEYIAYI NTRGDTSYAN WAKGRFTISK TSTTVDLKMT SLTTEDTATY
FCVHGYNPCK LWGQGTLVTV S
```

Light DNA CA167_00915 (SEQ ID NO: 5)
```
GCCTATGATA TGACCCAGAC TCCAGCCTCT GTGGAGGTAG CACAGTCACC ATCAATTGCC AGGCCAGTGA GAGCATTAAC
ACTGCATTAG CCTGGTATCA GCAGAAACCA GGACAGCCCTC CCAAGGTCCT GATCTATGCT GCCTCCGATC TGGCATCTGG GGTCCCATCG
CGGTTCAAAG GCAGTGGATC TGGGAAACAG TTCACTCTCA CCATCAGCGG CGTGCAGTGT GCCGATGCTG CCACTTACTA CTGTCAACAG
GGTTATACTG CAAATAATAT TGATAATGCT TTCGGCGAGT GGACCGAGGT GGTCGTCAAA
```

Heavy DNA CA167_00915 (SEQ ID NO: 6)
```
CAGTCGGTGG AGGAGTCCGG CCTGGGTCCG GGTCGCCTG TTCACTCTCA CCATCAGCGG CGTGCAGTGT GACACTCACC TGCACAGTCT CTGGAATCGA CCTCAGTAGG
AATGCAATGA CCTGGGTCCG CCAGGCTCCA GGGAAGGGGC TGGAATACAT CGCATATATT AATACTAGGG GTGGCCATC CTACGCGAAC
TGGGCGAAAG GCCGATTCAC CATCTCCAAA ACCTCGACCA CGGTGGATCT GAAAATGACC AGTCTGACAG CTTCAGACAC GGCCACCTAT
TTCTGTGTCA ATGGTTATAA CCCCTGTAAG TTGTGGGGCC CGGGACCCT CGTCACCGTC TCG
```

Light Protein CA167_00915 (SEQ ID NO: 7)
```
AYDMTQTPAS VEVAVGGTVT INCQASESIN TALAWYQQKP GQPPKVLIYA ASDLASGVPS RFKGSGSGKQ FTLTISGVQC ADAATYYCQQ
GYTANNIDNA FGGGTEVVVK
```

Heavy Protein CA167_00915 (SEQ ID NO: 8)
```
QSVEESGGRL VAPGTPLILT CTVSGIDLSR NAMTWVRQAP GKGLEYIAYI NTRGGASYAN WAKGRFTISK TSTTVDLKMT SLTASDTATY
FCVNGYNPCK LWGPGILVTV S
```

Light DNA CA167_00930 (SEQ ID NO: 9)
```
GCCCAAGTGC TGACCCAGAC TCCATCTTCC ACGTCTGCAG CTGTGGGAGG CACAGTCACC ATCAATTGCC AGTCCAGTCA GAATGTTGTT
AATAACAACT GGTTCTCCTG GTTTCAGCAG AAACCAGGGC AGCCTCCCAA GGTCCTGATC TATTTTGTAT CCAAACTGGC ATCTGGGGTC
CCATCGCGGT TTAAAGGCAG TGGATCTGGG ACACAGTTCA CTCTCACCAT CAGCGACCTG CAGGACCTG GAGTGTGACG ATGCTGCCAC TTATTATTGT
GGAGGCGGTT ATAGTGATAA TATTTATGCG TTCGGCGAG GGACCGAGGT GGTCGTCGAA
```

Figure 6 continued

| | |
|---|---|
| Heavy DNA CA167_00930 (SEQ ID NO: 10) | CAGTCGGTGG AGGAGTCCGG GGGTCGCCTG GTCACGCCTG GGACACCCCT GGCACTCACC TGCACAGTCT CTGGAATCGA CCTCAGTTAC TATGCAATAA GCTGGGTCCG CCAGGCTCCA GGGAAGGGGC TGGAATACAT CGGAATCATT GGTAGTAGTG GTAGAACATA CTACGCGAGC TGGGCGAAAG GCCGATTCAC CATCTCCAAA ACCTCGACCA CGGTGGATCT GAAAATGACC AGTCTGACAA CCGAAGACAC GGCCACCTAT TTCTGTGTCA GGGGTGGTCC TACTTCTAGT CCTAGTTTGT GGGGCCAAGG CACCCTCGTC ACCGTCTCG AQVLTQTPSS TSAAVGGTVT INCQSSQNVV NNNWFSWFQQ KPGQPPKVLI YFVSKLASGV PSRFKGSGSG TQFTLTISDL ECDDAATYYC GGGYSDNIYA FGGGTEVVVE |
| Light Protein CA167_00930 (SEQ ID NO: 11) | QSVEESGGRL VTPGTPLALT CTVSGIDLSY YAISWVRQAP GKGLEYIGII GSSGRTYYAS WAKGRFTISK TSTTVDLKMT SLTTEDTATY FCVRGGPTSS PSLWGQGTLV TVS |
| Heavy Protein CA167_00930 (SEQ ID NO: 12) | |

Figure 7

Light DNA CA167_00931 (SEQ ID NO: 13)

GACATCGTGA TGACCCAGAC TCCATCCTCC GTGTCTGCAG CTGTGGGAGG CACAGTCACC ATCAATTGCC AGGCCAGTCA GAGTGTTTAT
GGGACCAACC GTTTATCCTG GTATCAGCAG AAACCAGGGC AGCGTCCCAA GCTCCTGATC TATGGTGCAT CCACTCTGAC ATCTGGGGTC
CCATCGCGGT TCAAAGGCAG TGGATCTGGG ACACAGTTCA CTCTCACCAT CAGTGGCGTG CAGTGTGATG ATGCTGCCAC TTACTACTGT
CTAGGCGGTT GGTTTGAAAG CTTGATTGGG CTTCGGCCG

Heavy DNA CA167_00931 (SEQ ID NO: 14)

CAGTCGGTGG AGGAGTCCGG GGGTCGCCTG GTCACGCCTG GGACACCCCT GGACACTCACC TGTACAGTCT CTGGAATCGA CCTCAGTAGA
AATGCAATGG GCTGGGTCCG CCAGGCTCCA GGAAAGGGGC TGGAATACAT CGGAGTCGTG GTAACATATG GTTCAGGAAC
TGGGGAAAAG GCCGATTCAC CGTCTCCAAA ACCTGACCA CGGTGGATCT AAAAATCACC AGTCCGACAA CCGAGGACAC GGCCACCTAT
TTCTGTGCA GATTTCTTGT AGTATCTGGG GTGGGACTT TTGATCCCTG GGGCCAGGG ACCCTCGTCA CCGTCTCG

Light Protein CA167_00931 (SEQ ID NO: 15)

DIVMTQTPSS VSAAVGGTVT INCQASQSVY GTNRLSWYQQ KPGQRPKLLI YGASTLTSGV PSRFKGSGSG TQFTLTISGV QCDDAATYYC
LGGWFESSSS LDWAFGGGTE VVVE

Heavy Protein CA167_00931 (SEQ ID NO:16)

QSVEESGGRL VAPGTPLTLT CTVSGIDLSR NAMGWVRQAP EKGLEYIGHI ASRGNIWFRN WAKGRFTVSK TSTTVDLKIT SPTTEDTATY
FCGRFLVVSG VGTFDPWGQG TLVTVS

Light DNA CA167_00932 (SEQ ID NO: 17)

GCAGCCGTGC TGACCCAGAC TCCATCGTCC GTGTCTGCAG CTGTGGGAGG CACAGTCACC ATCAAGTGCC AGTCCAGTCA GAGTGTTTAT
AATAACAACG AATTTTCCTG GTATCAGCAG AAACCAGGAG GCTCCTGATC TATGATGCAT CCAAAATTGGC ATCTGGGGTC
CCATCGCGGT TCAGCGGCAG TGGATCTGGG ACACAGTTCA CTCTCACCAT CAGGGGCGTG CAGTGTGACG ATGTTGCCAC TTATTACTGT
CTAGGCGGTT ATAATGATGA TACTAATAGA TGGGCTTTCG GCCGAGGGAC CGAGGTGGTG GTCGAA

Heavy DNA CA167_00932 (SEQ ID NO: 18)

CAGTCGCTGG AGGAGTCCGG GGGTCGCCTG GTCACGCCTG GGACACCCCT GACACTCACC TGCACAGTCT CTGGATTCTC CCTCAGTCGC
TACTGGATGA GCTGGGTCCG CCAGGCTCCA GGGAAAACATT GGTGGTGGTA GTGGTAGTAC ATTATACGCG
CCCTGGGCAA AAGGCCGATC CACCATCTCC AAAACCTCGA CCACGGTGGA TCTGAAAATC ACCAGTCCGA CAACCGAGGA CACGGCCACC
TATTTCTGTG GCAGATATGT TAAAAATGGT GGTTGGATCT TTGGGGGCCA GGGACCCTGG TCACCGTCTC G

Light Protein CA167_00932 (SEQ ID NO: 19)

AAVLTQTPSS VSAAVGGTVT IKCQSSQSVY NNNEFSWYQQ KPGQPPKLLI YDASKLASGV PSRFSGSGSG TQFTLTISGV QCDDVATYYC
LGGYNDDTNR WAFGGGTEVV VE

Heavy Protein CA167_00932 (SEQ ID NO: 20)

QSLEESGGRL VTPGTPLTLT CTVSGFSLSR YWMSWVRQAP GKGLEWIGNI GGGSGSTLYA PWAKGRSTIS KTSTTVDLKI TSPTTEDTAT
YFCGRYVKNG GGYRLDLWGP GTLVTVS

Figure 7 continued

| | | | | | | | |
|---|---|---|---|---|---|---|---|
| Light DNA CA167_00933 (SEQ ID NO: 21) | GCCATCGTGA | TGACCCAGAC | TCCATCTTCC | AAGTCTGTCC | CTGTGGGAGA | CACAGTCACC | ATCAATTGCC AGGCCAGTGA GAGTGTTGCT |
| | AATAACAACT | GGTTAGCCTG | GTTTCAACAG | AAACCAGGGC | AGCCTCCCAA | GCTCCTGATC | TACAAGGCAT CCACTCTGGC ATCTGGGGTC |
| | TCATCGCGGT | TTAAAGGCAG | TGGATCTGGG | ACACAGTTCA | CTCTCACCAT | CGGCGATGTG | GTGTGTGACG ATGCTGCCAC TTACTATTGT |
| | GCAGGATATA | AAAGTAGTAC | TACTGATGCT | GTTGCTTTCG | GCGGAGGGAC | CGAGGTGGTG | GTCAAA |
| Heavy DNA CA167_00933 (SEQ ID NO: 22) | CAGTCAGTGA | AGGAGTCCGA | GGGAGGTCTC | TTCAAGCCAA | CGGATACCCT | GACACTCACC | TGCACAGTCT CTGGATTCTC CCTCAGTAGC |
| | TATGCAATAA | GCTGGGTCCG | CCAGGCTCCA | GGGAACGGGC | TGGAATGGAT | CGGATTCATT | AACACTATTA CTGGTGGCAC AAACTACGCG |
| | AGCTGGGCGA | AAAGCCGATC | CACCATCACC | AGAAACACCA | ACGATAACAC | GGTGACTCTG | AAAATGACCA GTCTGACAGC CGCGGACACG |
| | GCCACGTATT | TCTGTGCGAG | AAGTGGTGCC | TACTTTGACT | TGTGGGGCCC | AGGCACCCTG | GTCACCGTCT CG |
| Light Protein CA167_00933 (SEQ ID NO: 23) | AIVMTQTPSS | KSVPVGDTVT | INCQASESVA | NNNWLAWFQQ | KPGQPPKLLI | YKASTLASGV | SSRFKGSGSG TQFTLTIGDV VCDDAATYYC |
| | AGYKSSTTDA | VAFGGGTEVV | VK | | | | |
| Heavy Protein CA167_00933 (SEQ ID NO: 24) | QSVKESEGGL | FKPTDILTLT | CTVSGFSLSS | YAISWVRQAP | GNGLEWIGFI | NTITGGTNYA | SWAKSRSTIT RNTNDNTVTL KMTSLTAADT |
| | ATYFCARSGA | YFDLWGPGTL | VTVS | | | | |

Figure 8

Light DNA CA167_00983 (SEQ ID NO: 25)
GCCCAAGTGC TGACCCAGAC TGCATCCCCC GTGTCTGCGG CTGTTGGAGG CACAGTCACC ATCAATTGCC AGTCCAGTCA GAGTGTTTAT
AAGAACAACG ACTTAGCCTG GTATCAGCAG AAACCAGGGC AGCCTCCCAA GCTCCTGATC TATTATGCAT CCACTCTGGC ATCTGGGGTC
TCATCGCGGT TCAAAGGCAG TGGATCTGGG ACAGAGTTCA CTCTCACCAT CAGCGACGCG CAGTGTGACG ATGCTGCCAC TTACTACTGT
CTAGTAGTT ATGATTGTAG TAGTGCTGAT TGTAATGCTT TCGGCGGAGG GACCAAGGTG GACCAAGGTG GTCGTCAAA

Heavy DNA CA167_00983 (SEQ ID NO: 26)
CAGTCGGTGG AGGAGTCCGG GGGTCGCCTG GTCACGCCTG GGACACCCCT GGACACTCACC TGCACAGTCT CTGGATTCTC CCTCAGTAAC
TATGCAATGA GTTGGGTCCG CCAGGCTCCA GGGAAGGGGC TGGAATGAT CGGAATCATT GGTAAAAGTG GTAGTACGGC CTACGCGAGC
TGGGCGAAAG GCCGATTCAC CATCTCCAGA ACCTCGACCA CGGTGGATCT GGAAATCACC AGTCCGACAA CCGAGGACAC GGCCACCTAT
TTCTGTGTCA GATTTGTGCT CTTGTGGGGC CCGGGACCC TCGTCACCGT CTCG

Light Protein CA167_00983 (SEQ ID NO: 27)
AQVLTQTASP VSAAVGGTVT INCQSSQSVY KNNDLAWYQQ KPGQPPKLLI YYASTLASGV SSRFKGSGSG TEFTLTISDA QCDDAATYYC
LGSYDCSSAD CNAFGGGTKV VVK

Heavy Protein CA167_00983 (SEQ ID NO: 28)
QSVEESGGRL VTPGTPLTLT CTVSGFSLSN YAMSWVRQAP GKGLEWIGII GKSGSTAYAS WAKGRFTISR TSTTVDLEIT SPTTEDTATY
FCVRFVLLWG PGTLVTVS

Light DNA CA167_00984 (SEQ ID NO: 29)
GCGCAAGTGC TGACCCAGAC TCCATCCTCC GTGTCTGCAG CTGTTGGAGG CACAGTCACC ATCAATTGCC AGTCCAGTCA GAGTGTTAAT
AACAACAACT TCTTATCCTG GTATCAGCAG AAACCAGGGC AGCCTCCCAA CTCTCACCAT CAGCGACGTG TACGGGCCTT CCACTCTGGC ATCTGGGGTC
CCATCGCGGT TCAAAGGCAG TGGATCTGGG ACAGAGTTCA TTCGGCGGAG GGACCGAGTT CAGCGACGTG GGTGGTCGAA
GCAGGCGGTT ATAGTGGTAA TATTTATGCT GGGTCGCCTG GTCACGCCTG GGACACTCACC TGCACAGTCT CTGGATTCTC CCTCAGTGAC
CAGTCGGTGG AGGAGTCCGG ACTGGGTCCG CCAGGCTCCA GGGAAGGGGC TGGAATGAT CGGGATCATG GTACTAGTG GTACGCCATA GTACTAGTG CTACGCGAGC
TGGGCGAAAG GCCGATTCAC CATCTCCAAA ACCTCGTCGA ACCCGTGGA TCTGAGAATG ACCAGTCTGA CAACCGAGGA CACGGCCACC
TATTTCTGTG CCAGAGGGGG TGTTGCTACT TCTAATTTCT GGGGCCAAGG CACCCTGGTC ACCGTCTCG

Light Protein CA167_00984 (SEQ ID NO: 31)
AQVLTQTPSS VSAAVGGTVT INCQSSQSVN NNNFLSWYQQ KPGQPPKQLI YRASTLASGV PSRFKGSGSG TQFTLTISDV QCDDAATYFC
AGGYSGNIYA FGGGTEVVVE

Heavy Protein CA167_00984 (SEQ ID NO: 32)
QSVEESGGRL VTPGTPLTLT CTVSEFSLSD YIINWVRQAP GKGLEWIGIM GTSGTAYYAS WAKGRFTISK TSSTTVDLRM TSLTTEDTAT
YFCARGGVAT SNFWGQGTLV TVS

Figure 8 continued

Light DNA
CA167_00985
(SEQ ID NO: 33)
```
GCCCAAGTGC TGACCCAGAC TGCATCCCCT GTGTCTGCAG CTGTGGGAGG CACAGTCACC ATCAATTGTC AGTCCAGTCA GAGCGTTTAT
GGTAACAATT GGTTAGCCTG GTATCAGCAG AAACCAGGGC AGCCTCCCAA GCTCCTGATC TATTCTGCAT CTACTCTGGC ATCTGGGGTC
CCATCGCGGT TCAGTGGCAG TGGATCTGGG ACACAGTTCA CTCTCACCAT CAGCGACCTG GAGTGTGACG ATGGTGCCAC TTACTATTGT
GTAGGCGGGT ATAGTGGTAA TATTCATGTT TTCGGCGGAG GGACCAAGGT GGTGGTCGAA
```

Heavy DNA
CA167_00985
(SEQ ID NO: 34)
```
CAGTCGGTGG AGGAGTCCGG GGGTCGCCTG GTCACGCCTG GGACACCCCT GACACTCACC TGCACAGTCT CTGGATTCTC CCTCAACGAC
TACGACATGA GCTGGGTCCG CCAGGCTCCA GGGAAGGGGC TGGAATGGAT CACAACCATT TATGTTAGTG GTAACACATA CTACGCGACC
TGGGCGAAAG GCCGATTCAC CATCTCCAAA ACCTCGACCA CGGTGGATCT GAAAATGACC AGTCCGACAG CCGAGGACAC GGCCACCTAT
TTCTGTGCCA GAGCGGTTCC TGGTAGTGGT AAGGGGTTGT GGGGCCCGGG CACCCTCGTC ACCGTCTCG
```

Light Protein
CA167_00985
(SEQ ID NO: 35)
```
AQVLTQTASP VSAAVGGTVI INCQSSQSVY GNNWLGWYQQ KPGQPPKLLI YSASTLASGV PSRFSGSGSG TQFTLTISDL ECDDGATYYC
VGGYSGNIHV FGGGTKVVE
```

Heavy Protein
CA167_00985
(SEQ ID NO: 36)
```
QSVEESGGRL VTPGTPLTLT CTVSGFSLND YDMSWVRQAP GKGLEWITTI YVSGNTYYAT WAKGRFTISK TSTTVDLKMT SPTAEDTATY
FCARAVPGSG KGLWGPGTLV TVS
```

Figure 9

Light DNA CA167_01080 (SEQ ID NO: 37)
GCCCAAGTGC TGACCCAGAC TGCATCGCCC GTGTCTGCAG CTGTGGGAAA CACAGTCACC ATCACTTGCC AGTCCAGTCA GAGTGTTTGG
AAGAATAACG ACTTATCCTG GTATCAGCAG AAACTAGGGC AGCCTCCCAA GCTCCTGATC TATTATGCAT CCACTCTGGC ATCTGGGGTC
TCATCGCGGT TCAAAGCCAG TGGATCTGGG ACACAGTTCA CTCTCACCAT CAGCGACGTG CAATGTGACG ATGCTGCCAC TTACTACTGT
GTAGGCAGTT ATGATTGTAG TAGTGCTGAT TGTAATGCTT TCGGCGGAGG GACCAAGGTG GTCGTCAAA
CAGTCGCTGG AGGAGTCCGG CCTGGGTCCG GGTCGCCTG AGACACCCCT GACACTCACC TGCACAGCCT CTGGAATCGA CCTCAGTAAG
TGGCCAATGA CCTGGGTCCG CCAGGCTCCA GGGAAGGGAC TGGAGTGGAT CGGAGTGGAT CGGAATTATT GGTAGGAGTG TTACGCGAGC
TGGGCGAAAG GCCGATTCAC CATCTCCAAA ACCTCGACCA CGGTGGATCT GAAAATGACC AGTCCGACAA CCGAGGACAC GGCCACTTAT
TTCTGTGCCA GAGGTGGTAG TTATTATGAT TTGTGGGGCC AGGGGACCCT GGTCACCGTC TCG
AQVLTQTASP VSAAVGNTVT ITCQSSQSVW KNNDLSWYQQ KLGQPPKLLI YYASTLASGV SSRFKASGSG TQFTLTISDV QCDDAGTYYC
VGSYDCSSAD CNAFGGGTKV VVK

Heavy DNA CA167_01080 (SEQ ID NO: 38)

Light Protein CA167_01080 (SEQ ID NO: 39)

Heavy Protein CA167_01080 (SEQ ID NO: 40)
QSLEESGGRL VTPETPLTLT CTASGIDLSK WPMTWVRQAP GKGLEWIGII GRSGSTNYAS WAKGRFTISK TSTTVDLKMT SPTTEDTATY
FCARGGSYYD LWGQGTLVTV S

Light DNA CA167_01081 (SEQ ID NO: 41)
GCCGCCGTGC TGACCCAGAC TCCATCTCCC GTGTCTGCAG CTGTGGGAGG AAACCAGGGC AGCCTCCCAA GCTCCTGATC TATGATGCAT CCGATCTGGC ATCTGGGGTC
AATAACAACT ACTTATCCTG GTATCAGCAG AAACCAGGGC AGCCTCCCAA GCTCCTGATC TATGATGCAT CCGATCTGGC ATCTGGGGTC
CCATCGCGGT TCAAAGGCAG TGGATCTGGG ACACAGTTCA TTTTATGATT CAGCGACGTG CAGTGTGACG ATGCTGCCAC TTACTACTGT
GCAGGCGGTT ATATAACTAG TAGTGATATT TTTTATGATT TCGGCGGAGG GACCAAGGTG GTGGTCAAA
CAGTCGCTGG AGGAGTCCGG CCTGGGTCCT GTCACGCCTG GGACACCCCT GACACTCACC TGCACAGTCT CTGGATTCTC CCTCAGTACC
TATGCAATGA GCTGGGTCCG CCAGGCTCCA GGGAAGGGGC TGGAATGGAT CGGAATCGTT GGAAAGAGTG GTATTATAAA GTACGCGAGC
TGGGCGAAAG GCCGGTTCAC CATCTCCAAA ACCTCGACCA CGGTGGATCT GAAAATGACC AGTCTGACAA CCGAGGACAC GGCCATTTAT
TTCTGTGCCA GACTATGGAG CTTGTGGGGC CAAGGGACCC TCGTCACCGT CTCG
AAVLTQTPSP VSAAVGGTVS ISCQSSQSVD NNNYLSWYQQ KPGQPPKLLI YDASDLASGV PSRFKGSGSG TQFTLTISDV QCDDAATYYC
AGGYITSSDI FYDFGGGTKV VVK

Heavy Protein CA167_01081 (SEQ ID NO: 44)
QSVEESGGRL VTPGTPLTLT CTVSGFSLST YAMSWVRQAP GKGLEWIGIV GKSGIIKYAS WAKGRFTISK TSTTVDLKMT SLTTEDTAIY
FCARLWSLWG QGTLVTVS

Heavy DNA CA167_01081 (SEQ ID NO: 42)

Light Protein CA167_01081 (SEQ ID NO: 43)

Figure 10

Light DNA
CA167_01082
(SEQ ID NO: 45)

```
GACATTGTGA TGACCCAGAC TCCAGCCTCC GTGTCTGAAC CTGTGGGAGG CACAGTCACC ATCAAGTGCC AGGCCAGTCA
GAGCATTAGC AACTGGTTAG CCTGGTATCA GCAGAAACCA GGGCAGCCTC CCAAGCTCCT GATCTACAGG GCATCCACTC
TGGCATCTGG GGTCTCATCG CGGTTCAAAG GCAGTGGATC TGGGACAGAG TTCACTCTCA CCATCAGCGA CCTGGAGTGT
GCCGATGCTG CCACTTACTA CTGTCAAAGC GATTATGGTA TAGATACTTA TGGAAGTGCT TTCGGCGGAG GGACCAAGGT
GGTGGTCAAA
```

Heavy DNA
CA167_01082
(SEQ ID NO: 46)

```
CAGTCGCTGG AGGAGTCCCG GGGTCGCCTG GTCACGCCTG GGACACCCCT GACACTCACC TGCACAGTCT CTGGAATCGA
CCTCAGTAGT TATGCAATGA CCTGGGTCCG CCAGGCTCCA GGGAAGGGGC TGGAATGGAT CGGAATGGTT CGTCGTAGTG
GTACCACATA CTACGCGAGC TGGGCGAAAG GCCGATTCAC CATCTCCAAA ACCTCGACCA CGGTGGATCT GAAAATCATC
AGTCCGACAA CCGAGGACAC GGCCACCTAT TTCTGTGCCA GATGTGATAA TAGTGCTGGT GACTGGAGTT ACGGCATGGA
CCTCTGGGGC CCGGGGACCC TGGTCACCGT CTCG
```

Light Protein
CA167_01082
(SEQ ID NO: 47)

```
DIVMTQTPAS VSEPVGGTVT IKCQASQSIS NWLAWYQQKP GQPPKLLIYR ASTLASGVSS RFKGSGSGTE FTLTISDLEC
ADAATYYCQS DYGIDTYGSA FGGGTKVVVK
```

Heavy Protein
CA167_01082
(SEQ ID NO: 48)

```
QSLEESRGRL VTPGTPLTLT CTVSGIDLSS YAMTWVRQAP GKGLEWIGMV RRSGTTYYAS WAKGRFTISK TSTTVDLKII
SPTTEDTIATY FCARCDNSAG DWSYGMDLWG PGTLVTVS
```

Light DNA
CA167_01083
(SEQ ID NO: 49)

```
GCCCAAGTGC TGACCCAGAC TGCATCGCCC GTGTCTGCAG CTGTGGGAAG CACAGTCACC ATCAATTGCC AGGCCAGTCA
GAGTGTTTAT CAGAACAACT ACTTAGCCTG GTTTCAGCAG AAACCAGGGC AGCCTCCCAA GCGCCTGATC TATTCTGCAT
CCACTCTGGC ATCTGGGGTC TCATCGCGGT TCAAAGGCAG TGGATCTGGG ACACAGTTCA CTCTCACCAT CAGCGACGTG
CAGTGTGACG ATGCTGCCAC TTATTACTGT CTGGGCGCCT ATGATTGTAG TGGTGTTGAT TGTAGTGCTT TCGGCGGAGG
GACCAAGGTG GTCGTCAAA
```

Heavy DNA
CA167_01083
(SEQ ID NO: 50)

```
CAGTCGGTGG AGGAGTCCGG GGGTCGCCTG GTCACGCCTG GGACACCCCT TGCACCGTCT CTGGATTCTC
CCTCAGTACC AATGCAATGA TCTGGGTCCG CCAGGCTCCA GGGAAGGGGC TGGAATATAT CGGTGTGATT GCTGGTAGTG
GTAGCACATC TTACGCGAGC TGGGCGAAAG GCCGATTCAC CATCTCCAAA ACCTCGACCA CGGTGGATCT GAAAATCACC
AGTCCGACAA CCGAGGACAC GGCCACCTAT TTCTGTGCCA GGTTAGTGGT CCGGAGAGCT TGTGGGCCA
AGGCACCCTC GTCACCGTCT CG
```

Light Protein
CA167_01083
(SEQ ID NO: 51)

```
AQVLTQTASP VSAAVGSTVI INCQASQSVY QNNYLAWFQQ KPGQPPKRLI YSASTLASGV SSRFKGSGSG TQFTLTISDV
QCDDAATYYC LGAYDCSGVD CSAFGGGTKV VVK
```

Figure 10 continued

Heavy Protein
CA167_01083
(SEQ ID NO: 52)

QSVEESGGRL VTPGTPLTLT CTVSGFSLST NAMIWVRQAP GKGLEYIGVI AGSGSTSYAS WAKGRFTISK TSTTVDLKIT
SPTTEDTATY FCARGGWVSG PESLWGQGTL VTVS

Light DNA
CA167_01084
(SEQ ID NO: 53)

GCCCAAGTGC TGACCCAGAC TCCATCTTCC ACGTCTGCAG CTGTGGGAGG CACAGTCACC ATCAGTTGCC AGTCCAGTCC
GAGTGTTTAT GGTAATAACT GGTTAGGCTG GTATCAGAAG AAACCAGGGC AGCCTCCCAA GCTCCTGATC TATTCTGCAT
CCACTCTGCG ATCTGGGGTC TCATCGCGGT TTAAAGGCAG TGGATCTGGG ACACAGTTCA CTCTCACCAT CAGCGACCTG
GAGTGTGACG ATGCTGCCAC TTACTACTGT GCAGGCGGTT ATAGTGGTAA TATTCATGTT TTCGGCGGAG GGACCAAGGT
GGTGGTCAAA

Heavy DNA
CA167_01084
(SEQ ID NO: 54)

CAGTCGGTGG AGGAGTCCGG GTCACGCCTG GTCACGCCTG GGACACCCCT GACACTCACC TGCACAGTCT CTGGATTCTC
CCTCAATAAC TACGACATGA CCTGGGTCCG CCAGGCTCCA GGGAAGGGGC TGGAATGGAT CGGAAGTATT TTTGTTAGTG
GTAATATATA CTACGCGAGC TGGGCGAAAG GCCGATTCAC CATCTCCAAA ACCTCGACCA CGGTGGATCT GAAAATGACC
AGTCCGACAA CCGAGGACAC GGCCACCTAT TTCTGTGCCA GAGCAATTCT TGGTAGTAGT AAGGGGTTGT GGGGCCCAGG
CACCCTGGTC ACCGTCTCG

Light Protein
CA167_01084
(SEQ ID NO: 55)

AQVLTQTPSS TSAAVGGTVT ISCQSSPSVY GNNWLGWYQK KPGQPPKLLI YSASTLASGV SSRFKGSGSG TQFTLTISDL
ECDDAATYYC AGGYSGNIHV FGGGTKVVVK

Heavy Protein
CA167_01084
(SEQ ID NO: 56)

QSVEESGGRL VTPGTPLTLT CTVSGFSLNN YDMTWVRQAP GKGLEWIGSI FVSGNIYYAS WAKGRFTISK TSTTVDLKMT
SPTTEDTATY FCARAILGSS KGLWGPGTLV TVS

Figure 11

Light DNA CA167_01085 (SEQ ID NO: 57)

```
GCCTATGATA TGACCCAGAC TCCAGCCTCT GTGGAGGTAG CTGTGGGAGG CACAGTCACC ATCAAGTGCC AGGCCAGTCA GAGCATTTAC
AGTATTTAG CCTGGTATCA GCAGAAACCA GGGCAGCCTC CCAAGCTCCT GATTTATTCT GCATCCTATC TAGCATCTGG GGTCCCATCG
CGGTTCAGCG GCAGTGGATC TGGGACAGAG TTCACTCTCA CCATCAGCGA CCTGGAGTGT GCCGATGCTG CCACTTATTA CTGTCAACAC
GGGTACATTA GTGGTAATGT TGATAATGCT TTCGGCGGAG GGACCAAGGT GGTCGTCAAA
```

Heavy DNA CA167_01085 (SEQ ID NO: 58)

```
CAGTCGGTGG AGGAGTCCGG GGGTCGCCTG GTCACGCCTG GGACACCCCT GACACTCACC TGCACAGTCT CCTGATTCTC CCTCAGCATC
TACGACATGA GCTGGGTCCG CAGGCTCCA CATCTCCAAA CATCCCAGGG TGGAATGGAT CGGATCCATT TATGTTAGTG CTACGGAGC
TGGGCGAAAG GCCGATTCAC ACCTCCAAA CATCCGACAA CGGTGGATCT GAAAATGACC AGTCCGACAA CCGAGGACAC GGCCACCTAT
TTCTGTGCCA GAGCGGTTCC TGGTAGTAGT AAGGGGTTGT GGGGCCAGG GACCCTCGTC ACCGTCTCG
```

Light Protein CA167_01085 (SEQ ID NO: 59)

```
AYDMTQTPAS VEVAVGGTVT IKCQASQSIY SYLAWYQQKP GQPPKLLIYS ASYLASGVPS RFSGSGSGTE FTLTISDLEC ADAATYCQH
GYISGNVDNA FGGGTKVVVK
```

Heavy Protein CA167_01085 (SEQ ID NO: 60)

```
QSVEESGGRL VTPGTPLTLT CTVSGFSLSI YDMSWVRQAP GKGLEWIGSI YVSGNIYYAS WAKGRFTISK TSTTVDLKMT SPTTEDTATY
FCARAVPGSS KGLWGQGTLV TVS
```

Light DNA CA167_01086 (SEQ ID NO: 61)

```
GCGCAAGTGC TGACCCAGAC TCCATCCCCT GTGTCTGCAG CCAAAGTCACC ATCAATTGCC AGTCCAGTCA GAGTATTTAT
ACTAACTACT TATCCTGGTA TCAGCAGAAA CCAGGACAGC CCTGATCTAT TCTGCATCCA CTCTGGCATC TGGGGTCCCA
TCGCGGTTCA AAGGCAGTGG ATCTGGGACA CAGTTCACTC TCACAATCAG CGAAGTACAG TGTGACGATG CTGCCACTTA CTACTGTCAA
GCCTATTTTA CTGGTGAGAT TTTTCCTTC GGCGGAGGGA CCAAGGTGGT CGTCAAA
```

Heavy DNA CA167_01086 (SEQ ID NO: 62)

```
CAGGAGCAAC TGAAGGAGTC CGGGGGAGGC CTGGTAACGC CTGACACTC ACCTGCACCG TCTCTGGATT CTCCCTCGAT
AACTACCACA TGGGCTGGGT CCGCCAGGCT CCGGCAGGCT CCAGGGAAGG GGCTCAATTA CATCGGATTC GTGGTACCAC ATACTACGCG
AGCTGGCGA AGGGCCGATT CACCATCTCC AAAAACCTCGA CCACGTCGA TCTGATGATC ACCAGTCCGA CAACGGGGA CACGGCCACC
TATTTCTGTG CCAGAGGAAG GGCCTTTACT TGTGGGGCC AGGCACCCTG GTCACCGTCT CG
```

Light Protein CA167_01086 (SEQ ID NO: 63)

```
AQVLTQTPSP VSAAVGGKVT INCQSSQSIY TNYLSWYQQK PGQPPRLLIY SASTLASGVP SRFKGSGSGT QFTLTISEVQ CDDAATYYCQ
AYFTGEIFPF GGGTKVVVK
```

Heavy Protein CA167_01086 (SEQ ID NO: 64)

```
QEQLKESGGG LVTPGGTLTL TCTVSGFSLD NYHMGWVRQA PGKGLNYIGF ITRGGTTYYA SWAKGRFTIS KTSTTVDLMI TSPTTGDTAT
YFCARGSSGAS GFYLWGPGTL VTVS
```

METHOD TO GENERATE ANTIBODIES TO ION CHANNELS

CROSS-REFERENCE TO RELATED APPLICATIONS

The present application is a continuation of application Ser. No. 13/523,104, filed Jun. 14, 2012, which is a continuation of application Ser. No. 13/504,259, filed Apr. 26, 2012, now U.S. Pat. No. 9,067,995, which issued on Jun. 30, 2015, which is the U.S. National Phase entry under U.S.C. § 371 of PCT International Application No. PCT/EP2010/066279, filed Oct. 27, 2010, which claims the benefit of priority under 35 U.S.C. § 119€ (1) of U.S. Provisional Application No. 61/255,202, filed Oct. 27, 2009, and under 35 U.S.C. § 119(a) of British Application No. 0922435.3, filed Dec. 22, 2009, all of which are incorporated herein by reference in their entirety.

The present disclosure relates to a method of generating anti-ion channel antibodies, in particular functionally modifying antibodies, employing cyclic peptides, and use of said peptides and compositions comprising the same for immunizing a host for generating said antibodies.

Ion channels are pore-forming proteins that help establish and control cell membrane potential of all living cells by allowing the flow of ions down their electrochemical gradient. They are present in the membranes that surround all biological cells. The human genome contains more than 400 ion channel genes presenting a large diversity and play critical roles in many cellular processes such as secretion, muscular contraction and the generation and propagation of action potentials in cardiac and neuronal tissues.

Ion channels are integral membrane proteins that may adopt large molecular structures based on the assembly of several proteins. Such "multi-subunit" assemblies usually involve an arrangement of identical or homologous proteins closely packed around a water-filled pore through the plane of the membrane or lipid bilayer. The pore-forming subunit(s), usually called the α-subunit, may be associated with auxiliary subunits, either membrane bound or cytosolic, that help to control activity and cell surface expression of the ion channel protein. The X-ray structure of various ion channels was recently resolved (Doyle et al. Science 280:69 (1998); Jiang et al., Nature 423:33 (2003); Long et al., Science 309:897 (2005)) and indicate that the organization of the pore structure is largely conserved among ion channel family members. The opening and closing of the ion channel pore, referred as the gating process, may be triggered by various cellular or biochemical processes.

The largest family of ion channel proteins is composed of voltage-gated channels including e.g. sodium, calcium and potassium ion channels, transient receptor potential ion channels hyperpolarization activated ion channels, inward rectifier ion channels, two-pore domain potassium channels and voltage gated proton channels. The latter depolarize in a pH-sensitive manner.

Inward rectifier ion channels are composed of 15 official and 1 unofficial members. The family can be further subdivided into 7 subfamilies based on homology.

At the present time there are about 10 voltage-gated calcium channels that have been identified.

Transient receptor potential ion channels are subdivided into 6 subfamilies based on homology: classical (TRPC), vanilloid receptors (TRPV), melastatin (TRPM), polycystins (TRPP), mucolipins (TRPML), and ankyrin transmembrane protein 1 (TRPA).

Hyperpolarization activated ion channels are sensitive to the cyclic nucleotides cAMP and cGMP, which alter the voltage sensitivity of the channel's opening. These channels are permeable to the monovalent cations $K^+$ and $Na^+$. There are 4 members of this family, all of which form tetramers of six-transmembrane α-subunits. As these channels open under hyperpolarizing conditions, they function as pacemaking channels in the heart, particularly the SA node.

The voltage-gated and ligand-gated ion channels are the most prominent members of the ion channel protein family. The activity of voltage-gated ion channels (e.g. calcium, sodium and potassium channels) is controlled by changes in cell membrane potentials whereas the ligand-gated ion channels (e.g. GABA-A receptors, Acetylcholine receptors) are controlled by the binding of specific intracellular or extracellular ligands. The gating mechanism is very complex, involving various membrane, pore and cytosolic structures, and differs between classes of ion channels.

Voltage-gated ion channels, sometimes referred to voltage-sensitive ion channels, are a class of transmembrane proteins that provide a basis for cellular excitability in cardiac and neuronal tissues. These channels are activated either by cell hyper- or depolarizations and generate ion fluxes that lead to control of cell membrane potential. Voltage-gated sodium channels are generally responsible for the initiation of action potentials whereas voltage gated potassium channels mediate cell membrane repolarization. The fine tuned interplay between various voltage-gated ion channels is critical for the shaping of cardiac and neuronal action potentials.

One class of voltage-gated sodium channels comprises nine different isoforms ($Na_v1.1$-$1.9$) and four different sodium channel specific accessory proteins have been described (SCN1b-SCN4b). The distinct functional activities of those isoforms have been described in a variety of neuronal cell types (Llinas et al., J. Physiol. 305:197-213 (1980); Kostyuk et al., Neuroscience 6:2423-2430 (1981); Bossu et al., Neurosci. Lett. 51:241-246 (1984) 1981; Gilly et al., Nature 309:448-450 (1984); French et al., Neurosci. Lett. 56:289-294 (1985); Ikeda et al., J. Neurophysiol. 55:527-539 (1986); Jones et al., J. Physiol. 389:605-627 (1987); Alonso & Llinas, 1989; Gilly et al., J. Neurosci. 9:1362-1374 (1989)) and in skeletal muscle (Gonoi et al., J. Neurosci. 5:2559-2564 (1985); Weiss et al., Science 233:361-364 (1986)). The $Na_v1.5$ and $Na_v1.4$ channels are the major sodium channel isoforms expressed in the cardiac and muscular tissue, respectively whereas $Na_v1.1$, 1.2, 1.3, 1.6, 1.7, 1.8 and 1.9 are specifically expressed in the central and peripheral nervous system. The use of the natural occurring toxin, tetrodotoxin (TTX), allowed to establish a pharmacological classification of the sodium channel isoforms based on their affinity to the toxin. The voltage-gated sodium channels were thus classified as TTX resistant ($Na_v1.5$, 1.8, 1.9) and TTX sensitive.

Certain ion channels have been associated with modulation of pain (see for example PNAS Nov. 6, 2001. vol 98 no. 23 13373-13378 and The Journal of Neuroscience 22, 2004 24(38) 832-836). The ion channel $Na_v1.7$ is believed to have the ability to modulate pain, such as neuropathic pain and thus is a particularly interesting target for therapeutic intervention. $Na_v1.8$ and $Na_v1.9$ are also thought to have a role in the modulation of pain.

$Na_v1.7$ is a voltage-activated, tetrodotoxin-sensitive sodium channel encoded by the gene SCN9A. Both gain-of-function and loss-of-function mutations of $Na_v1.7$ result in clear pain-related abnormalities in humans.

Originally, gain-of-function mutations in SCN9A were identified by linkage analysis as the cause of erythromelalgia (or primary erythermalgia) and paroxysmal extreme pain disorder (formerly familiar rectal pain). Erythromelalgia is a rare autosomal dominant disorder associated with bouts of burning pain together with heat and redness in the extremities. The complete inability to sense pain by an otherwise healthy individual, devoid of neuropathy, is a very rare phenotype. Very recently, two studies, reported by Cox et al (2006) and by Goldberg et al (2007), describe such a phenotype mapped, as an autosomal-recessive trait, to chromosome 2q24.3, a region containing the gene SCN9A. In both studies, detailed neurological tests revealed that these people are able to distinguish sharp/dull and hot/cold stimuli but have a global absence of pain sensation. All had injuries to lips and/or tongue caused by biting themselves. All had frequent bruises and cuts, and most suffered fractures or osteomyelitis.

This data constitutes strong evidence that SCN9A channelopathy, leading to loss of function of ion channel $Na_v1.7$, is associated with insensitivity to pain, in the absence of neuropathy or of cognitive, emotional or neurological disorders, and clinically validate $Na_v1.7$ as a pain-relevant target. Furthermore, from KO studies and animal pain models, it would appear that $Na_v1.7$ plays a major role in inflammatory pain.

FIG. 1a is a diagrammatic representation of an ion channel, such as $Na_v1.7$, which comprises four domains A, B, C and D (also referred to as domain I, II, III and IV). Each domain comprises 6 transmembrane protein helixes S1, S2, S3, S4, S5 and S6. The exact amino acid number of each transmembrane protein varies depending on the database entry employed but UniProtKB/Swiss-Prot provides the following information for $Na_v1.7$:

in domain A transmembrane protein S1, S2, S3, S4, S5 and S6 are assigned amino acids 122-145, 154-173, 187-205, 212-231, 248-271 and 379-404, respectively; in domain B transmembrane protein S1, S2, S3, S4, S5 and S6 are assigned amino acids 739-763, 775-798, 807-826, 833-852, 869-889 and 943-968 respectively;

in domain C transmembrane protein S1, S2, S3, S4, S5 and S6 are assigned amino acids 1188-1211, 1225-1250, 1257-1278, 1283-1304, 1324-1351 and 1431-1457 respectively; and in domain D transmembrane protein S1, S2, S3, S4, S5 and S6 are assigned amino acids 1511-1534, 1546-1569, 1576-1599, 1610-1631, 1647-1669 and 1736-1760, respectively.

There are a number of natural variations of the sequence that are available in public databases, for example see UniProtKB/Swiss-Prot Q15858.

In the present disclosure S1, S2, S3, S4, S5 and S6 refers to the entities described above or a entity corresponding to same in an alternative ion channel, including wherein a different amino acid assignment is given to the same and including the corresponding entity in natural or non-natural variants and different isotypes of the same.

Each domain also contains extra-cellular hydrophilic loops E1, E2 and E3. The amino acid sequence of E1 in each domain starts after the transmembrane region S1 and ends at S2. E1 in each domain is distinct from E1 in other domains. The amino acid sequence of E2 in each domain starts after the transmembrane region S3 and ends at S4. E2 in each domain is distinct from E2 in other domains. The amino acid sequence of E3 in each domain starts after the transmembrane region S5 and ends at S6. E3 in each domain is also distinct from E3 in other domains.

Whilst the $Na_v$ and $Ca_v$ ion channels comprise four domains, A, B, C and D, each containing six transmembrane protein helixes, other ion channels, such as $K_v$ ion channels, HCN ion channels and TRP ion channels comprise one domain. As for each domain in the $Na_v$ and $Ca_v$ ion channels, the $K_v$ ion channels, HCN ion channels and TRP ion channels comprise 6 transmembrane protein helixes S1, S2, S3, S4, S5 and S6 and three extra-cellular hydrophilic loops E1, E2 and E3 as described above.

In a $Na_v1.7$ ion channel, the extracellular loops (E loops) are the following amino acid residues of SEQ ID NO:69 in FIG. 1c:

| $Na_v1.7$ Domain | E1 amino acids | E2 amino acids | E3 amino acids |
|---|---|---|---|
| A | 146-153 | 206-211 | 272-378 |
| B | 764-774 | 827-832 | 890-942 |
| C | 1212-1224 | 1279-1282 | 1352-1430 |
| D | 1535-1545 | 1600-1609 | 1670-1735 |

The extracellular loops in some domains of $Na_v1.7$ share similarities with extracellular loops found in other ion channels.

$Na_v1.7$ is expressed in the peripheral nervous system i.e. in nociceptive dorsal root ganglions (DRG), most notably in nociceptive small-diameter DRG neurons, with little representation in the brain. $Na_v1.7$ distribution (e.g. sensory ending) and physiology predispose it to a major role in transmitting painful stimuli.

The expression of $Na_v1.7$ in the peripheral nervous system makes it a very attractive target for the generation of function blocking antibodies which represent an innovative approach for valuable treatment for pain with no side-effects or minimizing side effects to a tolerable level.

Neuropathic pain is a highly prevalent condition. In the United States, it is estimated to affect between 0.6 and 1.5% of the population, or 1.8 to 4.5 million people. (Pullar and Palmer, 2003). At least 1.4 million people each year are diagnosed with painful diabetic neuropathy (PDN), postherpetic neuropathy (PHN) or trigeminal neuralgia (TN)—three major causes of neuropathic pain. Other causes of neuropathic pain include spinal cord injuries, multiple sclerosis, phantom limb pain, post-stroke pain and HIV-associated pain. If patients with neuropathic-related chronic back pain, osteoarthritis and cancer were included, the total number would at least double. Nonsteroidal anti-inflammatory drugs (NSAIDs) although frequently used, are not very effective in the treatment of neuropathic pain. Moreover, their chronic use may lead to serious gastric damage. On the other hand, the use of opioids (morphine and derivatives) is restricted to the most severe form of neuropathic pain, i.e., cancer-related neuropathy, because serious side-effects are associated with chronic treatment, such as nausea, emesis, respiratory depression, constipation and tolerance, and the potential for addiction and abuse. The latter have prevented the use of opioids in other neuropathies (Dellemijn, 1999; Namaka et al., 2004). Anti-epileptic drugs (AEDs) are known to attenuate abnormal neural hyperexcitability in the brain. In view of neural hyperexcitability playing a crucial role in neuropathic pain, it is understandable that AEDs were aimed at the treatment of chronic neuropathic pain (Renfrey, Downton and Featherstone, 2003). The most recent and important examples are gabapentin (Neurontin) and pregabalin (Lyrica, Frampton and Scott, 2004). However, even gabapentin, the gold standard for the treatment of neuropathic pain, reduces pain at best by 50% in about 40% of patients (Dworkin, 2002). Further, in contrast to opioids, gabapentin is not used in the treatment of cancer-related neuropathic pain.

As stated above, $Na_v1.7$ 'loss of function' mutation in human leads to insensitivity to pain (Cox et al., 2006). Moreover, $Na_v1.7$ 'gain of function' mutation in human leads to the pain phenotypes erythromelalgia and paroxysmal extreme pain disorder (Dib-Hajj, Yang, Waxman, 2008). Additionally, a peripherally acting small molecule blocking $Na_v1.7$ reverses hyperalgesia and allodynia in rat models of inflammatory and neuropathic pain (McGowan et al., 2009). Therefore a peripherally acting $Na_v1.7$ blocking antibody should be beneficial for pain therapy.

To date potent chemical inhibitors of ion channels have been identified but generally these are characterised by a poor selectivity against other ion channel isoforms. Given the ubiquitous distribution of ion channels in living organisms these non-selective inhibitors have been of limited utility.

It is clear from the discussion above that ion channels represent therapeutic targets of significant interest. It would be useful to have optimized techniques for generating therapeutic antibodies to these targets.

The present inventors have now found that anti-ion channel antibodies, for example functionally modifying antibodies, can be readily prepared even using short peptide sequence by employing peptides in a cyclised form for immunization.

SUMMARY OF THE INVENTION

Thus in one aspect the invention provides a method for generating a functionally modifying antibody to an ion channel comprising immunizing a host with a cyclic peptide comprising an extracellular sequence of said ion channel.

BRIEF DESCRIPTION OF THE DRAWINGS

FIG. 1b shows the amino acid sequence for domain A (SEQ ID NO: 65), B (SEQ ID NO: 66), C (SEQ ID NO: 67) and D (SEQ ID NO: 68) of $Na_v1.7$ FIG. 1c shows the full amino acid sequence of Nav1.7 (SEQ ID NO: 69)

FIG. 3e (b) shows automated Patch Clamp analysis of recombinant human Nav1.7 channels expressed in HEK cells. 1080 monoclonal antibody produces a dose-dependent inhibition of Nav1.7 currents.

FIGS. 6 to 11 show various antibody sequences.

Figure 1A:
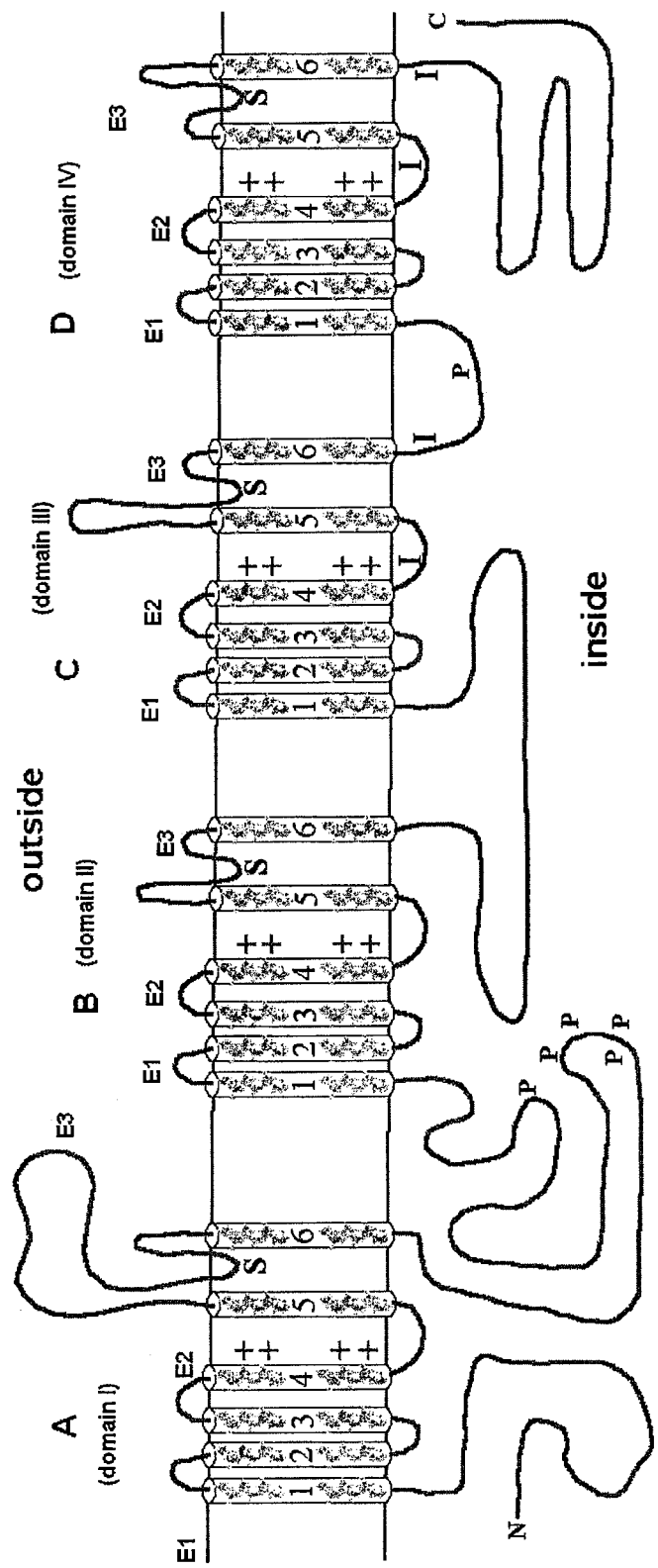
FIG. 1a shows a diagrammatic representation of Nav1.7.

Surprisingly, relatively short peptides from ion channels are immunogenic in hosts when they are cyclised. In one embodiment the peptide comprises between 5 and 30, for example 5, 6, 7, 8, 9, 10, 11, 12, 13, 14, 15, 16, 17, 18, 19, 20, 21, 22, 23, 24, 25, 26, 27, 28, 29 or 30 amino acids.

An extracellular sequence of an ion-channel as employed herein is at least for four, such as five or more consecutive tandem amino acids from an extracellular loop or region of the relevant ion channel.

In one aspect the anti-ion channel antibody is specific.

Specific as employed herein is intended to refer to the fact that the antibody is selective for the ion channel to which it is specific and can distinguish it from other ion channels and proteins, for example other ion channels in the same family. A selective antibody is one that, for example can be used to affinity purify the relevant ion channel including from other ion channels.

In one example, suitable peptides for use in the present invention may be designed by comparing the amino acid sequence of the selected ion channel to other family members to identify unique residues specific for the given ion channel of interest. Particular regions of interest such as the extracellular domains may be used in such a comparison. Cyclic peptides can then be designed based on the unique residues identified. Preferably the cyclic peptide contains at least one unique residue for the ion channel of interest. In this context unique refers to an amino acid residue which is specific for the ion channel of interest when the amino acid sequence of that ion channel is compared to at least one other, preferably all other family members for which sequences are available. In one embodiment the cyclic peptide contains two unique residues. In one embodiment the cyclic peptide contains three or four or five or six or seven or eight or nine or ten or eleven or twelve unique residues.

If a cross-reactive antibody is desired ie. an antibody which binds to more than one ion channel peptides may be designed which contain residues specific to the two or more selected ion channels, again by comparison to other family members.

If desired, Kyte Doolittle plots may be used to support the choice of peptide used. By employing a Kyte Doolittle plot it is possible to determine which peptides will comprise the highest number of the most hydrophilic residues i.e. those which are more likely to be solvent exposed.

In one example the unique residue(s) are away from the site of conjugation.

In one example unique residues for Nav1.7 are identified by amino acid sequence alignment with other available family members, i.e Nav1.1, Nav 1.2, Nav 1.3, Nav 1.4, Nav 1.5, Nav 1.6, Nav 1.8 and Nav 1.9.

The following Nav1.7 residues are unique to Nav1.7 compared to other family members i.e Nav1.1, Nav 1.2, Nav 1.3, Nav 1.4, Nav 1.5, Nav 1.6, Nav 1.8 and Nav 1.9: N146, F276, S279, L280, E281, L286, M290, N291, T292, L293, S295, E296, D298, F299, R300, K301, F317, T319, T329, 1333, K773, R1218, I1224, S1357, P1360, A1361, Q1363, P1365, R1367, F1371, S1377, N1379, L1385, T1409, I1410, V1419, K1423, K1536, E1537, G1538, H1542, E1545, T1601, D1673, N1676, K1718 and E1727. Accordingly, a suitable peptide of Nav1.7 for use in the present invention comprises at least one of the following residues in the peptide sequence: N146, F276, S279, L280, E281, L286, M290, N291, T292, L293, S295, E296, D298, F299, R300, K301, F317, T319, T329, 1333, K773, R1218, I1224, S1357, P1360, A1361, Q1363, P1365, R1367, F1371, S1377, N1379, L1385, T1409, I1410, V1419, K1423, K1536, E1537, G1538, H1542, E1545, T1601, D1673, N1676, K1718 and E1727.

A cyclic peptide as employed herein is a peptide where a sequence of amino acids are joined by a bond, such as a disulfide bond or amide bond, thereby forming a loop or circle with no discernable start and/or finish. The cyclic peptide may be formed from a corresponding linear peptide by various means such as, but not limited to, the following: C-terminal carboxyl group ligation to the N-terminal alpha amino group to form a peptide bond; alternatively side chain carboxyl groups (of aspartic or glutamic acid residues) may be ligated to the side chain amino group of lysine or the N-terminal alpha amino group or the C-terminal carboxyl group may be ligated to the side chain amino group of lysine; disulphide bond formation between side chains thiols of two cysteine residue separated from each other by at least three residues in the linear sequence. It may be desirable to form the "ring completing bond" in an area of overlap in the linear sequence. Area of overlap as employed herein is intended to refer to where there is a repeat of two or more amino acids occurring in the sequence. Thus a sequence of overlap as employed herein is intended to refer to where there is some commonality in the sequence, for example at least two, such as 3 or 4 amino acids are located in the same order in the sequence in two separate locations. These regions of overlap can be aligned and ligated such that an amino acid in one location replaces the corresponding amino acid in the second location to form the cyclised peptide.

Thus in one embodiment the peptide is cyclised by forming an amide bond. In one embodiment the peptide is cyclised by forming a disulfide bond.

In one embodiment the sequence is ligated in a region of overlap in the linear sequence.

Cyclic peptides may be synthesized using any suitable method known in the art. In one embodiment the cyclic peptide is synthesized using protecting groups to prevent reactions of the amino acid side chains (Barlos, K.; Gatos, D.; Kutsogianni, S.; Papaphotiou, G.; Poulos, C.; Tsegenidis, T. Int. J. Pept. Protein Res. 1991, Vol 38, Issue 6 p 562-568) followed by cyclization and removal of the protecting groups (Kessler H et al., 1989, Computer Aided Drug Design, p 461-484; Dekker M et al, 1990, J. Peptide Research, 35, p 287-300; Gurrath M. et al., 1992, Eur. J. Biochem., 210, 911-921; Izumiya N. et al., 1981, Biopolymers, 20, 1785-1791; Brady S. F. et al., 1983, in Peptides, Structure and Function, Proceedings of the Eighth American Peptide Symposium, Ed. V. J. Hruby and D. H. Rick, pp. 127-130, Pierce Chemical Company, Rockford, Ill.; He J. X. et al., 1994, Lett. Peptide Sci., 1, 25-30).

In one embodiment the cyclic peptide employed for immunization is derived from the amino acid sequence of an E1 region, an E2 region, an E3 region or a combination thereof.

In one embodiment, wherein the ion channel comprises A, B, C and D domains such as in the sodium ion channels $Na_v$ 1.1, 1.2, 1.3, 1.4, 1.5, 1.6, 1.7, 1.8 and 1.9, the cyclic peptide employed for immunization is derived from the sequence of the domain A (also referred to as I), domain B (also referred to as II), domain C (also referred to III), domain D (also referred to as IV) or a combination thereof.

In one embodiment the ion channel against which antibodies are raised is a sodium ion channel, for example $Na_v$ 1.1, 1.2, 1.3, 1.4, 1.5, 1.6, 1.7, 1.8 or 1.9. The cyclic peptide employed for immunization may comprise at least part of an extracellular sequence of the ion channel wherein the extracellular sequence is the E1 region, E2 region or E3 region and may be derived from the A domain, B domain, C domain or D domain of the ion channel. In a preferred embodiment the cyclic peptide comprises at least a part of an E1 or E3 extracellular region derived from the A domain, B domain, C domain or D domain of the ion channel. In a further preferred embodiment the cyclic peptide comprises at least a part of an E1 or E3 extracellular region derived from the A domain or the B domain of the ion channel. Preferably the cyclic peptide comprises at least a part of the AE3 extracellular region or the BE1 extracellular region.

In one embodiment the ion channel against which antibodies are raised is one with a function in the modulation of pain. Ion channels thought to be involved and/or associated with modulation of pain include but are not limited to $Na_v$ 1.3, $Na_v$ 1.6, $Na_v$ 1.7, $Na_v$ 1.8, $Na_v$ 1.9, $Ca_v$ 3.1, Ca 3.2, $Ca_v$ 3.3, $Ca_v$ 2.1, $Ca_v$ 2.2, $Ca_v$ 2.3, $K_v$ 2.1, $K_v$ 2.2, $K_v$ 7.x, HCN1, HCN2, TRPV1, TRPA1, ASIC1, TRPM8, TRPV3 and TRP4.

In one embodiment the ion channel against which antibodies are raised is a sodium channel, for $Na_v$1.7, $Na_v$1.8 or $Na_v$1.9, such as a $Na_v$1.7.

In one embodiment the ion channel against which antibodies are raised is a potassium ion channel $K_v$ 2.1, $K_v$ 2.2 or $K_v$ 7.x.

In one embodiment the ion channel against which antibodies are raised is a calcium ion channel, for example $Ca_v$ 3.1, $Ca_v$ 3.2, $Ca_v$ 3.3, $Ca_v$ 2.1, $Ca_v$ 2.2 or $Ca_v$ 2.3.

In one embodiment the ion channel against which antibodies are raised is a hyperpolarisable channel HCN1 or HCN2.

In one embodiment the ion channel against which antibodies are raised is a non-gated ion channel, for example TRPV1, TRPA1, ASIC1, TRPM8, TRPV3 or TRP4.

In one embodiment the ion channel against which antibodies are raised is a potassium channel, for example $K_v$3.1 or 3.2.

$Na_v$1.7

In one embodiment the cyclic peptide comprises 5 or more consecutive amino acid residues from one or more of the following $Na_v$ 1.7 sequences, wherein the domain A, B, C or D and the extracellular loop E1, E2 or E3, from which the peptide is derived is denoted in brackets:

```
(AE1)
                                (SEQ ID NO: 71)
TMNNPP (AE3)
                                (SEQ ID NO: 72)
CFRNSLENNETLESIMNTLESEEDFRKY, (AE3)
                                (SEQ ID NO: 73)
EGSKDA, (AE3)
                                (SEQ ID NO: 74)
GFSTDSGQ,
```

(BE1)
HPMTEEFKN, (SEQ ID NO: 75)

(BE3)
NDDCTLP, (SEQ ID NO: 76)

(CE1)
IERKKTIKI, (SEQ ID NO: 77)

(CE3)
CINTTDGSRFPASQVP, (SEQ ID NO: 78)

(CE3)
NRSECFALM, (SEQ ID NO: 79)

(CE3)
NVSQNVR, (SEQ ID NO: 80)

(CE3)
SVNVDKQP, (SEQ ID NO: 81)

(DE1)
EKEGQSQHMTE, (SEQ ID NO: 82)

(DE3)
KKEDGIND, (SEQ ID NO: 83)
and/or (DE3)
CDPKKVHP. (SEQ ID NO: 84)

In one embodiment the cyclised peptide contains a single cysteine residue linking the N-terminal to the C-terminal. For example is selected from the following sequences, wherein the domain A, B, C or D and the extracellular loop E1, E2 or E3, from which the peptide is derived is denoted in brackets. The cysteines which are underlined in selected peptides are non-naturally occurring cysteine residues in the ion channel. The naturally occurring or non-naturally occurring cysteine residues in the following peptides may be used to attach a carrier protein.

(AE1)
CTMNNPP, (SEQ ID NO: 85)

(AE3)
CFRNSLENN, (SEQ ID NO: 86)

(AE3)
CTLESIMNTLESEEDFRKY, (SEQ ID NO: 87)

(AE3)
CEGSKDA, (SEQ ID NO: 88)

(AE3)
CFSTDSGQ, (SEQ ID NO: 89)

(BE1)
CPMTEEFKN, (SEQ ID NO: 90)

(BE3)
DDCTLPRWHMN, (SEQ ID NO: 91)

(CE1)
CIERKKTIKI, (SEQ ID NO: 92)

(CE3)
CINTTDGSRFPASQVP, (SEQ ID NO: 78)

(CE3)
NRSECFALM, (SEQ ID NO: 79)

(CE3)
CNVSQNVR, (SEQ ID NO: 93)

(CE3)
VNVDKQPC (SEQ ID NO: 94)

(DE1)
CEKEGQSQHMTE, (SEQ ID NO: 95)
and/or (DE3)
KKEDGINDC. (SEQ ID NO: 96)

Other Na$_v$1.7 cyclic peptides suitable for use in generating function modifying antibodies to the extracellular domains of the stated ion channels are listed below, wherein the domain A -continued AE3.3
cyclic[cys*FSTDSGQ] (SEQ ID NO: 89)

AE3.4
cyclic[cys*EGSKDA] (SEQ ID NO: 88)

BE3.1
cyclic[cys*KINDD] (SEQ ID NO: 101)

BE3.2
cyclic[cys*TLPRWHMNDD] (SEQ ID NO: 102)

CE3.1
cyclic[cys*INTTDGSRFPASQVPNRSE] (SEQ ID NO: 103)

CE3.2
cyclic[cys*NVSQNVR] (SEQ ID NO: 93)

CE3.3
cyclic[cys*VNVDKQP] (SEQ ID NO: 94)

DE3.1
cyclic[homocys*KKEDGIND]
or
cyclic[cys*KKEDGIND] (SEQ ID NO: 96)

DE3.2
cyclic[cys*DPKKVHP] (SEQ ID NO: 84)

In one embodiment of the present invention the cyclic peptide has an amino acid sequence selected from the group consisting SEQ ID NOs: 71 to 103. In a preferred embodiment, the cyclic peptide has an amino acid sequence selected from the group consisting of SEQ ID NO: 87, SEQ ID NO: 90, SEQ ID NO: 92 and SEQ ID NO: 102.

$K_v3.2$

In one embodiment there is provided the following cyclic peptides useful in generating anti-$K_v3.2$ antibodies:

CKNKTEPVINGTSPVLQYEIETD (SEQ ID NO: 104)

CRVGAQPNDPSASEHTQ (SEQ ID NO: 105)

Other cyclic peptides suitable for use in generating function modifying antibodies to the extracellular domains of the ion channels $Na_v1.3$, $Na_v1.8$ and $Na_v1.9$ are listed below, wherein the domain A, B, C or D and the extracellular loop E1, E2 or E3, from which the peptide is derived is denoted for each peptide before the sequence and wherein the cys* or homocys* in each peptide denotes that the cysteine or homocysteine may be coupled to a macromolecular carrier, such as a carrier protein, via maleimide chemistry:

Nav1.3

AE1.1
cyclic[cys*TLSNPP] (SEQ ID NO: 106)

-continued

Nav1.3

DE1.1
cyclic[homocys*TDDQGKY]
or
cyclic[cys*TDDQGKY] (SEQ ID NO: 107)

AE3.1
cyclic[cys*DSAFETNTT] (SEQ ID NO: 108)

AE3.2
cyclic[cys*TMSTFNWKD] (SEQ ID NO: 109)

BE3.1
cyclic[cys*KINDD] (SEQ ID NO: 110)
N.B. cross reactive with Nav1.7

CE3.1
cyclic[cys*VNMTTGNMFDISD] (SEQ ID NO: 111)

CE3.2
cyclic[cys*QALGKQAR] (SEQ ID NO: 112)

CE3.3
cyclic[cys*RDVKLQP] (SEQ ID NO: 113)

Accordingly, in one embodiment of the present invention the ion channel is $Na_v1.3$ and the cyclic peptide has an amino acid sequence selected from the group consisting of SEQ ID NOs: 106 to 113.

Nav1.8

AE1.1
cyclic[cys*MTRTDLPEK] (SEQ ID NO: 114)

BE1.1
cyclic[cys*GMSPTFEA] (SEQ ID NO: 115)

BE1.2
cyclic[cys*PMTDAFDA] (SEQ ID NO: 116)

BE1.3
cyclic[homocys*MEHHGMSPTFEA]
or
cyclic[cys*MEHHGMSPTFEA] (SEQ ID NO: 117)

BE1.4
cyclic[cys*MEHYPMTDAFDA] (SEQ ID NO: 118)

CE1.1
cyclic[cys*DQKPTVK] (SEQ ID NO: 119)

CE1.2
cyclic[cys*EEKPRVK] (SEQ ID NO: 120)

DE1.1
cyclic[cys*QSEEKTK] (SEQ ID NO: 121)

| Nav1.8 | |
|---|---|
| DE1.2<br>cyclic[cys*DDQSEEK] | (SEQ ID NO: 122) |
| DE1.3<br>cyclic[cys*DNQSEEK] | (SEQ ID NO: 123) |
| AE3.1<br>cyclic[cys*VKNDMAVNK] | (SEQ ID NO: 124) |
| AE3.2<br>cyclic[cys*IKNGTDPHK] | (SEQ ID NO: 125) |
| AE3.3<br>cyclic[cys*TNYSSHRK] | (SEQ ID NO: 126) |
| AE3.4<br>cyclic[cys*DNLSSEMA] | (SEQ ID NO: 127) |
| BE3.1<br>cyclic[cys*APHEDWPR] | (SEQ ID NO: 128) |
| BE3.2<br>cyclic[cys*VWNGERLR] | (SEQ ID NO: 129) |
| CE3.1<br>cyclic[cys*INYTDGEFS] | (SEQ ID NO: 130) |
| CE3.2<br>cyclic[cys*VDTRSNPFS] | (SEQ ID NO: 131) |
| CE3.3<br>cyclic[cys*KIQNSTGS] | (SEQ ID NO: 132) |
| CE3.4<br>cyclic[cys*YNQNNTGH] | (SEQ ID NO: 133) |

Accordingly in one embodiment of the present invention the ion channel is $Na_v1.8$ and the cyclic peptide has an amino acid sequence selected from the group consisting of SEQ ID NOs: 114 to 133.

| Nav1.9 | |
|---|---|
| AE1.1<br>cyclic[cys*TGPAKNSNSNN] | (SEQ ID NO: 134) |
| AE1.2<br>cyclic[homocys*ATGPAKNSNSNNTD]<br>or<br>cyclic[cys*ATGPAKNSNSNNTD] | (SEQ ID NO: 135) |
| BE1.1<br>cyclic[cys*EASFEK] | (SEQ ID NO: 136) |
| BE1.2<br>cyclic[cys*EHHKMEASFEK] | (SEQ ID NO: 137) |
| CE1.1<br>cyclic[cys*ENQPKIQE] | (SEQ ID NO: 138) |
| DE1.1<br>cyclic[cys*ESYNQPKAMKS] | (SEQ ID NO: 139) |
| DE1.2<br>cyclic[cys*YNQPKAMK] | (SEQ ID NO: 140) |
| AE3.1<br>cyclic[cys*KNISNPEAYDH] | (SEQ ID NO: 141) |
| AE3.2<br>cyclic[cys*FEKKENSPEFKM] | (SEQ ID NO: 142) |
| AE3.3<br>cyclic[cys*GIWMGNSA] | (SEQ ID NO: 143) |
| AE3.4<br>cyclic[cys*SIQYE] | (SEQ ID NO: 144) |
| AE3.5<br>cyclic[cys*KHTKIN] | (SEQ ID NO: 145) |
| BE3.1<br>cyclic[cys*NSQKSPKL] | (SEQ ID NO: 146) |
| BE3.2<br>cyclic[cys*NPTGPTVS] | (SEQ ID NO: 147) |
| CE3.1<br>cyclic[cys*INGTD] | (SEQ ID NO: 148) |
| CE3.2<br>cyclic[cys*NKSQ] | (SEQ ID NO: 149) |
| CE3.3<br>cyclic[cys*ESGNFS] | (SEQ ID NO: 150) |
| CE3.4<br>cyclic[cys*TEKEQQPEFE] | (SEQ ID NO: 151) |
| DE3.1<br>cyclic[cys*NSSSKES] | (SEQ ID NO: 152) |

Accordingly, in one embodiment of the present invention the ion channel is $Na_v1.9$ and the cyclic peptide has an amino acid sequence selected from the group consisting of SEQ ID NOs: 134 to 152.

HCN1 and HCN2

In one embodiment of the present invention the ion channel is HCN1 or HCN2 and the cyclic peptide has an amino acid sequence selected from the group consisting of SEQ ID NOs: 153 to 158 as follows, wherein the extracellular loop E1, E2 or E3, from which the peptide is derived is denoted for each peptide before each sequence and wherein the cys* or homocys* in each peptide denotes that the cysteine or homocysteine may be coupled to a macromolecular carrier, such as a carrier protein, via maleimide chemistry:

```
HCN1E1.1
                                        (SEQ ID NO: 153)
cyclic[cys*TEQTTT]

HCN1E3.1
                                        (SEQ ID NO: 154)
cyclic[cys*QDFPPD]

HCN1E3.2
                                        (SEQ ID NO: 155)
cyclic[cys*LNEMVND]

HCN2E1.1
                                        (SEQ ID NO: 156)
cyclic[cys*KDETTA]

HCN2E3.1
                                        (SEQ ID NO: 157)
cyclic[cys*QDFPRN]

HCN2E3.2
                                        (SEQ ID NO: 158)
cyclic[cys*INGMVNH]
```

In one embodiment a mixture of peptide antigens from one or more (such as one) ion channel(s) are employed for immunizing a host.

In one embodiment the cyclic peptide is designed to contain a single unique functional group for covalent attachment to a macromolecular carrier such as a xenogenic protein. The single unique functional group may be a cysteine, aspartate, glutamate or lysine residue. The unique functional group may be incorporated by an additional residue (either natural or non-natural amino acid) e.g. a cysteine, to allow specific coupling.

In one embodiment a biotin linker and carrier proteins may be attached via cysteine side chain.

To prepare immunogens for the purpose of raising anti-ion channel antibodies in a host animal each peptide requires covalent conjugation to a carrier protein. The carrier protein is selected on the basis of its loreigness' to the host species; thus for immunization of rabbits or rodents examples of suitable carrier proteins are keyhole limpet hemocyanin (KLH), ovalbumin (OVA) and bovine serum albumun (BSA). Each of the above peptides, may be conjugated through the cysteine thiol to one of each of the above proteins, where the lysine side chain amino groups of the latter have been covalently modified with a maleimide functionality to yield respectively:

KLH-maleimide,
Ovalbumin-maleimide, or
BSA-maleimide.

The present disclosure explicitly envisages each one of the peptides described herein in separate conjugations with each one of the carriers listed above, thus in the case of Na$_v$1.7, 99 different molecules are specifically provided for immunizing a host to provide function modifying anti-Nav1.7 antibodies, for example KLH-CEKEGQSQHMTE (cyclic) (SEQ ID NO: 95) or BSA-CEKEGQSQHMTE (cyclic) (SEQ ID NO: 95). Accordingly, any of the cyclic peptides having an amino acid sequence selected from SEQ ID NOs: 71 to 158 may be conjugated with each of the carrier proteins listed above.

As described above, the carrier protein may be conjugated through a unique functional group such as a cysteine residue. However, any alternative naturally occurring or non-naturally occurring residue may be used in place of a cysteine residue in order to conjugate the cyclic peptide to the carrier protein. An example of a non-naturally occurring residue which may be used in place of cysteine is a homocysteine residue, which is a homologue of cysteine which further comprises an additional methylene group in the side chain. Accordingly, any of the cyclic peptides having an amino acid sequence selected from SEQ ID NOs: 71 to 158, which comprise a cysteine residue may be modified to replace the cysteine residue with an alternative suitable naturally occurring or non-naturally occurring residue for conjugation to the carrier protein, such as a homocysteine residue.

The present disclosure also extends to novel peptides disclosed herein and compositions comprising same.

Generally between 0.001 and 1 mg of each peptide-carrier protein are required for each immunization dose per host animal.

Alternative immunogens suitable for raising function modifying antibodies include: full length human ion channels, truncations thereof including individual sub-domains and truncations of sub-domains; chimeric molecules with regions of ion channel fused to regions other transmembrane proteins to aid expression or present extracellular loops to the immune system and mutations of ion channels to constrain regions of the ion channel in a desired conformation.

These immunogens may be expressed in mammalian cells for direct cell immunization or purification of protein for immunization.

These immunogens may be expressed in *E. coli* or cell-free expression systems for purification of protein for immunization.

Purified protein may be integrated into lipid vesicles for immunisation.

These ion channel versions may also be generated as lipoparticles for immunization.

Thus in one aspect there is provided a method of generating antibodies in a host by immunizing, for example with at least one ion channel cyclic peptide-carrier protein conjugate or several different peptides (wherein at least one is cyclic) conjugated separately or as a mixture conjugated to the same carrier protein.

In one embodiment the method involves one, two, three, four or five immunizations.

In one embodiment the method involves at least two, such as two or three immunizations with the respective conjugates peptide(s).

In one embodiment the second immunization employs a different conjugate, wherein the peptide(s) is (are) common but the carrier protein is different to the carrier protein employed in the first immunization.

Thus in one embodiment the third immunization employs a different conjugate wherein the peptide(s) is (are) common to that of the first and second immunization, but the carrier protein is different to that employed in the first and/or second immunization. Unwanted antibody specificities against the carrier protein may in this way be minimized.

Suitable carrier protein combinations for sequential immunization include, KLH and Ovalbumin and BSA in any order.

Varying the carrier may be advantageous in optimizing the response to the peptide.

Each immunization will generally also include the administration of an adjuvant to stimulate immune responses. Suitable adjuvants include Freud's complete or incomplete adjuvant, and adjuvants comprising, alum, QS21, MPL and/or CPG.

The method may further comprise a step of separating antibodies or antibody producing cells from the host.

In one embodiment the host is a mouse, rat, shark, rabbit, pig, hamster, camel, llama, goat or human, in particular a rabbit.

Generally a adjuvant is administered as part of immunizing the host to stimulate the immune response to the peptide antigen.

Suitable adjuvants are well known to those in the art and include Freud's complete or incomplete adjuvant. Compositions comprising a saponin, for example such as QS21 and/or a MPL and/or CPG may also be suitable for use as adjuvants, see for example WO00/062800.

Combinations of MPL and alum may also be employed.

The adjuvant may be administered concomitantly with the antigen, for example in admixture with the peptide antigen or may be administered sequentially as a separate formulation.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93(15):7843-78481; WO92/02551; WO2004/051268 and International Patent Application number WO2004/106377.

Screening for antibodies can be performed using assays to measure binding. An example of a binding assay is an ELISA, in particular, employing a conjungated secondary antibody to detect anti-ion channel antibody. An example of a blocking assay is a flow cytometry based assay where a fluorescently labelled secondary antibody is used to detect the amount of binding to the cell.

One aspect there is provided an antibody or fragment thereof identified employing the present method. The present invention also provides an isolated DNA sequence encoding the heavy and/or light chain(s) of an antibody molecule identified by a method of the present invention. Sutiably, the DNA sequence encodes the heavy or the light chain of an antibody molecule of the present invention. The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences. In one embodiment the method comprises the further step of preparing DNA encoding an antibody or fragment according to the present disclosure.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

The present invention also relates to a cloning or expression vector comprising one or more DNA sequences of the present invention. Accordingly, provided is a cloning or expression vector comprising one or more DNA sequences encoding an antibody of the present invention. Suitably, the cloning or expression vector comprises two DNA sequences, encoding the light chain and the heavy chain of the antibody molecule of the present invention, respectively.

In one example the vector comprises an intergenic sequence between the heavy and the light chains, such as IGS2 (see WO03/048208).

In one aspect the invention comprises the further step of preparing a cloning or expression containing said DNA.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example E. coli, and other microbial systems may be used or eukaryotic, for example mammalian, host cell expression systems may also be used. Suitable mammalian host cells include CHO, myeloma or hybridoma cells.

Thus in one embodiment the method of the present disclosure comprises the step of preparing a suitable host for expressing antibody or fragment as described herein.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The antibodies and fragments according to the present disclosure are expressed at good levels from host cells. Thus the properties of the antibodies and/or fragments are optimised and condusive to commercial processing.

In one embodiment the method comprises the further step of preparing a humanized or chimeric antibody.

Humanised antibodies (which include CDR-grafted antibodies) are antibody molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

Chimeric antibodies are composed of elements derived from two different species such that the elements retain the characteristics of the species from which it is derived. Generally a chimeric antibody will comprise a variable region from one species, for example a mouse, rat, rabbit or similar and constant region from another species such as a human.

When the CDRs are grafted, any appropriate acceptor variable region framework sequence may be used having regard to the class/type of the donor antibody from which the CDRs are derived, including rat, rabbit, mouse, primate and human framework regions. Preferably, the CDR-grafted antibody of the present invention has a variable domain comprising human acceptor framework regions as well as one or more of the CDRs derived from the donor antibody as referred to herein. Thus, provided is a CDR-grafted antibody wherein the variable domain comprises human acceptor framework regions and non-human, preferably rat, mouse or rabbit donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at the following website (without the lead http://): vbase.mrc-cpe.cam.ac.uk/. In a further alternative a database of affinity matured human V region sequences may be used as a framework.

In a CDR-grafted antibody of the present invention, the acceptor heavy and light chains do not necessarily need to be derived from the same antibody and may, if desired, comprise composite chains having framework regions derived from different chains.

Also, in a CDR-grafted antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

Donor residues are residues from the donor antibody, i.e. the antibody from which the CDRs were originally derived, which may in one embodiment of the present invention be either of the rat, mouse or rabbit antibodies may be incorporated into the final antibody or fragment as required.

In one embodiment, the antibody, or fragment such as a Fab or Fab' fragment is a monoclonal, fully human, humanized or chimeric antibody fragment. In one embodiment the antibody Fab or Fab' fragments are fully human or humanised.

Antibodies for use in the present invention include whole antibodies of any suitable class for example, IgA, IgD, IgE, IgG or IgM or subclass such as IgG1, IgG2, IgG3 or IgG4. and functionally active fragments or derivatives thereof and may be, but are not limited to, monoclonal, humanised, fully human or chimeric antibodies.

Antibodies for use in the present invention may therefore comprise a complete antibody molecule having full length heavy and light chains or a fragment thereof and may be, but are not limited to Fab, modified Fab, Fab', F(ab')$_2$, Fv, single domain antibodies (such as VH, VL, VHH, IgNAR V domains), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO2005/003169, WO2005/003170 and WO2005/003171. Multi-valent antibodies may comprise multiple specificities or may be monospecific (see for example WO 92/22853 and WO05/113605).

In one example the antibodies for use in the present invention may be derived from a camelid, such as a camel or llama. Camelids possess a functional class of antibodies devoid of light chains, referred to as heavy chain antibodies (Hamers et al., 1993, Nature, 363, 446-448; Muyldermans, et al., 2001, Trends. Biochem. Sci. 26, 230-235). The antigen-combining site of these heavy-chain antibodies is limited to only three hypervariable loops (H1-H3) provided by the N-terminal variable domain (VHH). The first crystal structures of VHHs revealed that the H1 and H2 loops are not restricted to the known canonical structure classes defined for conventional antibodies (Decanniere, et al., 2000, J. Mol. Biol, 300, 83-91). The H3 loops of VHHs are on average longer than those of conventional antibodies (Nguyen et al., 2001, Adv. Immunol., 79, 261-296). A large fraction of dromedary heavy chain antibodies have a preference for binding into active sites of enzymes against which they are raised (Lauwereys et al., 1998, EMBO J, 17, 3512-3520). In one case, the H3 loop was shown to protrude from the remaining paratope and insert in the active site of the hen egg white lysozyme (Desmyter et al., 1996, Nat. Struct. Biol. 3, 803-811 and De Genst et al., 2006, PNAS, 103, 12, 4586-4591 and WO97049805).

It has been suggested that these loops can be displayed in other scaffolds and CDR libraries produced in those scaffolds (See for example WO03050531 and WO97049805).

In one example the antibodies for use in the present invention may be derived from a cartilaginous fish, such as a shark. Cartilaginous fish (sharks, skates, rays and chimeras) possess an atypical immunoglobulin isotype known as IgNAR. IgNAR is an H-chain homodimer that does not associate with light chain. Each H chain has one variable and five constant domains. IgNAR V domains (or V-NAR domains) carry a number of non canonical cysteines that enable classification into two closely related subtypes, I and II. Type II V regions have an additional cysteine in CDRs 1 and 3 which have been proposed to form a domain-constraining disulphide bond, akin to those observed in camelid VHH domains. The CDR3 would then adopt a more extended conformation and protrude from the antibody framework akin to the camelid VHH. Indeed, like the VHH domains described above, certain IgNAR CDR3 residues have also been demonstrated to be capable of binding in the hen egg white lysozyme active site (Stanfield et al., 2004, Science, 305, 1770-1773.

Examples of methods of producing VHH and IgNAR V domains are described in for example, Lauwereys et al, 1998, EMBO J. 1998, 17(13), 3512-20; Liu et al., 2007, BMC Biotechnol., 7, 78; Saerens et al., 2004, J. Biol. Chem., 279 (5), 51965-72.

In one embodiment the constant region employed, in the antibody or certain fragments thereof according to the disclosure, is a hybrid constant region or mutated constant region. Hybrid constant regions comprises portions or domains from two or more distinct constant regions, for example two or more distinct human constant regions.

Examples of hybrid constant regions include those disclosed in US2007/0041972, where at least CH1 and the hinge region are derived from one or more IgG2 antibodies and at least a portion of the CH2 and CH3 regions are derived from one or more IgG4 CH2 and CH3 regions. Eculizimumab (Alexion Pharmaceuticals) is a humanised anti-human C5 mAb for paroxysmal nocturnal hemoglobinuria comprising a hybrid constant region. It has a hybrid chain of IgG2 derived CH1 and hinge with IgG4 derived CH2 and CH3 domains. It does not bind FcγR nor does it activate complement. It also has low immunogenicity (low titres of anti-Eculizimumab antibodies detected in only 3 of 196 (3%) patients).

WO 2008/090958 discloses certain hybrid constant regions comprising a chain of CH1, hinge and CH2 from IgG1 and a CH3 domain from IgG3. The hybrid has a higher CDC activity than that of an IgG1 or IgG3 antibody and a protein A-binding activity equivalent to that of IgG1.

Further hybrid constant regions are disclosed in Tao et al., (S. L. Morrison's group) J. Exp. Med 173 1025-1028, 1991. This paper contains many IgG domain swaps from all classes but the key hybrids are g1g4 and g4g1, each joined in the CH2 domain. IgG (1-1-1/4-4) is completely unable to activate complement in contrast to IgG1. However, IgG(4-4-4/1-1) showed significant activity compared with IgG4 but was slightly impaired compared with IgG1. The key difference seems to be the hinge and many papers have since demonstrated that the hinge modulates but does not mediates complement activation.

Tao et al., (S. L. Morrison's group) J. Exp. Med 178 661-667, 1993 discloses structural features of human IgG that determine isotype-specific differences in complement activation. Ser331 (CH2) in IgG4 prevents C1q binding and complement activation. Mutagenesis of Ser331 to Pro in IgG4 and IgG (1-1-1/4-4) allows binding and activation but at a lower level than that of IgG1. Interestingly P331S in IgG1 allows binding but not activation.

Zucker et al., Cam Res 58 3905-3908 1998 employs Chimeric human-mouse IgG abs with shuffled constant region exons to demonstate that muliple domains contribute to in vivo half-life. In particular this article examines half-life of IgG (1-1-1/4-4) hybrid and others. In SCID mice, IgG (1-1-1/4-4) has a significantly longer half-life than IgG4 but slightly less than IgG1. IgG (4-4-4/1-1) has the longest half-life.

An example of a mutated constant region includes that employed in Abatacept, which is a fusion of human CTLA-4 with IgG1 hinge-Fc. The hinge was altered from CPPC (SEQ ID NO:166) to SPPS (SEQ ID NO:167) The latter is O-gly. The mutated constant region does not mediate ADCC or CDC and has low immunogenicity (3% incidence).

The hinge is thought to potentially have a role in complement activation. The functional hinge, deduced from crystallographic studies, extends from 216-237 of IgG1 and consists of EPKSCDKTHTCPPCPAPELLGG (SEQ ID NO: 70) upper, middle and lower hinge respectively. In one embodiment an antibody or fragment according to the disclosure comprises a functional hinge.

Mutations/modifications to the constant region may, for example result in increased stability, for example US 2004/0191265 discloses mutagenesis of IgG1 hinge, which increased the stability of an IgG by introducing one or more amino acid modifications in the hinge region at positions 233-239 or 249 of human IgG1. This provided reduced degradation upon heating to 55° C. for one week.

Alternatively, modification may be effected by making point mutations in labile amino acids (e.g., histidine or threonine) or reactive amino acids (e.g., lysine or glutamic acid) in the upper hinge portion (human IgG1 residues 226-243 and corresponding residues in other IgG subtypes and/or immunoglobulins from other species) and/or in the flanking CH1 and/or CH2 sequences (human IgG1 residue 249 and corresponding residues in other IgG subtypes and/or immunoglobulins from other species).

In further aspect there is provided a composition comprising an ion channel extracellular peptide for immunizing a host.

EXAMPLES

Therapeutic Antibody Generation/Selection

Peptides were supplied by Peptide Protein Research Ltd., Fareham, U.K. N to C terminal cyclic peptides were synthesised as side chain protected peptides according to the method of Barlos et al Int. J. Pept. Protein Res. 1991 and cyclisation was carried out in solution phase followed by side chain deprotection according to the method of Kessler H et al., 1989, in Computer-aided drug design, methods and applications, Ed. T. J. Perun and C. L. Probst, pp. 461-484, Marcel Dekker, New-York; Toniolo C., 1990, Int. J. Pept. Protein Res., 35, 287-300; Gurrath M. et al., 1992, Eur. J. Biochem., 210, 911-921; Izumiya N. et al., 1981, Biopolymers, 20, 1785-1791; Brady S. F. et al., 1983, in Peptides, Structure and Function, Proceedings of the Eighth American Peptide Symposium, Ed. V. J. Hruby and D. H. Rick, pp. 127-130, Pierce Chemical Company, Rockford, Ill.; He J. X. et al., 1994, Lett. Peptide Sci., 1, 25-30. Rabbits were immunised with combinations of human $Na_v1.7$ peptides conjugated to either KLH, OVA or BSA (Table 1). Following 5 subcutaneous immunisations (KLH, OVA, BSA, KLH, OVA), animals were sacrificed and PBMC, spleen and bone marrow harvested. Sera was tested for binding to human biotinylated peptide in ELISA.

TABLE 1

Table 1. $Na_v1.7$ peptide immunogens

| Rabbit | Peptides | Peptide Sequence |
|---|---|---|
| 3822 | A32 | A32-CTLESIMNTLESEEDFRKY (cyclic) (SEQ ID NO: 87) |
| 3823 and 3824 | B11, B31 | B11-CPMTEEFKN (cyclic) (SEQ ID NO: 90) B31-CTLPRWHMNDD (cyclic) (SEQ ID NO: 102) |
| 5825 | C11 | C11-CIERKKTIKI (cyclic) (SEQ ID NO: 92) |

The table shows immunised rabbit number, peptide combination employed for immunisation and peptide sequence. A32 is a peptide from loop E3 in domain A. B11 is a peptide from loop E1 in domain B. B31 is a peptide from loop E3 in domain B. C11 is a peptide from loop E1 in domain C.

SLAM was performed using substantially the methods described in Tickle et al. 2009 (JALA, Vol. 14, number 5, p 303-307). Briefly, SLAM cultures were set up using rabbit splenocytes or PBMC and supernatants were first screened for their ability to bind biotinylated peptide in a bead-based assay in the FMAT. This was a homogeneous assay using biotinylated human peptide bound to streptavidin beads (Bangs Laboratories) and revealing binding using a goat anti-rabbit Fc-Cy5 conjugate (Jackson immunoResearch). Positives from this screen were then put through a negative screen to identify non-specific antibodies. This used streptavidin beads with no peptide or with an irrelevant peptide, revealing binding with a goat anti-rabbit Fc-Cy5 conjugate (Jackson ImmunoResearch), to identify the peptide specific binders.

From 10 SLAM experiments, a number of A-32-specific, B11-specific and C11-specific antibody-containing wells were identified using the screens described above. Single B cell isolation via the fluorescent foci method and subsequent variable region gene cloning from a number of these wells successfully yielded heavy and light chain variable region gene pairs following reverse transcription (RT)-PCR. These V-region genes were cloned as rabbit IgG1 full-length antibodies and re-expressed in a HEK-293 transient expression system.

Sequence analysis of cloned v-regions revealed the presence of a number of unique families of anti-human B11-specific $Na_v1.7$ antibody and A32-specific antibodies (see table 2 below). DNA and amino acid sequences of these antibodies are shown in the Figures. Antibodies were expressed in a transient CHO system and subsequently purified to allow further characterisation in vitro and in vivo.

TABLE 2

| UCB antibody number | Rabbit number | Peptide specificity |
| --- | --- | --- |
| CA167_00915 | 3822 | A32 |
| CA167_00914 | 3822 | A32 |
| CA167_00933 | 3822 | A32 |
| CA167_00932 | 3822 | A32 |
| CA167_00931 | 3822 | A32 |
| CA167_00930 | 3822 | A32 |
| CA167_00983 | 3824 | B11 |
| CA167_00984 | 3824 | B11 |
| CA167_00985 | 3824 | B11 |
| CA167_01080 | 3824 | B11 |
| CA167_01081 | 3824 | B11 |
| CA167_01082 | 3824 | B11 |
| CA167_01083 | 3824 | B11 |
| CA167_01084 | 3824 | B11 |
| CA167_01085 | 3824 | B11 |
| CA167_01086 | 3824 | B11 |

FIGS. 6-11 show sequences for anti-$Na_v1.7$ antibodies. The immunised rabbit number that the antibodies were derived from and their peptide specificities are detailed.

Procedure for h $Na_v1.7$ Recording for Antibody Testing
Solutions and Antibodies Handling Extracellular solution contained (in mM): 130 NaCl, 4 KCl, 1.5 $CaCl_2$, 1 $MgCl_2$, 30 glucose, 10 HEPES (pH 7.4 with Tris-Base, and 300 to 305 mOsmolar). Intracellular solution contained (in mM): 5 NaCl, 115 CsF, 20 CsCl, 110 HEPES, 10 EGTA free acid (pH 7.2 with CsOH, and 290 to 295 mOsmolar) and was either made fresh or kept frozen. Extracellular and intracellular solutions were filtered prior to use. Antibodies were directly diluted in extracellular solution and were freshly (no more than 15 min) prepared before transfer to a 96-well polypropylene compound plate (Sarsted, #83.1835.500). For the experiments using selective peptide, antibodies and peptides, at equal concentrations, were preincubated at least 30-min at 4° C. prior Patch Clamp experiments.

Cell Preparation

HEK293 cells stably expressing the human $Na_v1.7$ channel (type IX voltage-gated sodium channel alpha subunit) were purchased from Upstate (Upstate, Millipore, cat.#CYL3011). Cells were cultured in T-75 (BD BioCoat™ Collagen I Cellware, Becton Dickinson Labware, Bedford, Mass., #356485) flasks coated with collagen type I using standard culture medium DMEM-F12 with-Glutamine (Invitrogen, #11320) containing 10% FBS (Lonza, #DE14-802F), 1% penicillin+streptomycin (Lonza, DE17-603E), 1% non essential amino acids (Lonza, BE13-114E) and 400 µg/ml G418 (GIBCO, #10131-027). Cells were plated at a density of 15,000 cells/cm2 or 8,000 cells/cm2 density for 2 or 3 days respectively before being used on PatchXpress® 7000A (Axon instrument, new part of MDS Analytical Technologies). Cells confluence never exceeded 90%. The day of the experiment, cells were harvested using ACCUMAX solution (Sigma, A7089). Briefly, cells were washed twice in PBS (Lonza, #BE12-516F) without calcium and magnesium, and a 1:4 dilution of ACCUMAX solution was added and incubated for 1.5 to 2-min at 37° C. DMEM-F12 with 15 mMHEPES and L-glutamine (Lonza, #BE12-719F) containing 10% FBS (recovery media) was added to quench ACCUMAX solution digestion. The cells were subsequently centrifuged at 1,000 rpm for 5-min in 50 ml falcon tube and pellets are resuspended in 10 ml of recovery media. Cells are counted (Z2 COULTER COUNTER) and suspended at ~0.1 million cells/ml and transferred to a 15 ml screw-cap tube for minimum 90 minutes at room temperature. Cells were then centrifuged for 60-s at 1,000 rpm. The pellet was gently resuspended in 1,000 µl extracellular solution and centrifuged a second time for 30-s at 1,000 rpm. Pellet was resuspended in 1504, extracellular solution and immediately tested on the PatchXpress® system.

PatchXpress® Procedures

The AVIVA Biosciences SealChip16™ electrode arrays (purchased from Axon Instruments, Union City, Calif.) were manually placed in the holder of the PatchXpress® system and automatically prepared for application of the cells. Intracellular solution was injected into the bottom of each chamber, and extracellular solution was perfused into the top of the chambers through the 16-nozzle wash station. Throughout this period, the pressure controller maintained a positive pressure (+10 mmHg) from the intracellular side to keep the hole free of debris. Cells were triturated by the integrated Cavro pipetting robot prior to addition of 4 µl (containing 10K-30K cells) to each well.

PatchXpress® h $Na_v1.7$ Assay

After 10-s, the pressure was switched from +4 to −30 mmHg to attract suspended cells to each of the 16 holes (electrodes). Seal formation was achieved by repeating negative pressure ramp from −1 to −35 mmHg at a rate of 1.6 mmHg/s every 36-s until a Giga Ohm Seal was obtained and verified for 20-s. Whole-cell access was achieved by rupturing the patch of membrane over the hole using a ramp increase in negative pressure from −40 to −150 mmHg at a rate of 7.5 mmHg/s with a pipette potential of −80 mV. After whole cell configuration cells are washed with extracellular solution for 66-s to remove the excess cells in the well. The cell was allowed to dialyze for 5 min, during which the access resistance was monitored. From the time of whole-cell break-in to the end of the experiment, the cells were held at −80 mV between voltage protocols. A time course protocol was applied to assess the antibody potencies on sodium current elicited by a depolarizing step from −80 mV to 0 mV for 20 milliseconds at 10 seconds interval. Whole cell compensation was automatically made before each trial starts and electrical access resistance (Ra) was corrected by 65%. Linear leak substraction was performed online using a P/N leak subtraction protocol (N=4) at the holding of −80 mV.

After a stabilizing period (up to 10 min), a negative control solution (extracellular solution) was applied for 5-min, followed by two doses of antibodies. The interval between both additions of the same concentration of compound to a well was ~11-s. Antibody solution (45 µL) was added online (30 µL/s) at the desired concentration with permanent aspiration. Currents were monitored continuously during the 18-min exposure to the antibody.

Data Analysis

Cells were not analyzed if:
(1) the membrane resistance was initially <200 MOhm,
(2) current amplitude <200 pA,
(3) an access resistance no greater then 20 MOhm and
(4) no real stabilized current after negative control addition.

The current amplitude was measured using DataXpress2 software (Axon instruments) and rundown current correction was performed by linear or exponential fitting method on the measurement associated with the last 10-15 data points after the washout period and the last 10-15 data point after the negative control addition.

Current was normalized by the mean current corrected amplitude prior antibody addition. Current inhibition was estimated by the residual response after 18-min antibodies application. Data is given below in Table 3.

TABLE 3

Table 3: Inhibition of Nav 1.7 currents expressed in HEK cells.

| Antibody | Peptide | Concentration (µg/ml) | Nav1.7 inhibition (%) |
|---|---|---|---|
| CA167_00914 | A32 | 25 | 28 |
| CA167_00915 | A32 | 25 | 26 |
| CA167_00931 | A32 | 2.5 | 9 |
| CA167_00932 | A32 | 25 | 27 |
| CA167_00933 | A32 | 25 | 8 |
| CA167_00983 | B11 | 25 | 41 |
| CA167_00984 | B11 | 25 | 9 |
| CA167_00985 | B11 | 25 | 12 |
| CA167_01080 | B11 | 25 | 46 |
| CA167_01081 | B11 | 25 | 33 |
| CA167_01082 | B11 | 25 | 10 |
| CA167_01083 | B11 | 25 | 16 |
| CA167_01084 | B11 | 25 | 27 |
| CA167_01085 | B11 | 25 | 27 |
| CA167_01086 | B11 | 25 | 31 |
| R3822_A32 | A32 | 25 | 53 |
| R3824_B11 | B11 | 25 | 68 |
| R5825_C11 | C11 | 25 | 20 |

FIG. 2

Figure 2:
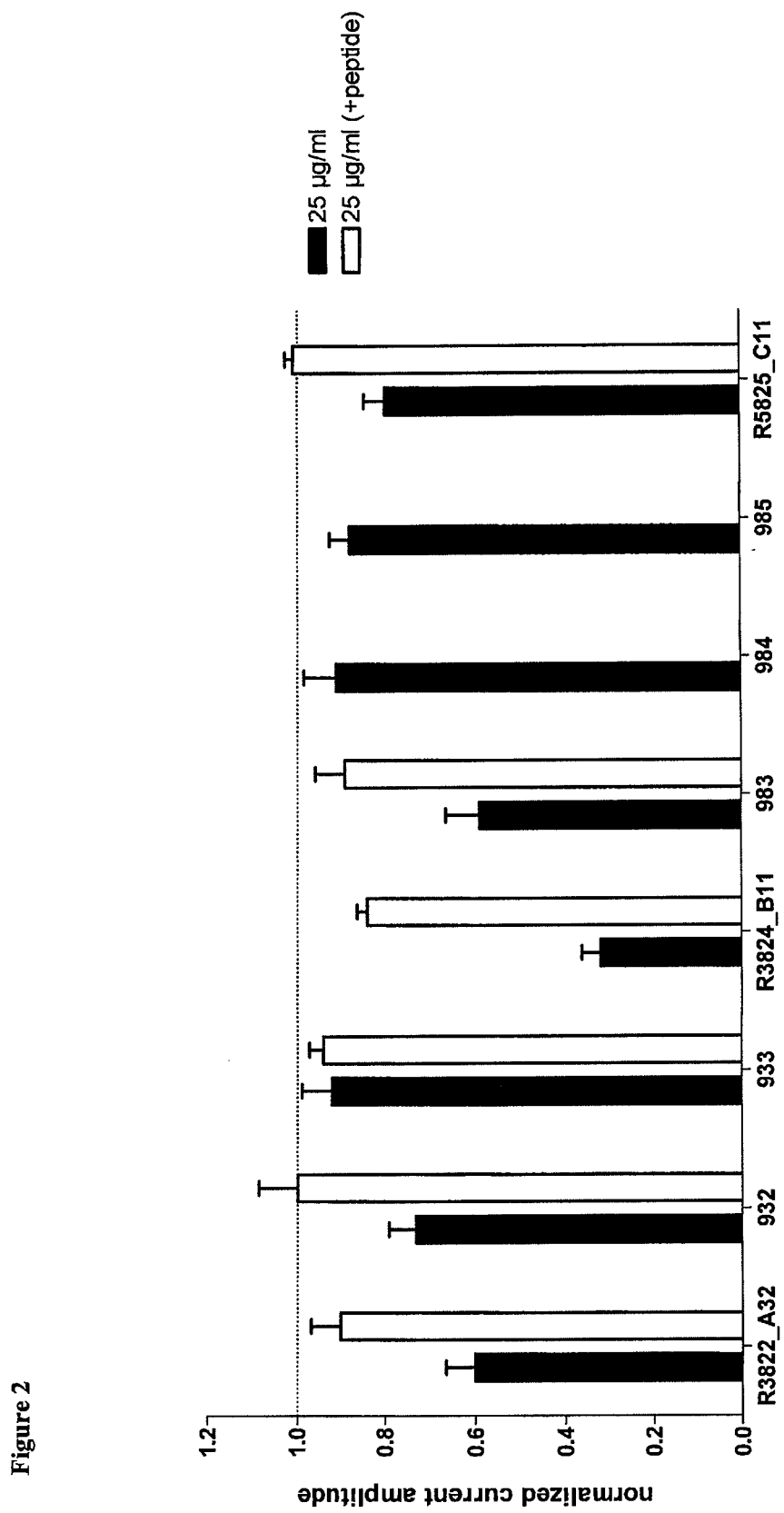
FIG. 2 shows the functional effects of certain monoclonal antibodies on human $Na_v1.7$ current in HEK cells.

FIG. 2 shows the functional effects of selected antibodies (at 25 µg/ml), in the presence or absence of specific peptide, on human Nav1.7 currents expressed in HEK cells. Nav1.7 currents were recorded by automated Patch Clamp using a repetitive stimulation protocol and data are presented as the normalized Nav1.7 current after the last stimulation. Selected antibodies were incubated in the presence of the specific peptide (25 µg/ml) for 30 minutes at 4° C. and then transferred to the PatchXpress system for Nav1.7 current recordings. The presence of the peptide systematically reverses the inhibitory effect of the antibody thus indicating that inhibition of Nav1.7 currents is mediated by a specific interaction of antibodies with the Nav1.7 extracellular loops.

FIG. 3e (a)

Automated Patch Clamp analysis of recombinant human Nav1.7 channels expressed in HEK cells. 983 monoclonal antibody produces a dose-dependent inhibition of Nav1.7 currents. Data points represent the normalized peak current amplitudes after application of a repeated voltage step protocol (end point) in the presence of antibody.

FIG. 3e (b)

Automated Patch Clamp analysis of recombinant human Nav1.7 channels expressed in HEK cells. 1080 monoclonal antibody produces a dose-dependent inhibition of Nav1.7 currents. Data points represent the normalized peak current amplitudes after application of a repeated voltage step protocol (end point) in the presence of antibody.

FIG. 3f

Automated Patch Clamp analysis of recombinant rat Nav1.7 channels expressed in HEK cells. 983 monoclonal antibody produces a dose-dependent inhibition of Nav1.7 currents. 1080 monoclonal antibody produces a ~26% inhibition of Nav1.7 currents at 25 µg/ml. Data points represent the normalized peak current amplitudes after application of a repeated voltage step protocol (end point) in the presence of antibody.

FIG. 3g

Kinetics of human Nav1.7 inhibition by 983 monoclonal antibody. HEK cells expressing recombinant human Nav1.7 channels are stimulated with a voltage step protocol at 0.1 Hz for ~20 minutes. Data points represent the normalized peak current amplitudes (run down corrected) of Nav1.7 channels recorded every 10 seconds. Nav1.7 currents are reduced in the presence of the antibody (25 µg/ml) but only when repeated activation of the channel at 0.1 Hz is maintained. Stimulation of Nav1.7 channels only at the end of the protocol (and after incubation of antibody) does not produce an inhibition of the Nav1.7 current. Data suggest that specific inhibition by 983 monoclonal antibody requires repetitive activation (channel cycling) of the Nav1.7 channel protein.

Dorsal Route Ganglion In Vitro Testing

Primary Culture Preparation

Dorsal Root Ganglia were isolated from 1-2 wild-type rat pups, aged between postnatal day 1 and 3. Ganglia were washed in PBS after dissection and immediately placed into a DMEM (Lonza, #BE12-604F) solution containing 2 mg/ml collagenase (Sigma-Aldrich, #C2674) and incubated at 37° C. for approximately 45 minutes for enzymatic digestion. Collagenase solution was removed and replaced with DMEM supplemented with 10% Fetal Bovine Serum (Lonza, #DE14802F), 0.5 mM L-Glutamine (Lonza, #BE17-605E), 1% Penicillin/Streptomycin (Lonza, #BE17-603E) and 20 ng/ml nerve growth factor (NGF, Invitrogen). Ganglia were then mechanically triturated, centrifuged at 1000 g for 5 minutes, and resuspended in the same culture medium. Dissociated cells were counted and diluted to a suspension of 100,000-120,000 cells/ml on glass coverslips precoated with 50 µg/ml poly-D-lysine (Sigma) and 30 µg/ml laminin (Invitrogen) and incubated at 37° C., 5% $CO_2$ until ready for use.

Primary Culture Electrophysiology

Dissociated DRG were taken for use no more than two days in vitro (DIV) following preparation. Cells were visualized on an Olympus BX50WI upright microscope with an Ikegami ICD-42B CCD camera. Electrophysiological recordings were acquired using 5 khz digital sampling and filtered at 3 dB at a 3 khz frequency on an Axopatch 1D (Molecular Devices) amplifier and converted to a digital signal using a Digidata 1322A analog-to-digital converter (Molecular Devices). All recordings were acquired using pClamp 10 software (Molecular Devices) and subsequently analyzed in Clampfit 10 (Molecular Devices). Recording electrodes were pulled from borosilicate glass pipettes on a Sutter p-97 horizontal pipette puller to a final resistance of 4.5-6MΩ and filled with an internal solution containing (in mM): 140 K-Methansulfonate, 5 NaCl, 1 CaCl2, 2 MgCl2, 11 EGTA, 10 HEPES, 2 Mg-ATP, and 1 Li-GTP; pH was adjusted to 7.2 with Tris-base, and osmolality was adjusted to 310 mOsm with sucrose. Bath solution contained (in mM): 130 NaCl, 25 glucose, 10 HEPES, 4 KCl, 2 $CaCl_2$, 1 $MgCl_2$, 1.25 $NaPO_4$; pH was adjusted to 7.35 with NaOH and osmolality was adjusted to 310 mOsm with sucrose. The liquid junction potential was calculated to be 14.2 mV, all reported voltages have been corrected to compensate.

After formation of a tight seal (>1GΩ) by release of positive pressure and manual suction in voltage clamp mode, capacitative currents were compensated and the command voltage was set to −70 mV. The cell membrane was ruptured and the cell allowed to dialyze intracellular solution for 5 minutes. Whole cell parameters were recorded after dialysis. Cells were rejected if whole cell capacitance was >35 pF or a stable access resistance less than 3× electrode resistance could not be achieved. The amplifier was switched to current clamp mode and the resting membrane potential was recorded. The cell was then injected with a series of 1.5 s duration, depolarizing current steps of increasing amplitude intended to evoke an action potential (AP) or train of APs. Cells that could not fire more than a single AP during a single step after depolarizing to a maximum of −35 mV were rejected.

Cells were subsequently treated either with control or antibody solutions by fast bath perfusion directly on to the recorded cell for 90 seconds to sufficiently fill the recording chamber, at which point both perfusion and aspiration were halted. The previous series of depolarizing current steps were repeatedly administered at two minute intervals over a period of 40 minutes, typically with a delay of 1.5 s between individual steps to allow for membrane repolarization. Occasionally a constant current was injected if the resting membrane potential (RMP) adjusted over the course of the experiment in order to maintain a constant RMP of −65 mV. Cells whose RMP deviated more than 20% in either the positive or negative direction or whose holding current changed more than 100 pA during the course of the experiment were rejected. Individual holding currents and injected currents for each step were noted individually for each cell, as well as any electrophysiological parameters that were changed during the course of the experiment.

Data Analysis

Action Potentials (AP) were manually counted for each depolarizing step and the total number of evoked APs were summed for each time point. The number of APs at each time point were normalized in Microsoft Excel 2003 to the number of evoked APs at time=0 and plotted as a function of time using Graphpad Prism 5.0 software. Each plotted data point represents the mean value of all recorded cells under the specified experimental condition, with error bars representing the calculated standard error.

Figure 3A:
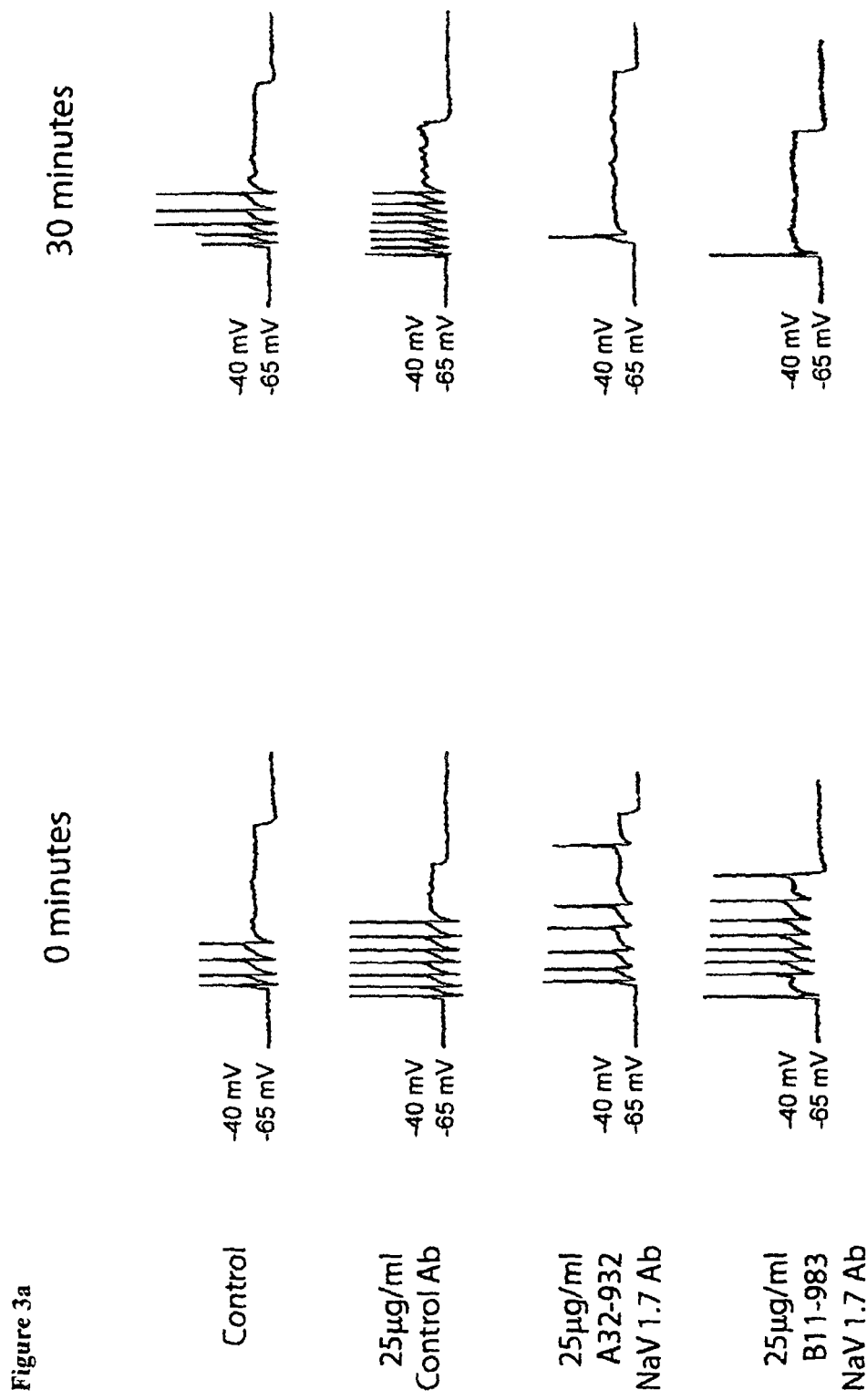
FIG. 3a shows that the 932 and 983 anti-$Na_v1.7$ monoclonal antibodies reduce electrically induced DRG spike frequency in vitro.

FIG. 3a Current clamp traces of evoked action potentials from representative DRG neurons before (time=0) and following (time=30 minutes) treatment.

Figure 3B:
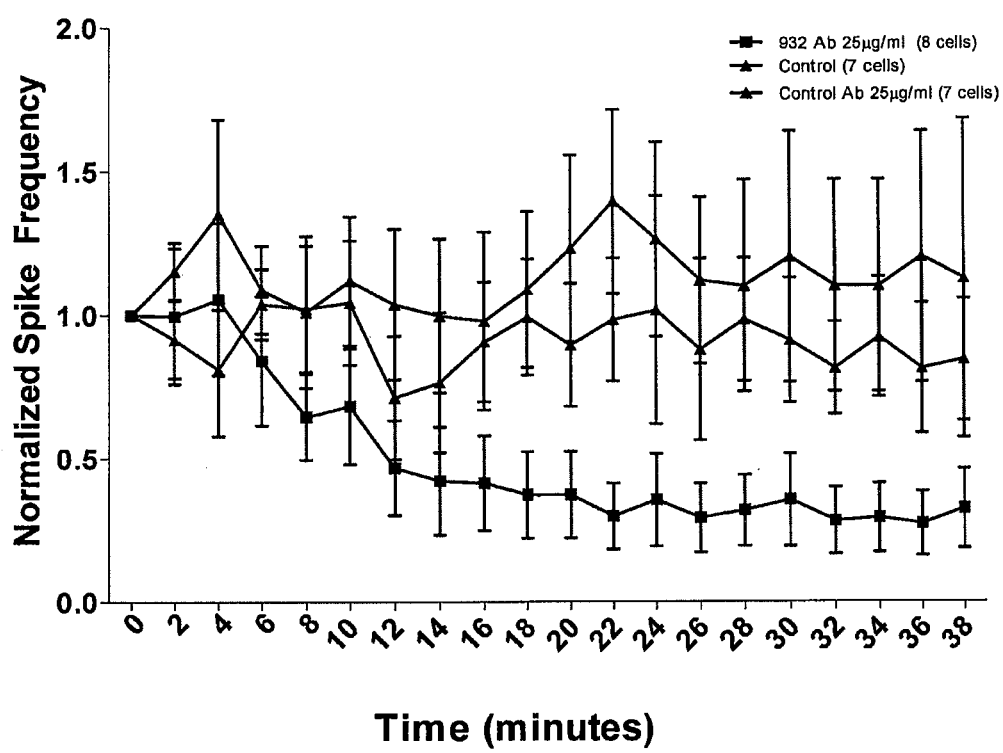
FIG. 3b shows that anti-$Na_v1.7$ monoclonal antibody 932 reduces electrically induced DRG spike frequency in vitro.

FIG. 3b The antibody 932 (25 μg/ml) significantly reduced the number of evoked action potentials compared with vehicle or control antibody treated controls following antibody administration at time=2 minutes.

Figure 3C:
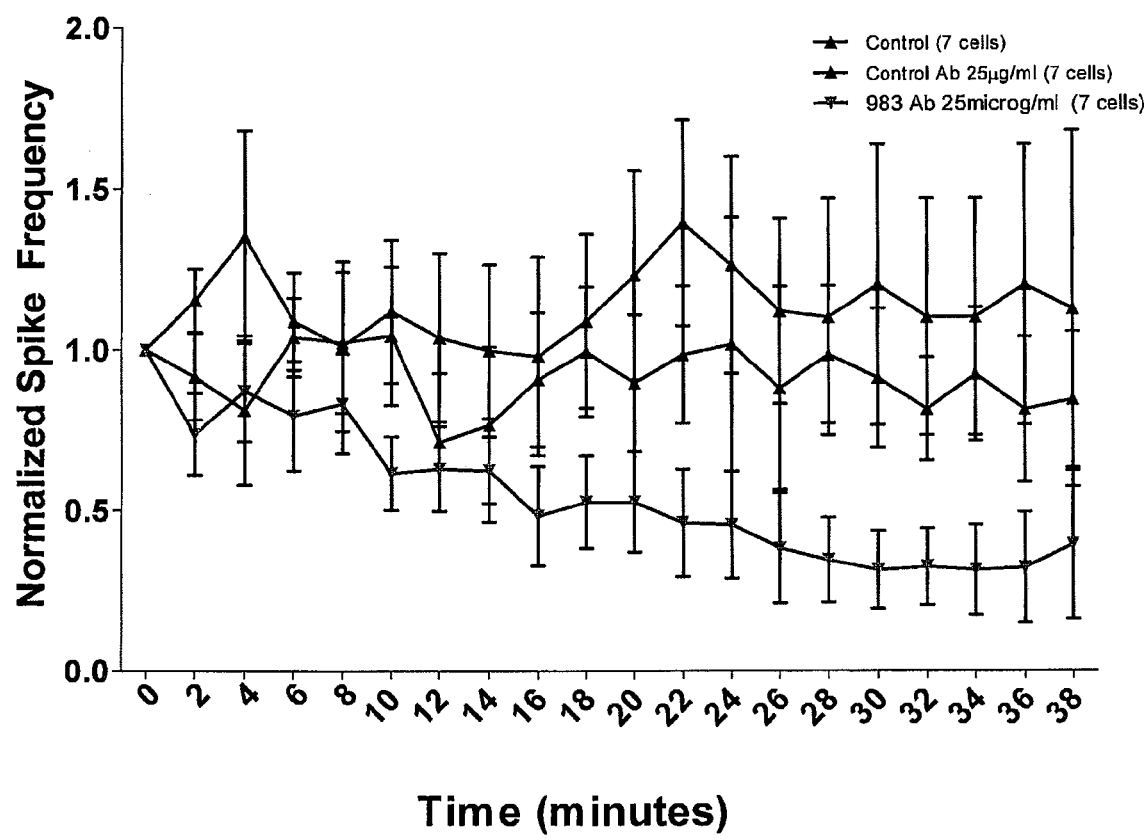
FIG. 3c shows that anti-$Na_v1.7$ monoclonal antibody 983 reduces electrically induced DRG spike frequency in vitro

FIG. 3c: The antibody 983 (25 μg/ml) significantly reduced the number of evoked action potentials compared with vehicle or control antibody treated controls following antibody administration at time=2 minutes.

Figure 3D:
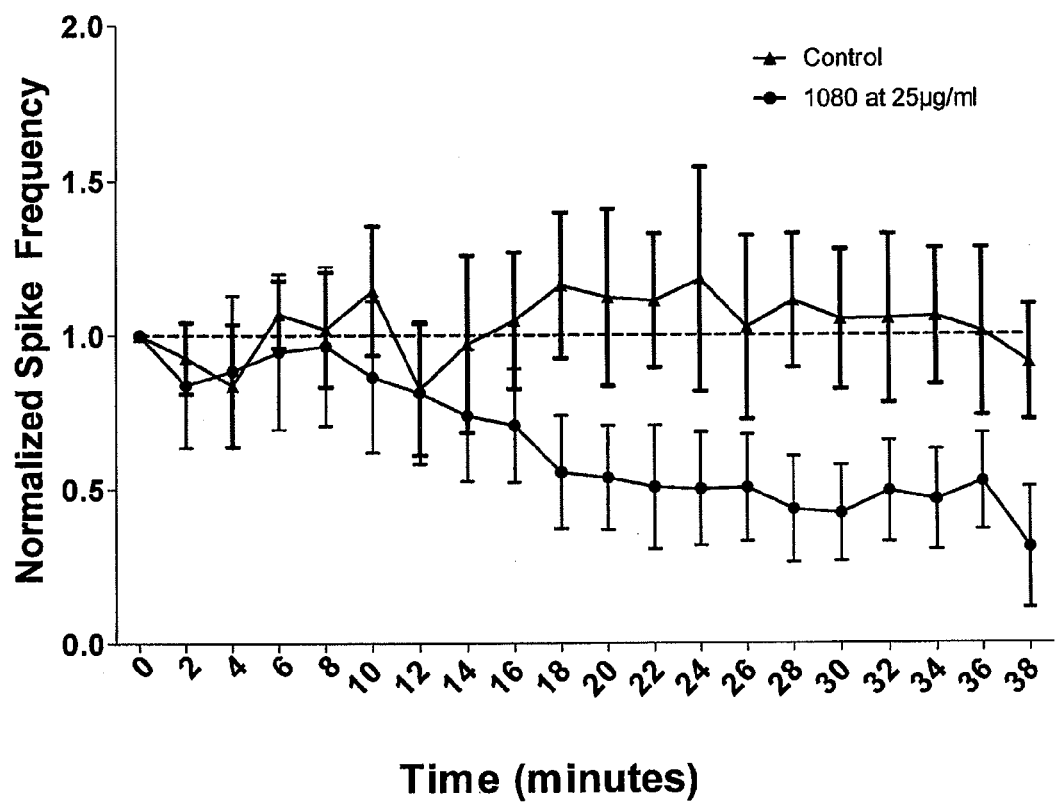
FIG. 3d shows that anti-$Na_v1.7$ monoclonal antibody 1080 reduces electrically induced DRG spike frequency in vitro FIG. 3e (a) shows automated Patch Clamp analysis of recombinant human Nav1.7 channels expressed in HEK cells. 983 monoclonal antibody produces a dose-dependent inhibition of Nav1.7 currents.
Figure 3F:
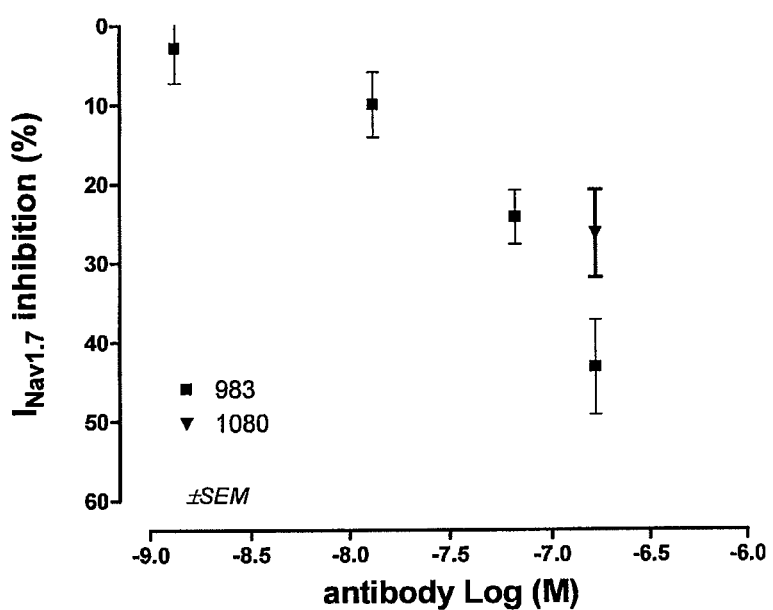
FIG. 3f shows automated Patch Clamp analysis of recombinant rat Nav1.7 channels expressed in HEK cells. 983 monoclonal antibody produces a dose-dependent inhibition of Nav1.7 currents. 1080 monoclonal antibody produces a ~26% inhibition of Nav1.7 currents at 25 µg/ml.
Figure 3G:
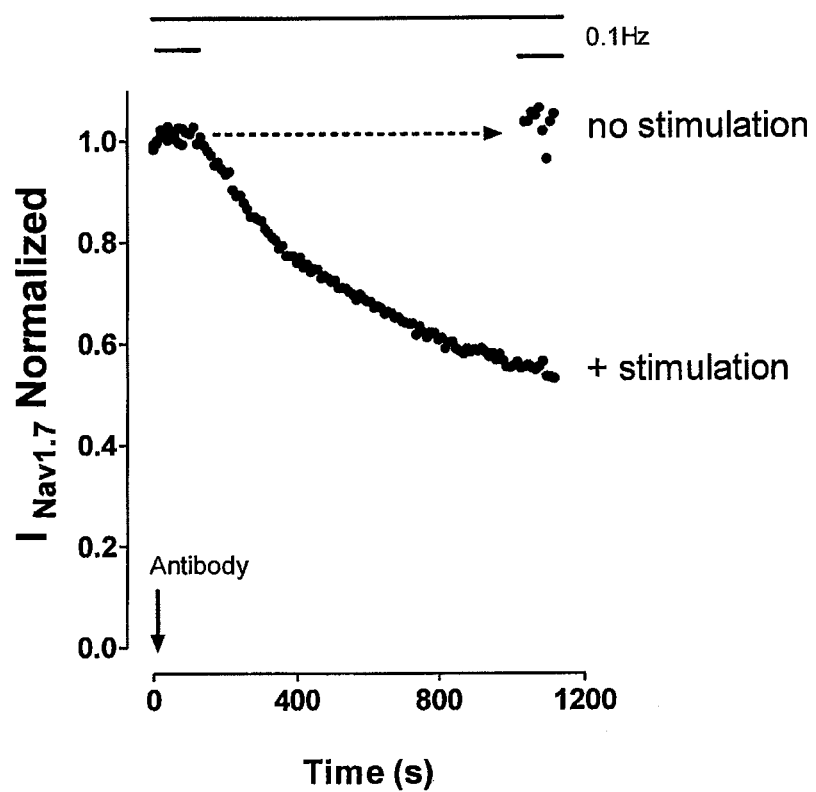
FIG. 3g Kinetics of human Nav1.7 inhibition by 983 monoclonal antibody.

FIG. 3d: Electrophysiology (current clamp recordings) investigations on action potential firing in cultured rat dorsal root ganglion (DRG) neurons. 1080 monoclonal antibody, at a dose of 25 μg/ml, reduces the electrically induced spike frequency of DRG neurons. Data points represent the normalized spike frequency compared to initial frequency observed at time 0 before antibody application.

Isoform and Species Selectivity for 983 and 1080

TABLE 4

E1 peptides used for Nav isoform and species selectivity studies

| Peptide Name | Ion channel | Sequence |
| --- | --- | --- |
| B11.1 | Nav 1.1 | Cyclo[biotinyl-PEG-cysEHYP MTDHFNN] (SEQ ID NO: 159) |
| B11.2/3 | Nav 1.2 and 1.3 | Cyclo[biotinyl-PEG-cysEHYP MTEQFSS] (SEQ ID NO: 160) |
| B11.4 | Nav 1.4 | Cyclo[biotinyl-PEG-cysEHYP MTEHFDN] (SEQ ID NO: 161) |
| B11.5 | Nav 1.5 | Cyclo[biotinyl-PEG-cysEHYN MTSEFEE] (SEQ ID NO: 162) |
| B11.6 | Nav 1.6 | Cyclo[biotinyl-PEG-cysEHHP MTPQFEH] (SEQ ID NO: 163) |
| B11.7 | Nav 1.7 | Cyclo[biotinyl-PEG-cysPMTE EFKN] (SEQ ID NO: 90) |
| B11.8 | Nav 1.8 | Cyclo[biotinyl-PEG-cysEHHG MSPTFEA] (SEQ ID NO: 164) |
| B11.9 | Nav 1.9 | Cyclo[biotinyl-PEG-cysEHHK MEASFEK] (SEQ ID NO: 165) |

Peptide Binding ELISA

Nunc 96 well plates were coated overnight at 4° C. in 5 ug/ml Streptavidin (Jackson 016-000-114) 100 ul/well in carbonate coating buffer. Plates were washed four times in PBS/tween and 200 ul/well of block (1% BSA in PBS) was added for 1 hour at RT. Plates were washed four times in PBS/tween and 100 ul/well of biotinylated peptide at 5 ug/ml was added for 1 hour at RT. Plates were washed four times in PBS/tween and 100 ul/well of antibody added (starting at 10 ug/ml diluting in block in half logs down the plate) for 1 hour at RT. Plates were washed four times in PBS/tween and 100 ul/ml goat anti rabbit Fc HRP (Jackson 111-036-046) added for 1 hour at RT. Plates were washed four times in PBS/tween and 100 ul/well TMB (3,3',5,5' Tetramethylbenzidine) solution added. 50 ul/well of NaF was added to stop reaction and absorbance read at 630 nm.

Figure 4:
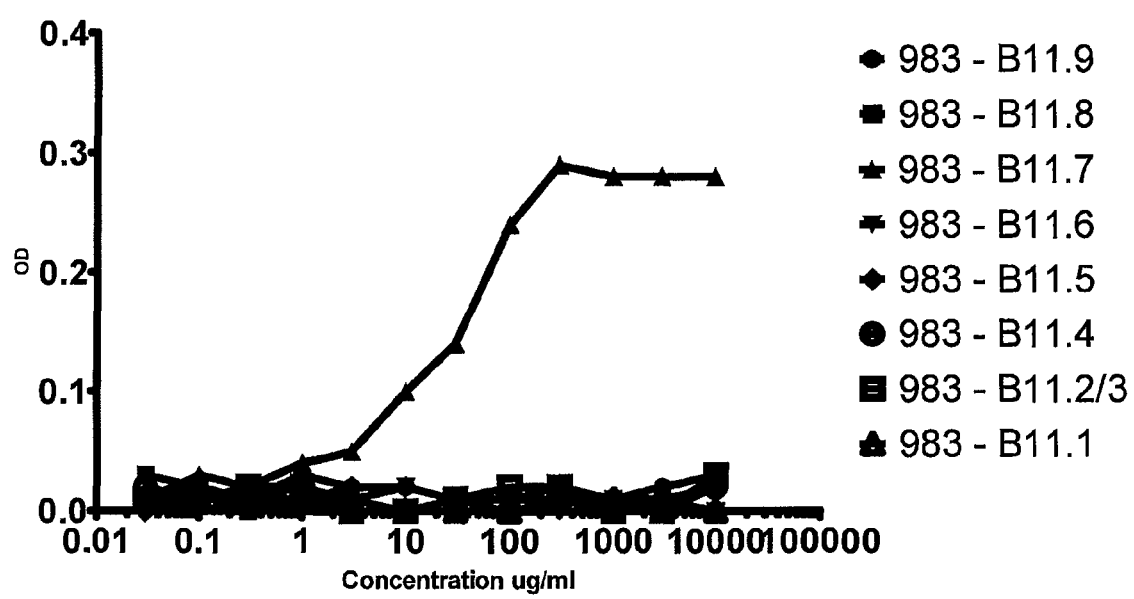
FIG. 4 shows ELISA data for antibody 983 specific binding to Nav 1.7 peptide

FIG. 4 shows ELISA data for antibody 983 binding to various cyclic Nav ion channel peptides Table 4

Figure 5:
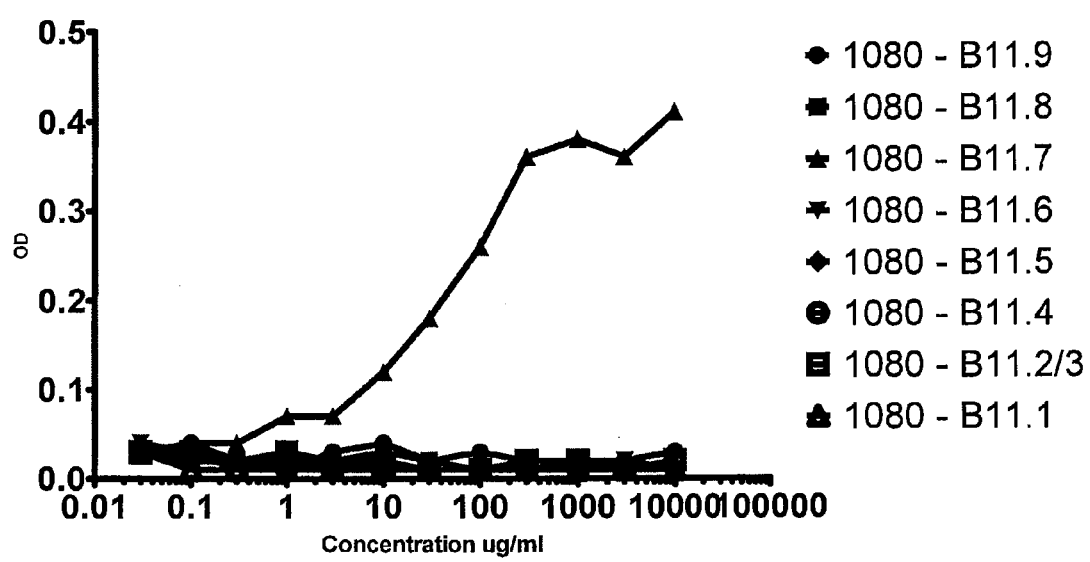
FIG. 5 shows ELISA data for antibody 1080 specific binding to Nav 1.7 peptide.

FIG. 5 shows ELISA data for antibody 1080 binding to various cyclic Nav ion channel peptides Table 4.

Specific binding in both cases was only observed for the B11.7 peptide and no binding to equivalent loops from the other Nav ion channels was observed.

Polyclonal Anti-Na$_v$1.7 Antibodies

Polyclonal anti-Na$_v$1.7 antibodies were raised against cyclic peptides A32 (SEQ ID NO:87), B11 (SEQ ID NO:90) and C11 (SEQ ID NO:92) using the immunization and SLAM screening methods described above prior to single B cell isolation via the fluorescent foci method and subsequent variable region gene cloning.

The polyclonal antibodies were purified as follows: Biotinylated peptide, corresponding to the peptide conjugate used for immunization, was added to a final concentration of 10 μM peptide to diluted immune rabbit plasma harvested as a total bleed from the respective rabbit. The mixture was allowed to equilibrate at 4° C. for two days. Antibody peptide complexes were isolated by applying the plasma mixture to a streptavidin affinity column (HiTrap NHS ester column that had previously coupled with streptavidin). After washing the column with 12 column volumes of phosphate buffered saline, anti-peptide antibody was eluted with 25 mM glycine/HCl pH 1.5 (3×20 ml fractions) and collecting each fraction into 5 ml 2M TRIS/EDTA pH 8.5. A second purification involved loading the neutralized fractions onto a HiTrap Protein G column followed by a 10 column volume phosphate buffered saline wash. Antibody was eluted with 20 column volumes of 0.1M glycine/HCl pH 2.7 and neutralizing fractions with 2M TRIS/EDTA pH 8.5. The latter were concentrated and using an Amicon Ultra 15 spin filter (50 kDa cut-off) then buffer exchanged into 'patch Clamp buffer' (10 mM HEPES, 130 mM NaCl, 4 mM KCl, 1.5 mM CaCl$_2$, 1 mM MgCl$_2$, 30 mM glucose pH 7.4). The resulting anti-peptide IgG was sterile filtered and protein concentration estimated by measuring absorbance at A$_{280nm}$.

Figure 12:
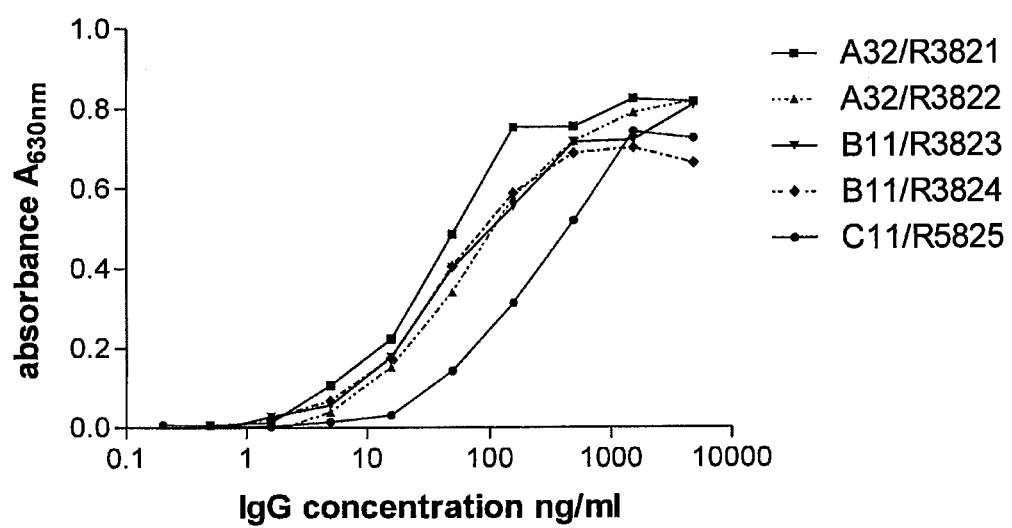
FIG. 12 shows binding data for various polyclonal antibodies.

FIG. 12 shows binding data for affinity purified anti-Na$_v$1.7 polyclonal antibodies generated as described above.

---

I claim:

1. A method for generating an antibody to a sodium ion channel comprising immunizing a host with a cyclic peptide comprising of 5 to 30 amino acids of an extracellular sequence of said ion channel, wherein the cyclised peptide contains a single cysteine or homocysteine residue linking the N-terminal to the C-terminal.

2. The method according to claim 1, wherein the ion channel has a function in the modulation of pain.

3. The method according to claim 1, wherein the extracellular sequence of the sodium ion channel is from an E1 extracellular region, an E2 extracellular region, or an E3 extracellular region.

4. The method according to claim 3, wherein the sodium ion channel is selected from the group consisting of $Na_v1.1$, $Na_v1.2$, $Na_v1.3$, $Na_v1.4$, $Na_v1.5$, $Na_v1.6$, $Na_v1.7$, $Na_v1.8$, and $Na_v1.9$.

5. The method according to claim 4, wherein the extracellular sequence is derived from the A domain, B domain, C domain, or D domain of the ion channel.

6. The method of claim 1, wherein the cyclic peptide is conjugated to a carrier.

7. The method according to claim 6, wherein the carrier is ovalbumin, bovine serum albumin, or keyhole limpet hemocyanin.

8. The method according to claim 1, wherein the cyclic peptide is joined in a region of sequence overlap in the linear sequence.

9. The method according to claim 1, wherein the peptide is cyclised by formation of an amide bond.

10. The method according to claim 1, wherein the peptide is cyclised by formation of a disulfide bond.

11. The method according to claim 1, wherein an adjuvant is administered concomitantly or sequentially with the cyclic peptide to stimulate an immune response thereto.

12. The method according to claim 11, wherein the adjuvant is selected from Freud's complete or incomplete adjuvant, or a formulation comprising a saponin, MPL, CPG, or combinations thereof.

13. The method according to claim 1, wherein the host is immunized multiple times.

14. The method according to claim 13, wherein the host is immunized twice or three times.

15. The method according to claim 13, wherein the host is immunized at 1 to 4 weekly intervals after a first immunization.

16. The method according to claim 13, wherein at least one immunization, subsequent to the first immunization, employs a cyclic peptide conjugated to a carrier.

17. The method according to claim 13, wherein each immunization, subsequent to the first immunization, employs a carrier that is different to the carrier conjugated to the peptide employed in the first immunization; and employs the same peptide employed in the first immunization.

18. A method according to claim 1, wherein a mixture of ion channel peptides are employed in combination for immunizing the host; and wherein the peptides are all from the same ion channel.

19. The method according to claim 1, which comprises the further step of harvesting cells generating antibodies.

\* \* \* \* \*

SEQUENCE LISTING

```
<160> NUMBER OF SEQ ID NOS: 167

<210> SEQ ID NO 1
<211> LENGTH: 330
<212> TYPE: DNA
<213> ORGANISM: Artificial Sequence
<220> FEATURE:
<223> OTHER INFORMATION: derived from rabbit

<400> SEQUENCE: 1
gcctatgata tgacccagac tccagcctct gtggaggtag ctgtgggagg cacagtcacc      60
atcaattgcc aggccagtga gagcattggc actgcattag cctggtatca gcagaaacca    120
gggcagcctc ccaagctcct gatctacaag gcatccactc tggaatctgg ggtcccatcg    180
cggttcaaag gcggtggatc tgggacacag ttcactctca ccatcagcgg cgtgcagtgt    240
gacgatgctg ccacttacta ctgtcaacag ggtgaaactg caaatagaat tgataatgct    300
ttcggcggag ggaccgaggt ggtcgtcaaa                                      330

<210> SEQ ID NO 2
<211> LENGTH: 333
<212> TYPE: DNA
<213> ORGANISM: Artificial Sequence
<220> FEATURE:
<223> OTHER INFORMATION: derived from rabbit

<400> SEQUENCE: 2
cagtcggtgg aggagtccgg gggtcgcctg gtcacgcctg ggacacccct gacactcacc      60
tgcacagtct ctggaatcga cctcagtcgc aatgcaatga cctgggtccg ccaggctcca    120
gggaaggggc tggaatacat cgcatacatt aatactaggg gtgacacatc ctacgcgaac    180
tgggcgaaag gccgattcac catctccaaa acctcgacca cggtggatct gaaaatgacc    240
agtctgacaa ccgaggacac ggccacctat ttctgtgttc atggttataa tccctgtaag    300
ttgtggggcc aaggcaccct ggtcaccgtc tcg                                  333

<210> SEQ ID NO 3
<211> LENGTH: 110
<212> TYPE: PRT
<213> ORGANISM: Artificial Sequence
<220> FEATURE:
<223> OTHER INFORMATION: derived from rabbit

<400> SEQUENCE: 3

Ala Tyr Asp Met Thr Gln Thr Pro Ala Ser Val Glu Val Ala Val Gly
```

-continued

```
                1               5              10              15
            Gly Thr Val Thr Ile Asn Cys Gln Ala Ser Glu Ser Ile Gly Thr Ala
                               20                  25                  30

Leu Ala Trp Tyr Gln Gln Lys Pro Gly Gln Pro Pro Lys Leu Leu Ile
                           35                  40                  45

Tyr Lys Ala Ser Thr Leu Glu Ser Gly Val Pro Ser Arg Phe Lys Gly
                       50                  55                  60

Gly Gly Ser Gly Thr Gln Phe Thr Leu Thr Ile Ser Gly Val Gln Cys
             65                  70                  75                  80

Asp Asp Ala Ala Thr Tyr Tyr Cys Gln Gln Gly Glu Thr Ala Asn Arg
                               85                  90                  95

Ile Asp Asn Ala Phe Gly Gly Gly Thr Glu Val Val Val Lys
                          100                 105                 110

<210> SEQ ID NO 4
<211> LENGTH: 111
<212> TYPE: PRT
<213> ORGANISM: Artificial Sequence
<220> FEATURE:
<223> OTHER INFORMATION: derived from rabbit

<400> SEQUENCE: 4

Gln Ser Val Glu Glu Ser Gly Gly Arg Leu Val Thr Pro Gly Thr Pro
            1               5                  10                  15

Leu Thr Leu Thr Cys Thr Val Ser Gly Ile Asp Leu Ser Arg Asn Ala
                           20                  25                  30

Met Thr Trp Val Arg Gln Ala Pro Gly Lys Gly Leu Glu Tyr Ile Ala
                       35                  40                  45

Tyr Ile Asn Thr Arg Gly Asp Thr Ser Tyr Ala Asn Trp Ala Lys Gly
                   50                  55                  60

Arg Phe Thr Ile Ser Lys Thr Ser Thr Thr Val Asp Leu Lys Met Thr
            65                  70                  75                  80

Ser Leu Thr Thr Glu Asp Thr Ala Thr Tyr Phe Cys Val His Gly Tyr
                               85                  90                  95

Asn Pro Cys Lys Leu Trp Gly Gln Gly Thr Leu Val Thr Val Ser
                          100                 105                 110

<210> SEQ ID NO 5
<211> LENGTH: 330
<212> TYPE: DNA
<213> ORGANISM: Artificial Sequence
<220> FEATURE:
<223> OTHER INFORMATION: derived from rabbit

<400> SEQUENCE: 5
gcctatgata tgacccagac tccagcctct gtggaggtag ctgtgggagg cacagtcacc      60
atcaattgcc aggccagtga gagcattaac actgcattag cctggtatca gcagaaacca     120
ggacagcctc ccaaggtcct gatctatgct gcctccgatc tggcatctgg ggtcccatcg     180
cggttcaaag gcagtggatc tgggaaacag ttcactctca ccatcagcgg cgtgcagtgt     240
gccgatgctg ccacttacta ctgtcaacag ggttatactg caaataatat tgataatgct     300
ttcggcggag ggaccgaggt ggtcgtcaaa                                      330

<210> SEQ ID NO 6
<211> LENGTH: 333
<212> TYPE: DNA
<213> ORGANISM: Artificial Sequence
<220> FEATURE:
```

<223> OTHER INFORMATION: derived from rabbit

<400> SEQUENCE: 6

```
cagtcggtgg aggagtccgg gggtcgcctg gtcgcgcctg ggacacccct gacactcacc      60
tgcacagtct ctggaatcga cctcagtagg aatgcaatga cctgggtccg ccaggctcca     120
gggaagggc tggaatacat cgcatatatt aatactaggg gtggcgcatc ctacgcgaac     180
tgggcgaaag gccgattcac catctccaaa acctcgacca cggtggatct gaaaatgacc     240
agtctgacag cttcagacac ggccacctat ttctgtgtca atggttataa cccctgtaag     300
ttgtggggcc cggggaccct cgtcaccgtc tcg                                   333
```

<210> SEQ ID NO 7
<211> LENGTH: 110
<212> TYPE: PRT
<213> ORGANISM: Artificial Sequence
<220> FEATURE:
<223> OTHER INFORMATION: derived from rabbit

<400> SEQUENCE: 7

```
Ala Tyr Asp Met Thr Gln Thr Pro Ala Ser Val Glu Val Ala Val Gly
1               5                   10                  15

Gly Thr Val Thr Ile Asn Cys Gln Ala Ser Glu Ser Ile Asn Thr Ala
            20                  25                  30

Leu Ala Trp Tyr Gln Gln Lys Pro Gly Gln Pro Pro Lys Val Leu Ile
        35                  40                  45

Tyr Ala Ala Ser Asp Leu Ala Ser Gly Val Pro Ser Arg Phe Lys Gly
    50                  55                  60

Ser Gly Ser Gly Lys Gln Phe Thr Leu Thr Ile Ser Gly Val Gln Cys
65                  70                  75                  80

Ala Asp Ala Ala Thr Tyr Tyr Cys Gln Gln Gly Tyr Thr Ala Asn Asn
                85                  90                  95

Ile Asp Asn Ala Phe Gly Gly Gly Thr Glu Val Val Val Lys
            100                 105                 110
```

<210> SEQ ID NO 8
<211> LENGTH: 111
<212> TYPE: PRT
<213> ORGANISM: Artificial Sequence
<220> FEATURE:
<223> OTHER INFORMATION: derived from rabbit

<400> SEQUENCE: 8

```
Gln Ser Val Glu Glu Ser Gly Gly Arg Leu Val Ala Pro Gly Thr Pro
1               5                   10                  15

Leu Thr Leu Thr Cys Thr Val Ser Gly Ile Asp Leu Ser Arg Asn Ala
            20                  25                  30

Met Thr Trp Val Arg Gln Ala Pro Gly Lys Gly Leu Glu Tyr Ile Ala
        35                  40                  45

Tyr Ile Asn Thr Arg Gly Gly Ala Ser Tyr Ala Asn Trp Ala Lys Gly
    50                  55                  60

Arg Phe Thr Ile Ser Lys Thr Ser Thr Thr Val Asp Leu Lys Met Thr
65                  70                  75                  80

Ser Leu Thr Ala Ser Asp Thr Ala Thr Tyr Phe Cys Val Asn Gly Tyr
                85                  90                  95

Asn Pro Cys Lys Leu Trp Gly Pro Gly Thr Leu Val Thr Val Ser
            100                 105                 110
```

<210> SEQ ID NO 9
<211> LENGTH: 330
<212> TYPE: DNA
<213> ORGANISM: Artificial Sequence
<220> FEATURE:
<223> OTHER INFORMATION: derived from rabbit

<400> SEQUENCE: 9

```
gcccaagtgc tgacccagac tccatcttcc acgtctgcag ctgtgggagg cacagtcacc    60
atcaattgcc agtccagtca gaatgttgtt aataacaact ggttctcctg gtttcagcag   120
aaaccagggc agcctcccaa ggtcctgatc tattttgtat ccaaactggc atctggggtc   180
ccatcgcggt ttaaaggcag tggatctggg acacagttca ctctcaccat cagcgacctg   240
gagtgtgacg atgctgccac ttattattgt ggaggcggtt atagtgataa tatttatgcg   300
ttcggcggag ggaccgaggt ggtcgtcgaa                                    330
```

<210> SEQ ID NO 10
<211> LENGTH: 339
<212> TYPE: DNA
<213> ORGANISM: Artificial Sequence
<220> FEATURE:
<223> OTHER INFORMATION: derived from rabbit

<400> SEQUENCE: 10

```
cagtcggtgg aggagtccgg gggtcgcctg gtcacgcctg ggacacccct ggcactcacc    60
tgcacagtct ctggaatcga cctcagttac tatgcaataa gctgggtccg ccaggctcca   120
gggaaggggc tggaatacat cggaatcatt ggtagtagtg gtagaacata ctacgcgagc   180
tgggcgaaag gccgattcac catctccaaa acctcgacca cggtggatct gaaaatgacc   240
agtctgacaa ccgaagacac ggccacctat ttctgtgtca ggggtggtcc tacttctagt   300
cctagttttgt ggggccaagg caccctcgtc accgtctcg                         339
```

<210> SEQ ID NO 11
<211> LENGTH: 110
<212> TYPE: PRT
<213> ORGANISM: Artificial Sequence
<220> FEATURE:
<223> OTHER INFORMATION: derived from rabbit

<400> SEQUENCE: 11

```
Ala Gln Val Leu Thr Gln Thr Pro Ser Ser Thr Ser Ala Ala Val Gly
  1               5                  10                  15

Gly Thr Val Thr Ile Asn Cys Gln Ser Ser Gln Asn Val Val Asn Asn
             20                  25                  30

Asn Trp Phe Ser Trp Phe Gln Gln Lys Pro Gly Gln Pro Pro Lys Val
         35                  40                  45

Leu Ile Tyr Phe Val Ser Lys Leu Ala Ser Gly Val Pro Ser Arg Phe
     50                  55                  60

Lys Gly Ser Gly Ser Gly Thr Gln Phe Thr Leu Thr Ile Ser Asp Leu
 65                  70                  75                  80

Glu Cys Asp Asp Ala Ala Thr Tyr Tyr Cys Gly Gly Gly Tyr Ser Asp
                 85                  90                  95

Asn Ile Tyr Ala Phe Gly Gly Gly Thr Glu Val Val Val Glu
            100                 105                 110
```

<210> SEQ ID NO 12
<211> LENGTH: 113
<212> TYPE: PRT
<213> ORGANISM: Artificial Sequence
<220> FEATURE:
<223> OTHER INFORMATION: derived from rabbit

<400> SEQUENCE: 12

Gln Ser Val Glu Glu Ser Gly Gly Arg Leu Val Thr Pro Gly Thr Pro
1               5                   10                  15
Leu Ala Leu Thr Cys Thr Val Ser Gly Ile Asp Leu Ser Tyr Tyr Ala
            20                  25                  30
Ile Ser Trp Val Arg Gln Ala Pro Gly Lys Gly Leu Glu Tyr Ile Gly
        35                  40                  45
Ile Ile Gly Ser Ser Gly Arg Thr Tyr Tyr Ala Ser Trp Ala Lys Gly
    50                  55                  60
Arg Phe Thr Ile Ser Lys Thr Ser Thr Thr Val Asp Leu Lys Met Thr
65                  70                  75                  80
Ser Leu Thr Thr Glu Asp Thr Ala Thr Tyr Phe Cys Val Arg Gly Gly
                85                  90                  95
Pro Thr Ser Ser Pro Ser Leu Trp Gly Gln Gly Thr Leu Val Thr Val
            100                 105                 110
Ser

<210> SEQ ID NO 13
<211> LENGTH: 342
<212> TYPE: DNA
<213> ORGANISM: Artificial Sequence
<220> FEATURE:
<223> OTHER INFORMATION: derived from rabbit

<400> SEQUENCE: 13
gacatcgtga tgacccagac tccatcctcc gtgtctgcag ctgtgggagg cacagtcacc    60
atcaattgcc aggccagtca gagtgtttat gggaccaacc gtttatcctg gtatcagcag   120
aaaccagggc agcgtcccaa gctcctgatc tatggtgcat ccactctgac atctggggtc   180
ccatcgcggt tcaaaggcag tggatctggg acacagttca ctctcaccat cagtggcgtg   240
cagtgtgatg atgctgccac ttactactgt ctaggcggtt ggtttgaaag tagtagtagt   300
cttgattggg ctttcggcgg agggaccgag gtggtcgtcg aa                     342

<210> SEQ ID NO 14
<211> LENGTH: 348
<212> TYPE: DNA
<213> ORGANISM: Artificial Sequence
<220> FEATURE:
<223> OTHER INFORMATION: derived from rabbit

<400> SEQUENCE: 14
cagtcggtgg aggagtccgg gggtcgcctg gtcgcgcctg gacacccct gacactcacc     60
tgtacagtct ctggaatcga cctcagtaga aatgcaatgg gctgggtccg ccaggctcca   120
gagaaggggc tggaatacat cggccatatt gcgagtcgtg gtaacatatg gttcaggaac   180
tgggcgaaag gccgattcac cgtctccaaa acctcgacca cggtggatct aaaaatcacc   240
agtccgacaa ccgaggacac ggccacctat ttctgtggca gatttcttgt agtatctggg   300
gtggggactt tgatccctg gggccagggg accctcgtca ccgtctcg                348

<210> SEQ ID NO 15
<211> LENGTH: 114
<212> TYPE: PRT
<213> ORGANISM: Artificial Sequence
<220> FEATURE:
<223> OTHER INFORMATION: derived from rabbit

<400> SEQUENCE: 15

Asp Ile Val Met Thr Gln Thr Pro Ser Ser Val Ala Ala Val Gly
1               5                   10                  15

Gly Thr Val Thr Ile Asn Cys Gln Ala Ser Gln Ser Val Tyr Gly Thr
            20                  25                  30

Asn Arg Leu Ser Trp Tyr Gln Gln Lys Pro Gly Gln Arg Pro Lys Leu
        35                  40                  45

Leu Ile Tyr Gly Ala Ser Thr Leu Thr Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Gly Trp Phe Glu
                85                  90                  95

Ser Ser Ser Ser Leu Asp Trp Ala Phe Gly Gly Gly Thr Glu Val Val
            100                 105                 110

Val Glu

<210> SEQ ID NO 16
<211> LENGTH: 116
<212> TYPE: PRT
<213> ORGANISM: Artificial Sequence
<220> FEATURE:
<223> OTHER INFORMATION: derived from rabbit

<400> SEQUENCE: 16

Gln Ser Val Glu Glu Ser Gly Gly Arg Leu Val Ala Pro Gly Thr Pro
1               5                   10                  15

Leu Thr Leu Thr Cys Thr Val Ser Gly Ile Asp Leu Ser Arg Asn Ala
            20                  25                  30

Met Gly Trp Val Arg Gln Ala Pro Glu Lys Gly Leu Glu Tyr Ile Gly
        35                  40                  45

His Ile Ala Ser Arg Gly Asn Ile Trp Phe Arg Asn Trp Ala Lys Gly
    50                  55                  60

Arg Phe Thr Val Ser Lys Thr Ser Thr Thr Val Asp Leu Lys Ile Thr
65                  70                  75                  80

Ser Pro Thr Thr Glu Asp Thr Ala Thr Tyr Phe Cys Gly Arg Phe Leu
                85                  90                  95

Val Val Ser Gly Val Gly Thr Phe Asp Pro Trp Gly Gln Gly Thr Leu
            100                 105                 110

Val Thr Val Ser
        115

<210> SEQ ID NO 17
<211> LENGTH: 336
<212> TYPE: DNA
<213> ORGANISM: Artificial Sequence
<220> FEATURE:
<223> OTHER INFORMATION: derived from rabbit

<400> SEQUENCE: 17
gcagccgtgc tgacccagac tccatcgtcc gtgtctgcag ctgtgggagg cacagtcacc        60
atcaagtgcc agtccagtca gagtgtttat aataacaacg aatttcctg gtatcagcag        120 aaaccagggc agcctcccaa gctcctgatc tatgatgcat ccaaattggc atctggggtc      180
ccatcgcggt tcagcggcag tggatctggg acacagttca ctctcaccat cagcggcgtg      240
cagtgtgacg atgttgccac ttattactgt ctaggcggtt ataatgatga tactaataga      300

```
tgggctttcg gcggagggac cgaggtggtg gtcgaa                              336
```

<210> SEQ ID NO 18
<211> LENGTH: 351
<212> TYPE: DNA
<213> ORGANISM: Artificial Sequence
<220> FEATURE:
<223> OTHER INFORMATION: derived from rabbit

<400> SEQUENCE: 18

```
cagtcgctgg aggagtccgg gggtcgcctg gtcacgcctg ggacacccct gacactcacc    60
tgcacagtct ctggattctc cctcagtcgc tactggatga gctgggtccg ccaggctcca   120
gggaaggggc tggagtggat cggaaacatt ggtggtggta gtggtagtac attatacgcg   180
ccctgggcaa aaggccgatc caccatctcc aaaacctcga ccacggtgga tctgaaaatc   240
accagtccga caaccgagga cacggccacc tatttctgtg cagatatgt taaaaatggt    300
ggtggttatc ggttggatct ttggggccca gggaccctgg tcaccgtctc g            351
```

<210> SEQ ID NO 19
<211> LENGTH: 112
<212> TYPE: PRT
<213> ORGANISM: Artificial Sequence
<220> FEATURE:
<223> OTHER INFORMATION: derived from rabbit

<400> SEQUENCE: 19

```
Ala Ala Val Leu Thr Gln Thr Pro Ser Ser Val Ser Ala Ala Val Gly
1               5                   10                  15
Gly Thr Val Thr Ile Lys Cys Gln Ser Ser Gln Ser Val Tyr Asn Asn
            20                  25                  30
Asn Glu Phe Ser Trp Tyr Gln Gln Lys Pro Gly Gln Pro Pro Lys Leu
        35                  40                  45
Leu Ile Tyr Asp Ala Ser Lys Leu Ala Ser Gly Val Pro Ser Arg Phe
    50                  55                  60
Ser Gly Ser Gly Ser Gly Thr Gln Phe Thr Leu Thr Ile Ser Gly Val
65                  70                  75                  80
Gln Cys Asp Asp Val Ala Thr Tyr Tyr Cys Leu Gly Gly Tyr Asn Asp
                85                  90                  95
Asp Thr Asn Arg Trp Ala Phe Gly Gly Gly Thr Glu Val Val Val Glu
            100                 105                 110
```

<210> SEQ ID NO 20
<211> LENGTH: 117
<212> TYPE: PRT
<213> ORGANISM: Artificial Sequence
<220> FEATURE:
<223> OTHER INFORMATION: derived from rabbit

<400> SEQUENCE: 20

```
Gln Ser Leu Glu Glu Ser Gly Gly Arg Leu Val Thr Pro Gly Thr Pro
1               5                   10                  15
Leu Thr Leu Thr Cys Thr Val Ser Gly Phe Ser Leu Ser Arg Tyr Trp
            20                  25                  30
Met Ser Trp Val Arg Gln Ala Pro Gly Lys Gly Leu Glu Trp Ile Gly
        35                  40                  45
Asn Ile Gly Gly Gly Ser Gly Ser Thr Leu Tyr Ala Pro Trp Ala Lys
    50                  55                  60
Gly Arg Ser Thr Ile Ser Lys Thr Ser Thr Thr Val Asp Leu Lys Ile
```

```
                65                  70                  75                  80
Thr Ser Pro Thr Thr Glu Asp Thr Ala Thr Tyr Phe Cys Gly Arg Tyr
                    85                  90                  95

Val Lys Asn Gly Gly Gly Tyr Arg Leu Asp Leu Trp Gly Pro Gly Thr
                100                 105                 110

Leu Val Thr Val Ser
        115
```

<210> SEQ ID NO 21
<211> LENGTH: 336
<212> TYPE: DNA
<213> ORGANISM: Artificial Sequence
<220> FEATURE:
<223> OTHER INFORMATION: derived from rabbit

<400> SEQUENCE: 21

```
gccatcgtga tgacccagac tccatcttcc aagtctgtcc ctgtgggaga cacagtcacc    60
atcaattgcc aggccagtga gagtgttgct aataacaact ggttagcctg gtttcaacag   120
aaaccagggc agcctcccaa gctcctgatc tacaaggcat ccactctggc atctggggtc   180
tcatcgcggt ttaaaggcag tggatctggg acacagttca ctctcaccat cggcgatgtg   240
gtgtgtgacg atgctgccac ttactattgt gcaggatata aaagtagtac tactgatgct   300
gttgctttcg gcggagggac cgaggtggtg gtcaaa                              336
```

<210> SEQ ID NO 22
<211> LENGTH: 342
<212> TYPE: DNA
<213> ORGANISM: Artificial Sequence
<220> FEATURE:
<223> OTHER INFORMATION: derived from rabbit

<400> SEQUENCE: 22

```
cagtcagtga aggagtccga gggaggtctc ttcaagccaa cggatacccct gacactcacc    60
tgcacagtct ctggattctc cctcagtagc tatgcaataa gctgggtccg ccaggctcca   120
gggaacgggc tggaatggat cggattcatt aacactatta ctggtggcac aaactacgcg   180
agctgggcga aaagccgatc caccatcacc agaaacacca cgataacac ggtgactctg    240
aaaatgacca gtctgacagc cgcggacacg gccacgtatt tctgtgcgag aagtggtgcc   300
tactttgact gtggggccc aggcaccctg gtcaccgtct cg                       342
```

<210> SEQ ID NO 23
<211> LENGTH: 112
<212> TYPE: PRT
<213> ORGANISM: Artificial Sequence
<220> FEATURE:
<223> OTHER INFORMATION: derived from rabbit

<400> SEQUENCE: 23

```
Ala Ile Val Met Thr Gln Thr Pro Ser Ser Lys Ser Val Pro Val Gly
  1               5                  10                  15

Asp Thr Val Thr Ile Asn Cys Gln Ala Ser Glu Ser Val Ala Asn Asn
                20                  25                  30

Asn Trp Leu Ala Trp Phe Gln Gln Lys Pro Gly Gln Pro Pro Lys Leu
            35                  40                  45

Leu Ile Tyr Lys Ala Ser Thr Leu Ala Ser Gly Val Ser Ser Arg Phe
        50                  55                  60

Lys Gly Ser Gly Ser Gly Thr Gln Phe Thr Leu Thr Ile Gly Asp Val
 65                 70                  75                  80
```

Val Cys Asp Asp Ala Ala Thr Tyr Tyr Cys Ala Gly Tyr Lys Ser Ser
            85                  90                  95

Thr Thr Asp Ala Val Ala Phe Gly Gly Gly Thr Glu Val Val Lys
        100                 105                 110

<210> SEQ ID NO 24
<211> LENGTH: 114
<212> TYPE: PRT
<213> ORGANISM: Artificial Sequence
<220> FEATURE:
<223> OTHER INFORMATION: derived from rabbit

<400> SEQUENCE: 24

Gln Ser Val Lys Glu Ser Glu Gly Gly Leu Phe Lys Pro Thr Asp Thr
1               5                   10                  15

Leu Thr Leu Thr Cys Thr Val Ser Gly Phe Ser Leu Ser Ser Tyr Ala
            20                  25                  30

Ile Ser Trp Val Arg Gln Ala Pro Gly Asn Gly Leu Glu Trp Ile Gly
        35                  40                  45

Phe Ile Asn Thr Ile Thr Gly Gly Thr Asn Tyr Ala Ser Trp Ala Lys
    50                  55                  60

Ser Arg Ser Thr Ile Thr Arg Asn Thr Asn Asp Asn Thr Val Thr Leu
65                  70                  75                  80

Lys Met Thr Ser Leu Thr Ala Ala Asp Thr Ala Thr Tyr Phe Cys Ala
                85                  90                  95

Arg Ser Gly Ala Tyr Phe Asp Leu Trp Gly Pro Gly Thr Leu Val Thr
            100                 105                 110

Val Ser

<210> SEQ ID NO 25
<211> LENGTH: 339
<212> TYPE: DNA
<213> ORGANISM: Artificial Sequence
<220> FEATURE:
<223> OTHER INFORMATION: derived from rabbit

<400> SEQUENCE: 25
gcccaagtgc tgacccagac tgcatccccc gtgtctgcgg ctgttggagg cacagtcacc      60
atcaattgcc agtccagtca gagtgtttat aagaacaacg acttagcctg gtatcagcag     120
aaaccagggc agcctcccaa gctcctgatc tattatgcat ccactctggc atctggggtc     180
tcatcgcggt tcaaaggcag tggatctggg acagagttca ctctcaccat cagcgacgcg     240
cagtgtgacg atgctgccac ttactactgt ctaggtagtt atgattgtag tagtgctgat     300
tgtaatgctt tcggcggagg gaccaaggtg gtcgtcaaa                            339

<210> SEQ ID NO 26
<211> LENGTH: 324
<212> TYPE: DNA
<213> ORGANISM: Artificial Sequence
<220> FEATURE:
<223> OTHER INFORMATION: derived from rabbit

<400> SEQUENCE: 26
cagtcggtgg aggagtccgg gggtcgcctg gtcacgcctg gacacccct gacactcacc       60 tgcacagtct ctggattctc cctcagtaac tatgcaatga gttgggtccg ccaggctcca     120
gggaaggggc tggaatggat cggaatcatt ggtaaaagtg gtagtacggc ctacgcgagc     180
tgggcgaaag gccgattcac catctccaga acctcgacca cggtggatct ggaaatcacc     240
agtccgacaa ccgaggacac ggccacctat ttctgtgtca gatttgtgct cttgtggggc    300
ccggggaccc tcgtcaccgt ctcg                                           324

<210> SEQ ID NO 27
<211> LENGTH: 113
<212> TYPE: PRT
<213> ORGANISM: Artificial Sequence
<220> FEATURE:
<223> OTHER INFORMATION: derived from rabbit

<400> SEQUENCE: 27

Ala Gln Val Leu Thr Gln Thr Ala Ser Pro Val Ser Ala Ala Val Gly
1               5                   10                  15

Gly Thr Val Thr Ile Asn Cys Gln Ser Ser Gln Ser Val Tyr Lys Asn
                20                  25                  30

Asn Asp Leu Ala Trp Tyr Gln Gln Lys Pro Gly Gln Pro Pro Lys Leu
            35                  40                  45

Leu Ile Tyr Tyr Ala Ser Thr Leu Ala Ser Gly Val Ser Ser Arg Phe
        50                  55                  60

Lys Gly Ser Gly Ser Gly Thr Glu Phe Thr Leu Thr Ile Ser Asp Ala
65                  70                  75                  80

Gln Cys Asp Asp Ala Ala Thr Tyr Tyr Cys Leu Gly Ser Tyr Asp Cys
                85                  90                  95

Ser Ser Ala Asp Cys Asn Ala Phe Gly Gly Gly Thr Lys Val Val Val
            100                 105                 110

Lys

<210> SEQ ID NO 28
<211> LENGTH: 108
<212> TYPE: PRT
<213> ORGANISM: Artificial Sequence
<220> FEATURE:
<223> OTHER INFORMATION: derived from rabbit

<400> SEQUENCE: 28

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
                20                  25                  30

Met Ser Trp Val Arg Gln Ala Pro Gly Lys Gly Leu Glu Trp Ile Gly
            35                  40                  45

Ile Ile Gly Lys Ser Gly Ser Thr Ala Tyr Ala Ser Trp Ala Lys Gly
        50                  55                  60

Arg Phe Thr Ile Ser Arg Thr Ser Thr Thr Val Asp Leu Glu Ile Thr
65                  70                  75                  80

Ser Pro Thr Thr Glu Asp Thr Ala Thr Tyr Phe Cys Val Arg Phe Val
                85                  90                  95

Leu Leu Trp Gly Pro Gly Thr Leu Val Thr Val Ser
            100                 105

<210> SEQ ID NO 29
<211> LENGTH: 330
<212> TYPE: DNA
<213> ORGANISM: Artificial Sequence
<220> FEATURE:
<223> OTHER INFORMATION: derived from rabbit

<400> SEQUENCE: 29

```
gcgcaagtgc tgacccagac tccatcctcc gtgtctgcag ctgtgggagg cacagtcacc    60
atcaattgcc agtccagtca gagtgttaat aacaacaact tcttatcctg gtatcagcag   120
aaaccagggc agcctcccaa gcaactgatc tacagggctt ccactctggc atctggggtc   180
ccatcgcggt tcaaaggcag tggatctggg acacagttca ctctcaccat cagcgacgtg   240
cagtgtgacg atgctgccac ttacttctgt gcaggcggtt atagtggtaa tatttatgct   300
ttcggcggag ggaccgaggt ggtggtcgaa                                     330

<210> SEQ ID NO 30
<211> LENGTH: 339
<212> TYPE: DNA
<213> ORGANISM: Artificial Sequence
<220> FEATURE:
<223> OTHER INFORMATION: derived from rabbit

<400> SEQUENCE: 30
cagtcggtgg aggagtccgg gggtcgcctg gtcacgcctg ggacacccct gacactcacc    60
tgcacagtct ctgaattctc cctcagtgac tatataataa actgggtccg ccaggctcca   120
gggaaggggc tggaatggat cgggatcatg ggtactagtg gtaccgcata ctacgcgagc   180
tgggcgaaag gccgattcac catctccaaa acctcgtcga ccacggtgga tctgagaatg   240
accagtctga aaccgaggac acggccacc tatttctgtg ccagagggg gtgttgctact   300 tctaatttct ggggccaagg caccctggtc accgtctcg                          339

<210> SEQ ID NO 31
<211> LENGTH: 110
<212> TYPE: PRT
<213> ORGANISM: Artificial Sequence
<220> FEATURE:
<223> OTHER INFORMATION: derived from rabbit

<400> SEQUENCE: 31

Ala Gln Val Leu Thr Gln Thr Pro Ser Ser Val Ser Ala Ala Val Gly
1               5                   10                  15

Gly Thr Val Thr Ile Asn Cys Gln Ser Ser Gln Ser Val Asn Asn Asn
            20                  25                  30

Asn Phe Leu Ser Trp Tyr Gln Gln Lys Pro Gly Gln Pro Pro Lys Gln
        35                  40                  45

Leu Ile Tyr Arg Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Phe Cys Ala Gly Gly Tyr Ser Gly
                85                  90                  95

Asn Ile Tyr Ala Phe Gly Gly Gly Thr Glu Val Val Val Glu
            100                 105                 110

<210> SEQ ID NO 32
<211> LENGTH: 113
<212> TYPE: PRT
<213> ORGANISM: Artificial Sequence
<220> FEATURE:
<223> OTHER INFORMATION: derived from rabbit

<400> SEQUENCE: 32

Gln Ser Val Glu Glu Ser Gly Gly Arg Leu Val Thr Pro Gly Thr Pro
1               5                   10                  15

Leu Thr Leu Thr Cys Thr Val Ser Glu Phe Ser Leu Ser Asp Tyr Ile
```

```
                20                 25                  30

Ile Asn Trp Val Arg Gln Ala Pro Gly Lys Gly Leu Glu Trp Ile Gly
            35                  40                  45

Ile Met Gly Thr Ser Gly Thr Ala Tyr Tyr Ala Ser Trp Ala Lys Gly
         50                  55                  60

Arg Phe Thr Ile Ser Lys Thr Ser Ser Thr Thr Val Asp Leu Arg Met
65                  70                  75                  80

Thr Ser Leu Thr Thr Glu Asp Thr Ala Thr Tyr Phe Cys Ala Arg Gly
                85                  90                  95

Gly Val Ala Thr Ser Asn Phe Trp Gly Gln Gly Thr Leu Val Thr Val
               100                 105                 110

Ser

<210> SEQ ID NO 33
<211> LENGTH: 330
<212> TYPE: DNA
<213> ORGANISM: Artificial Sequence
<220> FEATURE:
<223> OTHER INFORMATION: derived from rabbit

<400> SEQUENCE: 33
gcccaagtgc tgacccagac tgcatcccct gtgtctgcag ctgtgggagg cacagtcacc     60
atcaattgtc agtccagtca gagcgtttat ggtaacaatt ggttaggctg gtatcagcag    120
aaaccagggc agcctcccaa gctcctgatc tattctgcat ctactctggc atctggggtc    180
ccatcgcggt tcagtggcag tggatctggg acacagttca ctctcaccat cagcgacctg    240
gagtgtgacg atggtgccac ttactattgt gtaggcgggt atagtggtaa tattcatgtt    300
ttcggcggag ggaccaaggt ggtggtcgaa                                     330

<210> SEQ ID NO 34
<211> LENGTH: 339
<212> TYPE: DNA
<213> ORGANISM: Artificial Sequence
<220> FEATURE:
<223> OTHER INFORMATION: derived from rabbit

<400> SEQUENCE: 34
cagtcggtgg aggagtccgg gggtcgcctg gtcacgcctg gacacccct gacactcacc      60 tgcacagtct ctggattctc cctcaacgac tacgacatga gctgggtccg ccaggctcca    120
gggaaggggc tggaatggat cacaaccatt tatgttagtg gtaacacata ctacgcgacc    180
tgggcgaaag gccgattcac catctccaaa acctcgacca cggtggatct gaaaatgacc    240
agtccgacag ccgaggacac ggccacctat ttctgtgcca gagcggttcc tggtagtggt    300
aaggggttgt ggggcccggg caccctcgtc accgtctcg                           339

<210> SEQ ID NO 35
<211> LENGTH: 110
<212> TYPE: PRT
<213> ORGANISM: Artificial Sequence
<220> FEATURE:
<223> OTHER INFORMATION: derived from rabbit

<400> SEQUENCE: 35

Ala Gln Val Leu Thr Gln Thr Ala Ser Pro Val Ser Ala Ala Val Gly
1               5                  10                  15

Gly Thr Val Thr Ile Asn Cys Gln Ser Ser Gln Ser Val Tyr Gly Asn
            20                  25                  30
```

Asn Trp Leu Gly Trp Tyr Gln Gln Lys Pro Gly Gln Pro Pro Lys Leu
                35                  40                  45

Leu Ile Tyr Ser Ala Ser Thr Leu Ala Ser Gly Val Pro Ser Arg Phe
     50                  55                  60

Ser Gly Ser Gly Ser Gly Thr Gln Phe Thr Leu Thr Ile Ser Asp Leu
65                  70                  75                  80

Glu Cys Asp Asp Gly Ala Thr Tyr Tyr Cys Val Gly Tyr Ser Gly
                85                  90                  95

Asn Ile His Val Phe Gly Gly Gly Thr Lys Val Val Val Glu
            100                 105                 110

<210> SEQ ID NO 36
<211> LENGTH: 113
<212> TYPE: PRT
<213> ORGANISM: Artificial Sequence
<220> FEATURE:
<223> OTHER INFORMATION: derived from rabbit

<400> SEQUENCE: 36

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asp Tyr Asp
            20                  25                  30

Met Ser Trp Val Arg Gln Ala Pro Gly Lys Gly Leu Glu Trp Ile Thr
        35                  40                  45

Thr Ile Tyr Val Ser Gly Asn Thr Tyr Tyr Ala Thr Trp Ala Lys Gly
     50                  55                  60

Arg Phe Thr Ile Ser Lys Thr Ser Thr Thr Val Asp Leu Lys Met Thr
65                  70                  75                  80

Ser Pro Thr Ala Glu Asp Thr Ala Thr Tyr Phe Cys Ala Arg Ala Val
                85                  90                  95

Pro Gly Ser Gly Lys Gly Leu Trp Gly Pro Gly Thr Leu Val Thr Val
            100                 105                 110

Ser

<210> SEQ ID NO 37
<211> LENGTH: 339
<212> TYPE: DNA
<213> ORGANISM: Artificial Sequence
<220> FEATURE:
<223> OTHER INFORMATION: derived from rabbit

<400> SEQUENCE: 37
gcccaagtgc tgacccagac tgcatcgccc gtgtctgcag ctgtgggaaa cacagtcacc        60
atcacttgcc agtccagtca gagtgtttgg aagaataacg acttatcctg gtatcagcag       120
aaactagggc agcctcccaa gctcctgatc tattatgcat ccactctggc atctggggtc       180
tcatcgcggt tcaaagccag tggatctggg acacagttca ctctcaccat cagcgacgtg       240
caatgtgacg atgctggcac ttactactgt gtaggcagtt atgattgtag tagtgctgat       300
tgtaatgctt tcggcggagg gaccaaggtg gtcgtcaaa                              339

<210> SEQ ID NO 38
<211> LENGTH: 333
<212> TYPE: DNA
<213> ORGANISM: Artificial Sequence
<220> FEATURE:
<223> OTHER INFORMATION: derived from rabbit

<400> SEQUENCE: 38

```
cagtcgctgg aggagtccgg gggtcgcctg gtcacgccgg agacacccct gacactcacc    60
tgcacagcct ctggaatcga cctcagtaag tggccaatga cctgggtccg ccaggctcca   120
gggaagggac tggagtggat cggaattatt ggtaggagtg gtagcacgaa ttacgcgagc   180
tgggcgaaag gccgattcac catctccaaa acctcgacca cggtggatct gaaaatgacc   240
agtccgacaa ccgaggacac ggccacttat ttctgtgcca gaggtggtag ttattatgat   300
ttgtggggcc aggggaccct ggtcaccgtc tcg                                333
```

<210> SEQ ID NO 39
<211> LENGTH: 113
<212> TYPE: PRT
<213> ORGANISM: Artificial Sequence
<220> FEATURE:
<223> OTHER INFORMATION: derived from rabbit

<400> SEQUENCE: 39

```
Ala Gln Val Leu Thr Gln Thr Ala Ser Pro Val Ser Ala Ala Val Gly
1               5                   10                  15

Asn Thr Val Thr Ile Thr Cys Gln Ser Ser Gln Ser Val Trp Lys Asn
            20                  25                  30

Asn Asp Leu Ser Trp Tyr Gln Gln Lys Leu Gly Gln Pro Pro Lys Leu
        35                  40                  45

Leu Ile Tyr Tyr Ala Ser Thr Leu Ala Ser Gly Val Ser Ser Arg Phe
    50                  55                  60

Lys Ala Ser Gly Ser Gly Thr Gln Phe Thr Leu Thr Ile Ser Asp Val
65                  70                  75                  80

Gln Cys Asp Asp Ala Gly Thr Tyr Tyr Cys Val Gly Ser Tyr Asp Cys
                85                  90                  95

Ser Ser Ala Asp Cys Asn Ala Phe Gly Gly Gly Thr Lys Val Val Val
            100                 105                 110

Lys
```

<210> SEQ ID NO 40
<211> LENGTH: 111
<212> TYPE: PRT
<213> ORGANISM: Artificial Sequence
<220> FEATURE:
<223> OTHER INFORMATION: derived from rabbit

<400> SEQUENCE: 40

```
Gln Ser Leu Glu Glu Ser Gly Gly Arg Leu Val Thr Pro Gly Thr Pro
1               5                   10                  15

Leu Thr Leu Thr Cys Thr Ala Ser Gly Ile Asp Leu Ser Lys Trp Pro
            20                  25                  30

Met Thr Trp Val Arg Gln Ala Pro Gly Lys Gly Leu Glu Trp Ile Gly
        35                  40                  45

Ile Ile Gly Arg Ser Gly Ser Thr Asn Tyr Ala Ser Trp Ala Lys Gly
    50                  55                  60

Arg Phe Thr Ile Ser Lys Thr Ser Thr Thr Val Asp Leu Lys Met Thr
65                  70                  75                  80

Ser Pro Thr Thr Glu Asp Thr Ala Thr Tyr Phe Cys Ala Arg Gly Gly
                85                  90                  95

Ser Tyr Tyr Asp Leu Trp Gly Gln Gly Thr Leu Val Thr Val Ser
            100                 105                 110
```

<210> SEQ ID NO 41

<211> LENGTH: 339
<212> TYPE: DNA
<213> ORGANISM: Artificial Sequence
<220> FEATURE:
<223> OTHER INFORMATION: derived from rabbit

<400> SEQUENCE: 41

```
gccgccgtgc tgacccagac tccatctccc gtgtctgcag ctgtgggagg cacagtcagc    60
atcagttgcc agtccagtca gagtgttgat aataacaact acttatcctg gtatcagcag   120
aaaccagggc agcctcccaa gctcctgatc tatgatgcat ccgatctggc atctggggtc   180
ccatcgcggt tcaaaggcag tggatctggg acacagttca ctctcaccat cagcgacgtg   240
cagtgtgacg atgctgccac ttactactgt gcaggcggtt atataactag tagtgatatt   300
ttttatgatt tcggcggagg gaccaaggtg gtggtcaaa                          339
```

<210> SEQ ID NO 42
<211> LENGTH: 324
<212> TYPE: DNA
<213> ORGANISM: Artificial Sequence
<220> FEATURE:
<223> OTHER INFORMATION: derived from rabbit

<400> SEQUENCE: 42

```
cagtcggtgg aggagtccgg gggtcgcctg gtcacgcctg ggacacccct gacactcacc    60
tgcacagtct ctggattctc cctcagtacc tatgcaatga gctgggtccg ccaggctcca   120
gggaaggggc tggaatggat cggaatcgtt ggaagagtg gtattataaa gtacgcgagc   180
tgggcgaaag gccggttcac catctccaaa acctcgacca cggtggatct gaaaatgacc   240
agtctgacaa ccgaggacac ggccatttat ttctgtgcca gactatggag cttgtggggc   300
caagggaccc tcgtcaccgt ctcg                                          324
```

<210> SEQ ID NO 43
<211> LENGTH: 113
<212> TYPE: PRT
<213> ORGANISM: Artificial Sequence
<220> FEATURE:
<223> OTHER INFORMATION: derived from rabbit

<400> SEQUENCE: 43

```
Ala Ala Val Leu Thr Gln Thr Pro Ser Pro Val Ser Ala Ala Val Gly
1               5                   10                  15

Gly Thr Val Ser Ile Ser Cys Gln Ser Ser Gln Ser Val Asp Asn Asn
            20                  25                  30

Asn Tyr Leu Ser Trp Tyr Gln Gln Lys Pro Gly Gln Pro Pro Lys Leu
        35                  40                  45

Leu Ile Tyr Asp Ala Ser Asp Leu Ala Ser Gly Val Pro Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Ala Gly Gly Tyr Ile Thr
                85                  90                  95

Ser Ser Asp Ile Phe Tyr Asp Phe Gly Gly Gly Thr Lys Val Val Val
            100                 105                 110

Lys
```

<210> SEQ ID NO 44
<211> LENGTH: 108
<212> TYPE: PRT

<213> ORGANISM: Artificial Sequence
<220> FEATURE:
<223> OTHER INFORMATION: derived from rabbit

<400> SEQUENCE: 44

```
Gln Ser Val Glu Glu Ser Gly Gly Arg Leu Val Thr Pro Gly Thr Pro
1               5                   10                  15
Leu Thr Leu Thr Cys Thr Val Ser Gly Phe Ser Leu Ser Thr Tyr Ala
            20                  25                  30
Met Ser Trp Val Arg Gln Ala Pro Gly Lys Gly Leu Glu Trp Ile Gly
        35                  40                  45
Ile Val Gly Lys Ser Gly Ile Ile Lys Tyr Ala Ser Trp Ala Lys Gly
    50                  55                  60
Arg Phe Thr Ile Ser Lys Thr Ser Thr Val Asp Leu Lys Met Thr
65                  70                  75                  80
Ser Leu Thr Thr Glu Asp Thr Ala Ile Tyr Phe Cys Ala Arg Leu Trp
            85                  90                  95
Ser Leu Trp Gly Gln Gly Thr Leu Val Thr Val Ser
            100                 105
```

<210> SEQ ID NO 45
<211> LENGTH: 330
<212> TYPE: DNA
<213> ORGANISM: Artificial Sequence
<220> FEATURE:
<223> OTHER INFORMATION: derived from rabbit

<400> SEQUENCE: 45

```
gacattgtga tgacccagac tccagcctcc gtgtctgaac ctgtgggagg cacagtcacc     60
atcaagtgcc aggccagtca gagcattagc aactggttag cctggtatca gcagaaacca   120
gggcagcctc ccaagctcct gatctacagg gcatccactc tggcatctgg gtctcatcg    180
cggttcaaag gcagtggatc tgggacagag ttcactctca ccatcagcga cctggagtgt   240
gccgatgctg ccacttacta ctgtcaaagc gattatggta tagatactta tggaagtgct   300
ttcggcggag ggaccaaggt ggtggtcaaa                                     330
```

<210> SEQ ID NO 46
<211> LENGTH: 354
<212> TYPE: DNA
<213> ORGANISM: Artificial Sequence
<220> FEATURE:
<223> OTHER INFORMATION: derived from rabbit

<400> SEQUENCE: 46

```
cagtcgctgg aggagtcccg gggtcgcctg gtcacgcctg gacacccct gacactcacc      60
tgcacagtct ctggaatcga cctcagtagt tatgcaatga cctgggtccg ccaggctcca   120
gggaaggggc tggaatggat cggaatggtt cgtcgtagtg gtaccacata ctacgcgagc   180
tgggcgaaag gccgattcac catctccaaa acctcgacca cggtggatct gaaaatcatc   240
agtccgacaa ccgaggacac ggccacctat ttctgtgcca gatgtgataa tagtgctggt   300
gactggagtt acggcatgga cctctggggc cggggacccc tggtcaccgt ctcg         354
```

<210> SEQ ID NO 47
<211> LENGTH: 110
<212> TYPE: PRT
<213> ORGANISM: Artificial Sequence
<220> FEATURE:
<223> OTHER INFORMATION: derived from rabbit

<400> SEQUENCE: 47

Asp Ile Val Met Thr Gln Thr Pro Ala Ser Val Ser Glu Pro Val Gly
1               5                   10                  15

Gly Thr Val Thr Ile Lys Cys Gln Ala Ser Gln Ser Ile Ser Asn Trp
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Asp Tyr Gly Ile Asp Thr
                85                  90                  95

Tyr Gly Ser Ala Phe Gly Gly Gly Thr Lys Val Val Val Lys
            100                 105                 110

<210> SEQ ID NO 48
<211> LENGTH: 118
<212> TYPE: PRT
<213> ORGANISM: Artificial Sequence
<220> FEATURE:
<223> OTHER INFORMATION: derived from rabbit

<400> SEQUENCE: 48

Gln Ser Leu Glu Glu Ser Arg Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30

Met Thr Trp Val Arg Gln Ala Pro Gly Lys Gly Leu Glu Trp Ile Gly
        35                  40                  45

Met Val Arg Arg Ser Gly Thr Thr Tyr Tyr Ala Ser Trp Ala Lys Gly
    50                  55                  60

Arg Phe Thr Ile Ser Lys Thr Ser Thr Thr Val Asp Leu Lys Ile Ile
65                  70                  75                  80

Ser Pro Thr Thr Glu Asp Thr Ala Thr Tyr Phe Cys Ala Arg Cys Asp
                85                  90                  95

Asn Ser Ala Gly Asp Trp Ser Tyr Gly Met Asp Leu Trp Gly Pro Gly
            100                 105                 110

Thr Leu Val Thr Val Ser
        115

<210> SEQ ID NO 49
<211> LENGTH: 339
<212> TYPE: DNA
<213> ORGANISM: Artificial Sequence
<220> FEATURE:
<223> OTHER INFORMATION: derived from rabbit

<400> SEQUENCE: 49
gcccaagtgc tgacccagac tgcatcgccc gtgtctgcag ctgtgggaag cacagtcacc    60
atcaattgcc aggccagtca gagtgtttat cagaacaact acttagcctg gtttcagcag   120
aaaccagggc agcctcccaa gcgcctgatc tattctgcat ccactctggc atctggggtc   180
tcatcgcggt tcaaaggcag tggatctggg acacagttca ctctcaccat cagcgacgtg   240
cagtgtgacg atgctgccac ttattactgt ctgggcgcct atgattgtag tggtgttgat   300
tgtagtgctt tcggcggagg gaccaaggtg gtcgtcaaa                          339

<210> SEQ ID NO 50
<211> LENGTH: 342
<212> TYPE: DNA
<213> ORGANISM: Artificial Sequence
<220> FEATURE:
<223> OTHER INFORMATION: derived from rabbit

<400> SEQUENCE: 50

```
cagtcggtgg aggagtccgg gggtcgcctg gtcacgcctg ggacacccct gacactcacc      60
tgcaccgtct ctggattctc cctcagtacc aatgcaatga tctgggtccg ccaggctcca     120
gggaaggggc tggaatatat cggtgtgatt gctggtagtg gtagcacatc ttacgcgagc     180
tgggcgaaag gccgattcac catctccaaa acctcgacca cggtggatct gaaaatcacc     240
agtccgacaa ccgaggacac ggccacctat ttctgtgcca gagggggttg ggttagtggt     300
ccggagagct tgtggggcca aggcaccctc gtcaccgtct cg                        342
```

<210> SEQ ID NO 51
<211> LENGTH: 113
<212> TYPE: PRT
<213> ORGANISM: Artificial Sequence
<220> FEATURE:
<223> OTHER INFORMATION: derived from rabbit

<400> SEQUENCE: 51

```
Ala Gln Val Leu Thr Gln Thr Ala Ser Pro Val Ser Ala Ala Val Gly
1               5                   10                  15

Ser Thr Val Thr Ile Asn Cys Gln Ala Ser Gln Ser Val Tyr Gln Asn
            20                  25                  30

Asn Tyr Leu Ala Trp Phe Gln Gln Lys Pro Gly Gln Pro Pro Lys Arg
        35                  40                  45

Leu Ile Tyr Ser Ala Ser Thr Leu Ala Ser Gly Val Ser Ser Arg Phe
    50                  55                  60

Lys Gly Ser Gly Ser Gly Thr Gln Phe Thr Leu Thr Ile Ser Asp Val
65                  70                  75                  80

Gln Cys Asp Asp Ala Ala Thr Tyr Tyr Cys Leu Gly Ala Tyr Asp Cys
                85                  90                  95

Ser Gly Val Asp Cys Ser Ala Phe Gly Gly Thr Lys Val Val Val
            100                 105                 110

Lys
```

<210> SEQ ID NO 52
<211> LENGTH: 114
<212> TYPE: PRT
<213> ORGANISM: Artificial Sequence
<220> FEATURE:
<223> OTHER INFORMATION: derived from rabbit

<400> SEQUENCE: 52

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Asn Ala
            20                  25                  30

Met Ile Trp Val Arg Gln Ala Pro Gly Lys Gly Leu Glu Tyr Ile Gly
        35                  40                  45

Val Ile Ala Gly Ser Gly Ser Thr Ser Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80
```

Ser Pro Thr Thr Glu Asp Thr Ala Thr Tyr Phe Cys Ala Arg Gly Gly
                85                  90                  95

Trp Val Ser Gly Pro Glu Ser Leu Trp Gly Gln Gly Thr Leu Val Thr
            100                 105                 110

Val Ser

<210> SEQ ID NO 53
<211> LENGTH: 330
<212> TYPE: DNA
<213> ORGANISM: Artificial Sequence
<220> FEATURE:
<223> OTHER INFORMATION: derived from rabbit

<400> SEQUENCE: 53
gcccaagtgc tgacccagac tccatcttcc acgtctgcag ctgtgggagg cacagtcacc    60
atcagttgcc agtccagtcc gagtgtttat ggtaataact ggttaggctg gtatcagaag   120
aaaccagggc agcctcccaa gctcctgatc tattctgcat ccactctggc atctggggtc   180
tcatcgcggt ttaaaggcag tggatctggg acacagttca ctctcaccat cagcgacctg   240
gagtgtgacg atgctgccac ttactactgt gcaggcggtt atagtggtaa tattcatgtt   300
ttcggcggag ggaccaaggt ggtggtcaaa                                    330

<210> SEQ ID NO 54
<211> LENGTH: 339
<212> TYPE: DNA
<213> ORGANISM: Artificial Sequence
<220> FEATURE:
<223> OTHER INFORMATION: derived from rabbit

<400> SEQUENCE: 54
cagtcggtgg aggagtccgg gggtcgcctg gtcacgcctg ggacacccct gacactcacc    60
tgcacagtct ctggattctc cctcaataac tacgacatga cctgggtccg ccaggctcca   120
gggaaggggc tggaatggat cggaagtatt tttgttagtg gtaatatata ctacgcgagc   180
tgggcgaaag gccgattcac catctccaaa acctcgacca cggtggatct gaaaatgacc   240
agtccgacaa ccgaggacac ggccacctat ttctgtgcca gcaattct tggtagtagt   300 aaggggttgt ggggcccagg caccctggtc accgtctcg                         339

<210> SEQ ID NO 55
<211> LENGTH: 110
<212> TYPE: PRT
<213> ORGANISM: Artificial Sequence
<220> FEATURE:
<223> OTHER INFORMATION: derived from rabbit

<400> SEQUENCE: 55

Ala Gln Val Leu Thr Gln Thr Pro Ser Ser Thr Ser Ala Ala Val Gly
1               5                   10                  15

Gly Thr Val Thr Ile Ser Cys Gln Ser Ser Pro Ser Val Tyr Gly Asn
            20                  25                  30

Asn Trp Leu Gly Trp Tyr Gln Lys Lys Pro Gly Gln Pro Pro Lys Leu
        35                  40                  45

Leu Ile Tyr Ser Ala Ser Thr Leu Ala Ser Gly Val Ser Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Gly Tyr Ser Gly

```
                    85                  90                  95
Asn Ile His Val Phe Gly Gly Gly Thr Lys Val Val Lys
                100                 105                 110
```

<210> SEQ ID NO 56
<211> LENGTH: 113
<212> TYPE: PRT
<213> ORGANISM: Artificial Sequence
<220> FEATURE:
<223> OTHER INFORMATION: derived from rabbit

<400> SEQUENCE: 56

```
Gln Ser Val Glu Glu Ser Gly Gly Arg Leu Val Thr Pro Gly Thr Pro
1               5                   10                  15
Leu Thr Leu Thr Cys Thr Val Ser Gly Phe Ser Leu Asn Asn Tyr Asp
                20                  25                  30
Met Thr Trp Val Arg Gln Ala Pro Gly Lys Gly Leu Glu Trp Ile Gly
            35                  40                  45
Ser Ile Phe Val Ser Gly Asn Ile Tyr Tyr Ala Ser Trp Ala Lys Gly
        50                  55                  60
Arg Phe Thr Ile Ser Lys Thr Ser Thr Thr Val Asp Leu Lys Met Thr
65                  70                  75                  80
Ser Pro Thr Thr Glu Asp Thr Ala Thr Tyr Phe Cys Ala Arg Ala Ile
                85                  90                  95
Leu Gly Ser Ser Lys Gly Leu Trp Gly Pro Gly Thr Leu Val Thr Val
                100                 105                 110
Ser
```

<210> SEQ ID NO 57
<211> LENGTH: 330
<212> TYPE: DNA
<213> ORGANISM: Artificial Sequence
<220> FEATURE:
<223> OTHER INFORMATION: derived from rabbit

<400> SEQUENCE: 57

```
gcctatgata tgacccagac tccagcctct gtggaggtag ctgtgggagg cacagtcacc      60
atcaagtgcc aggccagtca gagcatttac agctatttag cctggtatca gcagaaacca    120
gggcagcctc ccaagctcct gatttattct gcatcctatc tagcatctgg ggtcccatcg    180
cggttcagcg gcagtggatc tgggacagag ttcactctca ccatcagcga cctggagtgt    240
gccgatgctg ccacttatta ctgtcaacac gggtacatta gtggtaatgt tgataatgct    300
ttcggcggag ggaccaaggt ggtcgtcaaa                                      330
```

<210> SEQ ID NO 58
<211> LENGTH: 339
<212> TYPE: DNA
<213> ORGANISM: Artificial Sequence
<220> FEATURE:
<223> OTHER INFORMATION: derived from rabbit

<400> SEQUENCE: 58

```
cagtcggtgg aggagtccgg gggtcgcctg gtcacgcctg ggacacccct gacactcacc      60
tgcacagtct ctggattctc cctcagcatc tacgacatga gctgggtccg ccaggctcca    120
gggaaggggc tggaatggat cggatccatt tatgttagtg gtaatatata ctacgcgagc    180
tgggcgaaag gccgattcac catctcccaa acctcgacca cggtggatct gaaaatgacc    240
agtccgacaa ccgaggacac ggccacctat ttctgtgcca gagcggttcc tggtagtagt    300
``` aagggggttgt ggggccaggg gaccctcgtc accgtctcg 339

<210> SEQ ID NO 59
<211> LENGTH: 110
<212> TYPE: PRT
<213> ORGANISM: Artificial Sequence
<220> FEATURE:
<223> OTHER INFORMATION: derived from rabbit

<400> SEQUENCE: 59

```
Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Tyr Ser Tyr
            20                  25                  30

Leu Ala Trp Tyr Gln Gln Lys Pro Gly Gln Pro Pro Lys Leu Leu Ile
        35                  40                  45

Tyr Ser Ala Ser Tyr Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln His Gly Tyr Ile Ser Gly Asn
                85                  90                  95

Val Asp Asn Ala Phe Gly Gly Gly Thr Lys Val Val Val Lys
            100                 105                 110
```

<210> SEQ ID NO 60
<211> LENGTH: 113
<212> TYPE: PRT
<213> ORGANISM: Artificial Sequence
<220> FEATURE:
<223> OTHER INFORMATION: derived from rabbit

<400> SEQUENCE: 60

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ile Tyr Asp
            20                  25                  30

Met Ser Trp Val Arg Gln Ala Pro Gly Lys Gly Leu Glu Trp Ile Gly
        35                  40                  45

Ser Ile Tyr Val Ser Gly Asn Ile Tyr Tyr Ala Ser Trp Ala Lys Gly
    50                  55                  60

Arg Phe Thr Ile Ser Lys Thr Ser Thr Val Asp Leu Lys Met Thr
65                  70                  75                  80

Ser Pro Thr Thr Glu Asp Thr Ala Thr Tyr Phe Cys Ala Arg Ala Val
                85                  90                  95

Pro Gly Ser Ser Lys Gly Leu Trp Gly Gln Gly Thr Leu Val Thr Val
            100                 105                 110

Ser
```

<210> SEQ ID NO 61
<211> LENGTH: 327
<212> TYPE: DNA
<213> ORGANISM: Artificial Sequence
<220> FEATURE:
<223> OTHER INFORMATION: derived from rabbit

<400> SEQUENCE: 61
gcgcaagtgc tgacccagac tccatcccct gtgtctgcag ctgtgggagg caaagtcacc 60

```
atcaattgcc agtccagtca gagtatttat actaactact tatcctggta tcagcagaaa    120
ccaggacagc ctcccaggct cctgatctat tctgcatcca ctctggcatc tggggtccca    180
tcgcggttca aaggcagtgg atctgggaca cagttcactc tcacaatcag cgaagtacag    240
tgtgacgatg ctgccactta ctactgtcaa gcctatttta ctggtgagat ttttcctttc    300
ggcggaggga ccaaggtggt cgtcaaa                                        327
```

<210> SEQ ID NO 62
<211> LENGTH: 342
<212> TYPE: DNA
<213> ORGANISM: Artificial Sequence
<220> FEATURE:
<223> OTHER INFORMATION: derived from rabbit

<400> SEQUENCE: 62

```
caggagcaac tgaaggagtc cggggggaggc ctggtaacgc ctggaggaac cctgacactc    60
acctgcaccg tctctggatt ctccctcgat aactaccaca tgggctgggt ccgccaggct   120
ccagggaagg ggctcaatta catcggattc attactcgtg gtggtaccac atactacgcg   180
agctgggcga agggccgatt caccatctcc aaaacctcga ccacggtgga tctgatgatc   240
accagtccga caaccgggga cacggccacc tatttctgtg ccagaggaag tggcgctagc   300
ggcttttact tgtggggccc aggcaccctg gtcaccgtct cg                       342
```

<210> SEQ ID NO 63
<211> LENGTH: 109
<212> TYPE: PRT
<213> ORGANISM: Artificial Sequence
<220> FEATURE:
<223> OTHER INFORMATION: derived from rabbit

<400> SEQUENCE: 63

Ala Gln Val Leu Thr Gln Thr Pro Ser Pro Val Ser Ala Ala Val Gly
1               5                   10                  15

Gly Lys Val Thr Ile Asn Cys Gln Ser Ser Gln Ser Ile Tyr Thr Asn
            20                  25                  30

Tyr Leu Ser Trp Tyr Gln Gln Lys Pro Gly Gln Pro Pro Arg Leu Leu
        35                  40                  45

Ile Tyr Ser Ala Ser Thr Leu Ala Ser Gly Val Pro Ser Arg Phe Lys
    50                  55                  60

Gly Ser Gly Ser Gly Thr Gln Phe Thr Leu Thr Ile Ser Glu Val Gln
65                  70                  75                  80

Cys Asp Asp Ala Ala Thr Tyr Tyr Cys Gln Ala Tyr Phe Thr Gly Glu
                85                  90                  95

Ile Phe Pro Phe Gly Gly Gly Thr Lys Val Val Val Lys
            100                 105

<210> SEQ ID NO 64
<211> LENGTH: 114
<212> TYPE: PRT
<213> ORGANISM: Artificial Sequence
<220> FEATURE:
<223> OTHER INFORMATION: derived from rabbit

<400> SEQUENCE: 64

Gln Glu Gln Leu Lys Glu Ser Gly Gly Gly Leu Val Thr Pro Gly Gly
1               5                   10                  15

Thr Leu Thr Leu Thr Cys Thr Val Ser Gly Phe Ser Leu Asp Asn Tyr
            20                  25                  30

His Met Gly Trp Val Arg Gln Ala Pro Gly Lys Gly Leu Asn Tyr Ile
            35                  40                  45

Gly Phe Ile Thr Arg Gly Thr Thr Tyr Tyr Ala Ser Trp Ala Lys
 50                  55                  60

Gly Arg Phe Thr Ile Ser Lys Thr Ser Thr Thr Val Asp Leu Met Ile
 65                  70                  75                  80

Thr Ser Pro Thr Thr Gly Asp Thr Ala Thr Tyr Phe Cys Ala Arg Gly
                 85                  90                  95

Ser Gly Ala Ser Gly Phe Tyr Leu Trp Gly Pro Gly Thr Leu Val Thr
                100                 105                 110

Val Ser

<210> SEQ ID NO 65
<211> LENGTH: 738
<212> TYPE: PRT
<213> ORGANISM: Homo sapiens

<400> SEQUENCE: 65

Met Ala Met Leu Pro Pro Gly Pro Gln Ser Phe Val His Phe Thr
 1               5                  10                  15

Lys Gln Ser Leu Ala Leu Ile Glu Gln Arg Ile Ala Glu Arg Lys Ser
            20                  25                  30

Lys Glu Pro Lys Glu Lys Lys Asp Asp Asp Glu Glu Ala Pro Lys
            35                  40                  45

Pro Ser Ser Asp Leu Glu Ala Gly Lys Gln Leu Pro Phe Ile Tyr Gly
 50                  55                  60

Asp Ile Pro Pro Gly Met Val Ser Glu Pro Leu Glu Asp Leu Asp Pro
 65                  70                  75                  80

Tyr Tyr Ala Asp Lys Lys Thr Phe Ile Val Leu Asn Lys Gly Lys Thr
                 85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285

```
Ile Met Asn Thr Leu Glu Ser Glu Glu Asp Phe Arg Lys Tyr Phe Tyr
290                 295                 300
Tyr Leu Glu Gly Ser Lys Asp Ala Leu Leu Cys Gly Phe Ser Thr Asp
305                 310                 315                 320
Ser Gly Gln Cys Pro Glu Gly Tyr Thr Cys Val Lys Ile Gly Arg Asn
                325                 330                 335
Pro Asp Tyr Gly Tyr Thr Ser Phe Asp Thr Phe Ser Trp Ala Phe Leu
            340                 345                 350
Ala Leu Phe Arg Leu Met Thr Gln Asp Tyr Trp Glu Asn Leu Tyr Gln
        355                 360                 365
Gln Thr Leu Arg Ala Ala Gly Lys Thr Tyr Met Ile Phe Phe Val Val
370                 375                 380
Val Ile Phe Leu Gly Ser Phe Tyr Leu Ile Asn Leu Ile Leu Ala Val
385                 390                 395                 400
Val Ala Met Ala Tyr Glu Glu Gln Asn Gln Ala Asn Ile Glu Glu Ala
                405                 410                 415
Lys Gln Lys Glu Leu Glu Phe Gln Gln Met Leu Asp Arg Leu Lys Lys
            420                 425                 430
Glu Gln Glu Glu Ala Glu Ala Ile Ala Ala Ala Ala Ala Glu Tyr Thr
        435                 440                 445
Ser Ile Arg Arg Ser Arg Ile Met Gly Leu Ser Glu Ser Ser Ser Glu
450                 455                 460
Thr Ser Lys Leu Ser Ser Lys Ser Ala Lys Glu Arg Arg Asn Arg Arg
465                 470                 475                 480
Lys Lys Lys Asn Gln Lys Lys Leu Ser Ser Gly Glu Glu Lys Gly Asp
                485                 490                 495
Ala Glu Lys Leu Ser Lys Ser Glu Ser Glu Asp Ser Ile Arg Arg Lys
            500                 505                 510
Ser Phe His Leu Gly Val Glu Gly His Arg Arg Ala His Glu Lys Arg
        515                 520                 525
Leu Ser Thr Pro Asn Gln Ser Pro Leu Ser Ile Arg Gly Ser Leu Phe
530                 535                 540
Ser Ala Arg Arg Ser Ser Arg Thr Ser Leu Phe Ser Phe Lys Gly Arg
545                 550                 555                 560
Gly Arg Asp Ile Gly Ser Glu Thr Glu Phe Ala Asp Asp Glu His Ser
                565                 570                 575
Ile Phe Gly Asp Asn Glu Ser Arg Arg Gly Ser Leu Phe Val Pro His
            580                 585                 590
Arg Pro Gln Glu Arg Arg Ser Ser Asn Ile Ser Gln Ala Ser Arg Ser
        595                 600                 605
Pro Pro Met Leu Pro Val Asn Gly Lys Met His Ser Ala Val Asp Cys
610                 615                 620
Asn Gly Val Val Ser Leu Val Asp Gly Arg Ser Ala Leu Met Leu Pro
625                 630                 635                 640
Asn Gly Gln Leu Leu Pro Glu Val Ile Ile Asp Lys Ala Thr Ser Asp
                645                 650                 655
Asp Ser Gly Thr Thr Asn Gln Ile His Lys Lys Arg Arg Cys Ser Ser
            660                 665                 670
Tyr Leu Leu Ser Glu Asp Met Leu Asn Asp Pro Asn Leu Arg Gln Arg
        675                 680                 685
Ala Met Ser Arg Ala Ser Ile Leu Thr Asn Thr Val Glu Glu Leu Glu
690                 695                 700
Glu Ser Arg Gln Lys Cys Pro Pro Trp Trp Tyr Arg Phe Ala His Lys
```

```
                705                 710                 715                 720
Phe Leu Ile Trp Asn Cys Ser Pro Tyr Trp Ile Lys Phe Lys Lys Cys
                    725                 730                 735
Ile Tyr

<210> SEQ ID NO 66
<211> LENGTH: 449
<212> TYPE: PRT
<213> ORGANISM: Homo sapiens

<400> SEQUENCE: 66

Phe Ile Val Met Asp Pro Phe Val Asp Leu Ala Ile Thr Ile Cys Ile
1               5                   10                  15
Val Leu Asn Thr Leu Phe Met Ala Met Glu His His Pro Met Thr Glu
                20                  25                  30
Glu Phe Lys Asn Val Leu Ala Ile Gly Asn Leu Val Phe Thr Gly Ile
                35                  40                  45
Phe Ala Ala Glu Met Val Leu Lys Leu Ile Ala Met Asp Pro Tyr Glu
            50                  55                  60
Tyr Phe Gln Val Gly Trp Asn Ile Phe Asp Ser Leu Ile Val Thr Leu
65              70                  75                  80
Ser Leu Val Glu Leu Phe Leu Ala Asp Val Glu Gly Leu Ser Val Leu
                85                  90                  95
Arg Ser Phe Arg Leu Leu Arg Val Phe Lys Leu Ala Lys Ser Trp Pro
                100                 105                 110
Thr Leu Asn Met Leu Ile Lys Ile Ile Gly Asn Ser Val Gly Ala Leu
                115                 120                 125
Gly Asn Leu Thr Leu Val Leu Ala Ile Ile Val Phe Ile Phe Ala Val
            130                 135                 140
Val Gly Met Gln Leu Phe Gly Lys Ser Tyr Lys Glu Cys Val Cys Lys
145             150                 155                 160
Ile Asn Asp Asp Cys Thr Leu Pro Arg Trp His Met Asn Asp Phe Phe
                165                 170                 175
His Ser Phe Leu Ile Val Phe Arg Val Leu Cys Gly Glu Trp Ile Glu
                180                 185                 190
Thr Met Trp Asp Cys Met Glu Val Ala Gly Gln Ala Met Cys Leu Ile
                195                 200                 205
Val Tyr Met Met Val Met Val Ile Gly Asn Leu Val Val Leu Asn Leu
            210                 215                 220
Phe Leu Ala Leu Leu Ser Ser Phe Ser Ser Asp Asn Leu Thr Ala
225             230                 235                 240
Ile Glu Glu Asp Pro Asp Ala Asn Asn Leu Gln Ile Ala Val Thr Arg
                245                 250                 255
Ile Lys Lys Gly Ile Asn Tyr Val Lys Gln Thr Leu Arg Glu Phe Ile
                260                 265                 270
Leu Lys Ala Phe Ser Lys Lys Pro Lys Ile Ser Arg Glu Ile Arg Gln
            275                 280                 285
Ala Glu Asp Leu Asn Thr Lys Lys Glu Asn Tyr Ile Ser Asn His Thr
            290                 295                 300
Leu Ala Glu Met Ser Lys Gly His Asn Phe Leu Lys Glu Lys Asp Lys
305             310                 315                 320
Ile Ser Gly Phe Gly Ser Ser Val Asp Lys His Leu Met Glu Asp Ser
                325                 330                 335
Asp Gly Gln Ser Phe Ile His Asn Pro Ser Leu Thr Val Thr Val Pro
```

```
            340                 345                 350
Ile Ala Pro Gly Glu Ser Asp Leu Glu Asn Met Asn Ala Glu Glu Leu
            355                 360                 365

Ser Ser Asp Ser Asp Ser Glu Tyr Ser Lys Val Arg Leu Asn Arg Ser
        370                 375                 380

Ser Ser Ser Glu Cys Ser Thr Val Asp Asn Pro Leu Pro Gly Glu Gly
385                 390                 395                 400

Glu Glu Ala Glu Ala Glu Pro Met Asn Ser Asp Glu Pro Glu Ala Cys
                405                 410                 415

Phe Thr Asp Gly Cys Val Arg Arg Phe Ser Cys Cys Gln Val Asn Ile
            420                 425                 430

Glu Ser Gly Lys Gly Lys Ile Trp Trp Asn Ile Arg Lys Thr Cys Tyr
            435                 440                 445

Lys

<210> SEQ ID NO 67
<211> LENGTH: 322
<212> TYPE: PRT
<213> ORGANISM: Homo sapiens

<400> SEQUENCE: 67

Ile Val Glu His Ser Trp Phe Glu Ser Phe Ile Val Leu Met Ile Leu
1               5                  10                  15

Leu Ser Ser Gly Ala Leu Ala Phe Glu Asp Ile Tyr Ile Glu Arg Lys
                20                  25                  30

Lys Thr Ile Lys Ile Ile Leu Glu Tyr Ala Asp Lys Ile Phe Thr Tyr
            35                  40                  45

Ile Phe Ile Leu Glu Met Leu Leu Lys Trp Ile Ala Tyr Gly Tyr Lys
        50                  55                  60

Thr Tyr Phe Thr Asn Ala Trp Cys Trp Leu Asp Phe Leu Ile Val Asp
65                  70                  75                  80

Val Ser Leu Val Thr Leu Val Ala Asn Thr Leu Gly Tyr Ser Asp Leu
                85                  90                  95

Gly Pro Ile Ser Leu Arg Thr Leu Arg Ala Leu Arg Pro Leu Arg Ala
            100                 105                 110

Leu Ser Arg Phe Glu Gly Met Arg Val Val Val Asn Ala Leu Ile Gly
        115                 120                 125

Ala Ile Pro Ser Ile Met Asn Val Leu Leu Val Cys Leu Ile Phe Trp
    130                 135                 140

Leu Ile Phe Ser Ile Met Gly Val Asn Leu Phe Ala Gly Lys Phe Tyr
145                 150                 155                 160

Glu Cys Ile Asn Thr Thr Asp Gly Ser Arg Phe Pro Ala Ser Gln Val
                165                 170                 175

Pro Asn Arg Ser Glu Cys Phe Ala Leu Met Asn Val Ser Gln Asn Val
            180                 185                 190

Arg Trp Lys Asn Leu Lys Val Asn Phe Asp Asn Val Gly Leu Gly Tyr
        195                 200                 205

Leu Ser Leu Leu Gln Val Ala Thr Phe Lys Gly Trp Thr Ile Ile Met
    210                 215                 220

Tyr Ala Ala Val Asp Ser Val Asn Val Asp Lys Gln Pro Lys Tyr Glu
225                 230                 235                 240

Tyr Ser Leu Tyr Met Tyr Ile Tyr Phe Val Phe Ile Ile Phe Gly
                245                 250                 255

Ser Phe Phe Thr Leu Asn Leu Phe Ile Gly Val Ile Ile Asp Asn Phe
```

```
                260                 265                 270
Asn Gln Gln Lys Lys Lys Leu Gly Gly Gln Asp Ile Phe Met Thr Glu
            275                 280                 285

Glu Gln Lys Lys Tyr Tyr Asn Ala Met Lys Lys Leu Gly Ser Lys Lys
        290                 295                 300

Pro Gln Lys Pro Ile Pro Arg Pro Gly Asn Lys Ile Gln Gly Cys Ile
305                 310                 315                 320

Phe Asp

<210> SEQ ID NO 68
<211> LENGTH: 478
<212> TYPE: PRT
<213> ORGANISM: Homo sapiens

<400> SEQUENCE: 68

Leu Val Thr Asn Gln Ala Phe Asp Ile Ser Ile Met Val Leu Ile Cys
1               5                   10                  15

Leu Asn Met Val Thr Met Met Val Glu Lys Glu Gly Gln Ser Gln His
            20                  25                  30

Met Thr Glu Val Leu Tyr Trp Ile Asn Val Val Phe Ile Ile Leu Phe
        35                  40                  45

Thr Gly Glu Cys Val Leu Lys Leu Ile Ser Leu Arg His Tyr Tyr Phe
    50                  55                  60

Thr Val Gly Trp Asn Ile Phe Asp Phe Val Val Val Ile Ile Ser Ile
65                  70                  75                  80

Val Gly Met Phe Leu Ala Asp Leu Ile Glu Thr Tyr Phe Val Ser Pro
                85                  90                  95

Thr Leu Phe Arg Val Ile Arg Leu Ala Arg Ile Gly Arg Ile Leu Arg
            100                 105                 110

Leu Val Lys Gly Ala Lys Gly Ile Arg Thr Leu Leu Phe Ala Leu Met
        115                 120                 125

Met Ser Leu Pro Ala Leu Phe Asn Ile Gly Leu Leu Leu Phe Leu Val
    130                 135                 140

Met Phe Ile Tyr Ala Ile Phe Gly Met Ser Asn Phe Ala Tyr Val Lys
145                 150                 155                 160

Lys Glu Asp Gly Ile Asn Asp Met Phe Asn Phe Glu Thr Phe Gly Asn
                165                 170                 175

Ser Met Ile Cys Leu Phe Gln Ile Thr Thr Ser Ala Gly Trp Asp Gly
            180                 185                 190

Leu Leu Ala Pro Ile Leu Asn Ser Lys Pro Pro Asp Cys Asp Pro Lys
        195                 200                 205

Lys Val His Pro Gly Ser Ser Val Glu Gly Asp Cys Gly Asn Pro Ser
    210                 215                 220

Val Gly Ile Phe Tyr Phe Val Ser Tyr Ile Ile Ile Ser Phe Leu Val
225                 230                 235                 240

Val Val Asn Met Tyr Ile Ala Val Ile Leu Glu Asn Phe Ser Val Ala
                245                 250                 255

Thr Glu Glu Ser Thr Glu Pro Leu Ser Glu Asp Asp Phe Glu Met Phe
            260                 265                 270

Tyr Glu Val Trp Glu Lys Phe Asp Pro Asp Ala Thr Gln Phe Ile Glu
        275                 280                 285

Phe Ser Lys Leu Ser Asp Phe Ala Ala Ala Leu Asp Pro Pro Leu Leu
    290                 295                 300

Ile Ala Lys Pro Asn Lys Val Gln Leu Ile Ala Met Asp Leu Pro Met
```

```
            305                 310                 315                 320

Val Ser Gly Asp Arg Ile His Cys Leu Asp Ile Leu Phe Ala Phe Thr
                325                 330                 335

Lys Arg Val Leu Gly Glu Ser Gly Glu Met Asp Ser Leu Arg Ser Gln
                340                 345                 350

Met Glu Glu Arg Phe Met Ser Ala Asn Pro Ser Lys Val Ser Tyr Glu
                355                 360                 365

Pro Ile Thr Thr Thr Leu Lys Arg Lys Gln Glu Asp Val Ser Ala Thr
                370                 375                 380

Val Ile Gln Arg Ala Tyr Arg Arg Tyr Arg Leu Arg Gln Asn Val Lys
385                 390                 395                 400

Asn Ile Ser Ser Ile Tyr Ile Lys Asp Gly Asp Arg Asp Asp Asp Leu
                405                 410                 415

Leu Asn Lys Lys Asp Met Ala Phe Asp Asn Val Asn Glu Asn Ser Ser
                420                 425                 430

Pro Glu Lys Thr Asp Ala Thr Ser Ser Thr Thr Ser Pro Pro Ser Tyr
                435                 440                 445

Asp Ser Val Thr Lys Pro Asp Lys Glu Lys Tyr Glu Gln Asp Arg Thr
                450                 455                 460

Glu Lys Glu Asp Lys Gly Lys Asp Ser Lys Glu Ser Lys Lys
465                 470                 475

<210> SEQ ID NO 69
<211> LENGTH: 1987
<212> TYPE: PRT
<213> ORGANISM: Homo sapiens

<400> SEQUENCE: 69

Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
                20                  25                  30

Lys Glu Pro Lys Glu Glu Lys Lys Asp Asp Asp Glu Glu Ala Pro Lys
                35                  40                  45

Pro Ser Ser Asp Leu Glu Ala Gly Lys Gln Leu Pro Phe Ile Tyr Gly
                50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
                100                 105                 110

Ser Pro Leu Arg Arg Ile Ser Ile Lys Ile Leu Val His Ser Leu Phe
                115                 120                 125

Ser Met Leu Ile Met Cys Thr Ile Leu Thr Asn Cys Ile Phe Met Thr
                130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
                180                 185                 190

Phe Val Val Ile Val Phe Ala Tyr Leu Thr Glu Phe Val Asn Leu Gly
                195                 200                 205
```

```
Asn Val Ser Ala Leu Arg Thr Phe Arg Val Leu Arg Ala Leu Lys Thr
210                 215                 220
Ile Ser Val Ile Pro Gly Leu Lys Thr Ile Val Gly Ala Leu Ile Gln
225                 230                 235                 240
Ser Val Lys Lys Leu Ser Asp Val Met Ile Leu Thr Val Phe Cys Leu
            245                 250                 255
Ser Val Phe Ala Leu Ile Gly Leu Gln Leu Phe Met Gly Asn Leu Lys
        260                 265                 270
His Lys Cys Phe Arg Asn Ser Leu Glu Asn Asn Glu Thr Leu Glu Ser
            275                 280                 285
Ile Met Asn Thr Leu Glu Ser Glu Glu Asp Phe Arg Lys Tyr Phe Tyr
290                 295                 300
Tyr Leu Glu Gly Ser Lys Asp Ala Leu Leu Cys Gly Phe Ser Thr Asp
305                 310                 315                 320
Ser Gly Gln Cys Pro Glu Gly Tyr Thr Cys Val Lys Ile Gly Arg Asn
                325                 330                 335
Pro Asp Tyr Gly Tyr Thr Ser Phe Asp Thr Phe Ser Trp Ala Phe Leu
            340                 345                 350
Ala Leu Phe Arg Leu Met Thr Gln Asp Tyr Trp Glu Asn Leu Tyr Gln
        355                 360                 365
Gln Thr Leu Arg Ala Ala Gly Lys Thr Tyr Met Ile Phe Phe Val Val
370                 375                 380
Val Ile Phe Leu Gly Ser Phe Tyr Leu Ile Asn Leu Ile Leu Ala Val
385                 390                 395                 400
Val Ala Met Ala Tyr Glu Glu Gln Asn Gln Ala Asn Ile Glu Glu Ala
                405                 410                 415
Lys Gln Lys Glu Leu Glu Phe Gln Gln Met Leu Asp Arg Leu Lys Lys
            420                 425                 430
Glu Gln Glu Glu Ala Glu Ala Ile Ala Ala Ala Ala Ala Glu Tyr Thr
        435                 440                 445
Ser Ile Arg Arg Ser Arg Ile Met Gly Leu Ser Glu Ser Ser Ser Glu
450                 455                 460
Thr Ser Lys Leu Ser Ser Lys Ser Ala Lys Glu Arg Arg Asn Arg Arg
465                 470                 475                 480
Lys Lys Lys Asn Gln Lys Lys Leu Ser Ser Gly Glu Glu Lys Gly Asp
                485                 490                 495
Ala Glu Lys Leu Ser Lys Ser Glu Ser Glu Asp Ser Ile Arg Arg Lys
            500                 505                 510
Ser Phe His Leu Gly Val Glu Gly His Arg Arg Ala His Glu Lys Arg
        515                 520                 525
Leu Ser Thr Pro Asn Gln Ser Pro Leu Ser Ile Arg Gly Ser Leu Phe
530                 535                 540
Ser Ala Arg Arg Ser Ser Arg Thr Ser Leu Phe Ser Phe Lys Gly Arg
545                 550                 555                 560
Gly Arg Asp Ile Gly Ser Glu Thr Glu Phe Ala Asp Asp Glu His Ser
                565                 570                 575
Ile Phe Gly Asp Asn Glu Ser Arg Arg Gly Ser Leu Phe Val Pro His
            580                 585                 590
Arg Pro Gln Glu Arg Arg Ser Ser Asn Ile Ser Gln Ala Ser Arg Ser
        595                 600                 605
Pro Pro Met Leu Pro Val Asn Gly Lys Met His Ser Ala Val Asp Cys
610                 615                 620
Asn Gly Val Val Ser Leu Val Asp Gly Arg Ser Ala Leu Met Leu Pro
```

-continued

```
            625                 630                 635                 640
Asn Gly Gln Leu Leu Pro Glu Val Ile Ile Asp Lys Ala Thr Ser Asp
                    645                 650                 655

Asp Ser Gly Thr Thr Asn Gln Ile His Lys Lys Arg Arg Cys Ser Ser
            660                 665                 670

Tyr Leu Leu Ser Glu Asp Met Leu Asn Asp Pro Asn Leu Arg Gln Arg
            675                 680                 685

Ala Met Ser Arg Ala Ser Ile Leu Thr Asn Thr Val Glu Glu Leu Glu
            690                 695                 700

Glu Ser Arg Gln Lys Cys Pro Pro Trp Trp Tyr Arg Phe Ala His Lys
705                 710                 715                 720

Phe Leu Ile Trp Asn Cys Ser Pro Tyr Trp Ile Lys Phe Lys Lys Cys
                    725                 730                 735

Ile Tyr Phe Ile Val Met Asp Pro Phe Val Asp Leu Ala Ile Thr Ile
                    740                 745                 750

Cys Ile Val Leu Asn Thr Leu Phe Met Ala Met Glu His His Pro Met
                    755                 760                 765

Thr Glu Glu Phe Lys Asn Val Leu Ala Ile Gly Asn Leu Val Phe Thr
            770                 775                 780

Gly Ile Phe Ala Ala Glu Met Val Leu Lys Leu Ile Ala Met Asp Pro
785                 790                 795                 800

Tyr Glu Tyr Phe Gln Val Gly Trp Asn Ile Phe Asp Ser Leu Ile Val
                    805                 810                 815

Thr Leu Ser Leu Val Glu Leu Phe Leu Ala Asp Val Glu Gly Leu Ser
                    820                 825                 830

Val Leu Arg Ser Phe Arg Leu Leu Arg Val Phe Lys Leu Ala Lys Ser
            835                 840                 845

Trp Pro Thr Leu Asn Met Leu Ile Lys Ile Ile Gly Asn Ser Val Gly
            850                 855                 860

Ala Leu Gly Asn Leu Thr Leu Val Leu Ala Ile Ile Val Phe Ile Phe
865                 870                 875                 880

Ala Val Val Gly Met Gln Leu Phe Gly Lys Ser Tyr Lys Glu Cys Val
                    885                 890                 895

Cys Lys Ile Asn Asp Asp Cys Thr Leu Pro Arg Trp His Met Asn Asp
                    900                 905                 910

Phe Phe His Ser Phe Leu Ile Val Phe Arg Val Leu Cys Gly Glu Trp
            915                 920                 925

Ile Glu Thr Met Trp Asp Cys Met Glu Val Ala Gly Gln Ala Met Cys
            930                 935                 940

Leu Ile Val Tyr Met Met Val Met Val Ile Gly Asn Leu Val Val Leu
945                 950                 955                 960

Asn Leu Phe Leu Ala Leu Leu Leu Ser Ser Phe Ser Ser Asp Asn Leu
                    965                 970                 975

Thr Ala Ile Glu Glu Asp Pro Asp Ala Asn Asn Leu Gln Ile Ala Val
            980                 985                 990

Thr Arg Ile Lys Lys Gly Ile Asn Tyr Val Lys Gln Thr Leu Arg Glu
            995                1000                1005

Phe Ile Leu Lys Ala Phe Ser Lys Lys Pro Lys Ile Ser Arg Glu
           1010                1015                1020

Ile Arg Gln Ala Glu Asp Leu Asn Thr Lys Lys Glu Asn Tyr Ile
           1025                1030                1035

Ser Asn His Thr Leu Ala Glu Met Ser Lys Gly His Asn Phe Leu
           1040                1045                1050
```

-continued

| | | | | | | | | | |
|---|---|---|---|---|---|---|---|---|---|
|Lys|Glu|Lys|Asp|Lys|Ile|Ser|Gly|Phe|Gly|Ser|Ser|Val|Asp|Lys|
| |1055| | | |1060| | | |1065| | | | | |

Lys Glu Lys Asp Lys Ile Ser Gly Phe Gly Ser Ser Val Asp Lys
    1055                1060                1065

His Leu Met Glu Asp Ser Asp Gly Gln Ser Phe Ile His Asn Pro
    1070                1075                1080

Ser Leu Thr Val Thr Val Pro Ile Ala Pro Gly Glu Ser Asp Leu
    1085                1090                1095

Glu Asn Met Asn Ala Glu Glu Leu Ser Ser Asp Ser Asp Ser Glu
    1100                1105                1110

Tyr Ser Lys Val Arg Leu Asn Arg Ser Ser Ser Glu Cys Ser
    1115                1120                1125

Thr Val Asp Asn Pro Leu Pro Gly Glu Gly Glu Glu Ala Glu Ala
    1130                1135                1140

Glu Pro Met Asn Ser Asp Glu Pro Glu Ala Cys Phe Thr Asp Gly
    1145                1150                1155

Cys Val Arg Arg Phe Ser Cys Cys Gln Val Asn Ile Glu Ser Gly
    1160                1165                1170

Lys Gly Lys Ile Trp Trp Asn Ile Arg Lys Thr Cys Tyr Lys Ile
    1175                1180                1185

Val Glu His Ser Trp Phe Glu Ser Phe Ile Val Leu Met Ile Leu
    1190                1195                1200

Leu Ser Ser Gly Ala Leu Ala Phe Glu Asp Ile Tyr Ile Glu Arg
    1205                1210                1215

Lys Lys Thr Ile Lys Ile Ile Leu Glu Tyr Ala Asp Lys Ile Phe
    1220                1225                1230

Thr Tyr Ile Phe Ile Leu Glu Met Leu Leu Lys Trp Ile Ala Tyr
    1235                1240                1245

Gly Tyr Lys Thr Tyr Phe Thr Asn Ala Trp Cys Trp Leu Asp Phe
    1250                1255                1260

Leu Ile Val Asp Val Ser Leu Val Thr Leu Val Ala Asn Thr Leu
    1265                1270                1275

Gly Tyr Ser Asp Leu Gly Pro Ile Ser Leu Arg Thr Leu Arg Ala
    1280                1285                1290

Leu Arg Pro Leu Arg Ala Leu Ser Arg Phe Glu Gly Met Arg Val
    1295                1300                1305

Val Val Asn Ala Leu Ile Gly Ala Ile Pro Ser Ile Met Asn Val
    1310                1315                1320

Leu Leu Val Cys Leu Ile Phe Trp Leu Ile Phe Ser Ile Met Gly
    1325                1330                1335

Val Asn Leu Phe Ala Gly Lys Phe Tyr Glu Cys Ile Asn Thr Thr
    1340                1345                1350

Asp Gly Ser Arg Phe Pro Ala Ser Gln Val Pro Asn Arg Ser Glu
    1355                1360                1365

Cys Phe Ala Leu Met Asn Val Ser Gln Asn Val Arg Trp Lys Asn
    1370                1375                1380

Leu Lys Val Asn Phe Asp Asn Val Gly Leu Gly Tyr Leu Ser Leu
    1385                1390                1395

Leu Gln Val Ala Thr Phe Lys Gly Trp Thr Ile Ile Met Tyr Ala
    1400                1405                1410

Ala Val Asp Ser Val Asn Val Asp Lys Gln Pro Lys Tyr Glu Tyr
    1415                1420                1425

Ser Leu Tyr Met Tyr Ile Tyr Phe Val Val Phe Ile Ile Phe Gly
    1430                1435                1440

```
Ser Phe Phe Thr Leu Asn Leu Phe Ile Gly Val Ile Ile Asp Asn
1445                1450                1455

Phe Asn Gln Gln Lys Lys Leu Gly Gly Gln Asp Ile Phe Met
1460                1465                1470

Thr Glu Glu Gln Lys Lys Tyr Tyr Asn Ala Met Lys Lys Leu Gly
1475                1480                1485

Ser Lys Lys Pro Gln Lys Pro Ile Pro Arg Pro Gly Asn Lys Ile
1490                1495                1500

Gln Gly Cys Ile Phe Asp Leu Val Thr Asn Gln Ala Phe Asp Ile
1505                1510                1515

Ser Ile Met Val Leu Ile Cys Leu Asn Met Val Thr Met Met Val
1520                1525                1530

Glu Lys Glu Gly Gln Ser Gln His Met Thr Glu Val Leu Tyr Trp
1535                1540                1545

Ile Asn Val Val Phe Ile Ile Leu Phe Thr Gly Glu Cys Val Leu
1550                1555                1560

Lys Leu Ile Ser Leu Arg His Tyr Tyr Phe Thr Val Gly Trp Asn
1565                1570                1575

Ile Phe Asp Phe Val Val Val Ile Ile Ser Ile Val Gly Met Phe
1580                1585                1590

Leu Ala Asp Leu Ile Glu Thr Tyr Phe Val Ser Pro Thr Leu Phe
1595                1600                1605

Arg Val Ile Arg Leu Ala Arg Ile Gly Arg Ile Leu Arg Leu Val
1610                1615                1620

Lys Gly Ala Lys Gly Ile Arg Thr Leu Leu Phe Ala Leu Met Met
1625                1630                1635

Ser Leu Pro Ala Leu Phe Asn Ile Gly Leu Leu Leu Phe Leu Val
1640                1645                1650

Met Phe Ile Tyr Ala Ile Phe Gly Met Ser Asn Phe Ala Tyr Val
1655                1660                1665

Lys Lys Glu Asp Gly Ile Asn Asp Met Phe Asn Phe Glu Thr Phe
1670                1675                1680

Gly Asn Ser Met Ile Cys Leu Phe Gln Ile Thr Thr Ser Ala Gly
1685                1690                1695

Trp Asp Gly Leu Leu Ala Pro Ile Leu Asn Ser Lys Pro Pro Asp
1700                1705                1710

Cys Asp Pro Lys Lys Val His Pro Gly Ser Ser Val Glu Gly Asp
1715                1720                1725

Cys Gly Asn Pro Ser Val Gly Ile Phe Tyr Phe Val Ser Tyr Ile
1730                1735                1740

Ile Ile Ser Phe Leu Val Val Val Asn Met Tyr Ile Ala Val Ile
1745                1750                1755

Leu Glu Asn Phe Ser Val Ala Thr Glu Glu Ser Thr Glu Pro Leu
1760                1765                1770

Ser Glu Asp Asp Phe Glu Met Phe Tyr Glu Val Trp Glu Lys Phe
1775                1780                1785

Asp Pro Asp Ala Thr Gln Phe Ile Glu Phe Ser Lys Leu Ser Asp
1790                1795                1800

Phe Ala Ala Ala Leu Asp Pro Pro Leu Leu Ile Ala Lys Pro Asn
1805                1810                1815

Lys Val Gln Leu Ile Ala Met Asp Leu Pro Met Val Ser Gly Asp
1820                1825                1830

Arg Ile His Cys Leu Asp Ile Leu Phe Ala Phe Thr Lys Arg Val
```

```
                    1835                1840                1845

Leu Gly Glu Ser Gly Glu Met Asp Ser Leu Arg Ser Gln Met Glu
            1850                1855                1860

Glu Arg Phe Met Ser Ala Asn Pro Ser Lys Val Ser Tyr Glu Pro
        1865                1870                1875

Ile Thr Thr Thr Leu Lys Arg Lys Gln Glu Asp Val Ser Ala Thr
    1880                1885                1890

Val Ile Gln Arg Ala Tyr Arg Arg Tyr Arg Leu Arg Gln Asn Val
1895                1900                1905

Lys Asn Ile Ser Ser Ile Tyr Ile Lys Asp Gly Asp Arg Asp Asp
    1910                1915                1920

Asp Leu Leu Asn Lys Lys Asp Met Ala Phe Asp Asn Val Asn Glu
    1925                1930                1935

Asn Ser Ser Pro Glu Lys Thr Asp Ala Thr Ser Ser Thr Thr Ser
    1940                1945                1950

Pro Pro Ser Tyr Asp Ser Val Thr Lys Pro Asp Lys Glu Lys Tyr
    1955                1960                1965

Glu Gln Asp Arg Thr Glu Lys Glu Asp Lys Gly Lys Asp Ser Lys
    1970                1975                1980

Glu Ser Lys Lys
    1985

<210> SEQ ID NO 70
<211> LENGTH: 22
<212> TYPE: PRT
<213> ORGANISM: Homo sapiens

<400> SEQUENCE: 70

Glu Pro Lys Ser Cys Asp Lys Thr His Thr Cys Pro Pro Cys Pro Ala
1               5                   10                  15

Pro Glu Leu Leu Gly Gly
            20

<210> SEQ ID NO 71
<211> LENGTH: 6
<212> TYPE: PRT
<213> ORGANISM: Artificial Sequence
<220> FEATURE:
<223> OTHER INFORMATION: derived from homo sapiens Nav1.7

<400> SEQUENCE: 71

Thr Met Asn Asn Pro Pro
1               5

<210> SEQ ID NO 72
<211> LENGTH: 28
<212> TYPE: PRT
<213> ORGANISM: Artificial Sequence
<220> FEATURE:
<223> OTHER INFORMATION: derived from homo sapiens Nav1.7

<400> SEQUENCE: 72

Cys Phe Arg Asn Ser Leu Glu Asn Asn Glu Thr Leu Glu Ser Ile Met
1               5                   10                  15

Asn Thr Leu Glu Ser Glu Glu Asp Phe Arg Lys Tyr
            20                  25

<210> SEQ ID NO 73
<211> LENGTH: 6
<212> TYPE: PRT
```

```
<213> ORGANISM: Artificial Sequence
<220> FEATURE:
<223> OTHER INFORMATION: derived from homo sapiens Nav1.7

<400> SEQUENCE: 73

Glu Gly Ser Lys Asp Ala
1               5

<210> SEQ ID NO 74
<211> LENGTH: 8
<212> TYPE: PRT
<213> ORGANISM: Artificial Sequence
<220> FEATURE:
<223> OTHER INFORMATION: derived from homo sapiens Nav1.7

<400> SEQUENCE: 74

Gly Phe Ser Thr Asp Ser Gly Gln
1               5

<210> SEQ ID NO 75
<211> LENGTH: 9
<212> TYPE: PRT
<213> ORGANISM: Artificial Sequence
<220> FEATURE:
<223> OTHER INFORMATION: derived from homo sapiens Nav1.7

<400> SEQUENCE: 75

His Pro Met Thr Glu Glu Phe Lys Asn
1               5

<210> SEQ ID NO 76
<211> LENGTH: 7
<212> TYPE: PRT
<213> ORGANISM: Artificial Sequence
<220> FEATURE:
<223> OTHER INFORMATION: derived from homo sapiens Nav1.7

<400> SEQUENCE: 76

Asn Asp Asp Cys Thr Leu Pro
1               5

<210> SEQ ID NO 77
<211> LENGTH: 9
<212> TYPE: PRT
<213> ORGANISM: Artificial Sequence
<220> FEATURE:
<223> OTHER INFORMATION: derived from homo sapiens Nav1.7

<400> SEQUENCE: 77

Ile Glu Arg Lys Lys Thr Ile Lys Ile
1               5

<210> SEQ ID NO 78
<211> LENGTH: 16
<212> TYPE: PRT
<213> ORGANISM: Artificial Sequence
<220> FEATURE:
<223> OTHER INFORMATION: derived from homo sapiens Nav1.7

<400> SEQUENCE: 78

Cys Ile Asn Thr Thr Asp Gly Ser Arg Phe Pro Ala Ser Gln Val Pro
1               5                   10                  15

<210> SEQ ID NO 79
<211> LENGTH: 9
<212> TYPE: PRT
<213> ORGANISM: Artificial Sequence
```

```
<220> FEATURE:
<223> OTHER INFORMATION: derived from homo sapiens Nav1.7

<400> SEQUENCE: 79

Asn Arg Ser Glu Cys Phe Ala Leu Met
1               5

<210> SEQ ID NO 80
<211> LENGTH: 7
<212> TYPE: PRT
<213> ORGANISM: Artificial Sequence
<220> FEATURE:
<223> OTHER INFORMATION: derived from homo sapiens Nav1.7

<400> SEQUENCE: 80

Asn Val Ser Gln Asn Val Arg
1               5

<210> SEQ ID NO 81
<211> LENGTH: 8
<212> TYPE: PRT
<213> ORGANISM: Artificial Sequence
<220> FEATURE:
<223> OTHER INFORMATION: derived from homo sapiens Nav1.7

<400> SEQUENCE: 81

Ser Val Asn Val Asp Lys Gln Pro
1               5

<210> SEQ ID NO 82
<211> LENGTH: 11
<212> TYPE: PRT
<213> ORGANISM: Artificial Sequence
<220> FEATURE:
<223> OTHER INFORMATION: derived from homo sapiens Nav1.7

<400> SEQUENCE: 82

Glu Lys Glu Gly Gln Ser Gln His Met Thr Glu
1               5                   10

<210> SEQ ID NO 83
<211> LENGTH: 8
<212> TYPE: PRT
<213> ORGANISM: Artificial Sequence
<220> FEATURE:
<223> OTHER INFORMATION: derived from homo sapiens Nav1.7

<400> SEQUENCE: 83

Lys Lys Glu Asp Gly Ile Asn Asp
1               5

<210> SEQ ID NO 84
<211> LENGTH: 8
<212> TYPE: PRT
<213> ORGANISM: Artificial Sequence
<220> FEATURE:
<223> OTHER INFORMATION: derived from homo sapiens Nav1.7

<400> SEQUENCE: 84

Cys Asp Pro Lys Lys Val His Pro
1               5

<210> SEQ ID NO 85
<211> LENGTH: 7
<212> TYPE: PRT
<213> ORGANISM: Artificial Sequence
<220> FEATURE:
```

```
<223> OTHER INFORMATION: derived from homo sapiens Nav.17

<400> SEQUENCE: 85

Cys Thr Met Asn Asn Pro Pro
1               5

<210> SEQ ID NO 86
<211> LENGTH: 9
<212> TYPE: PRT
<213> ORGANISM: Artificial Sequence
<220> FEATURE:
<223> OTHER INFORMATION: derived from homo sapiens Nav1.7

<400> SEQUENCE: 86

Cys Phe Arg Asn Ser Leu Glu Asn Asn
1               5

<210> SEQ ID NO 87
<211> LENGTH: 19
<212> TYPE: PRT
<213> ORGANISM: Artificial Sequence
<220> FEATURE:
<223> OTHER INFORMATION: derived from homo sapiens Nav1.7

<400> SEQUENCE: 87

Cys Thr Leu Glu Ser Ile Met Asn Thr Leu Glu Ser Glu Asp Phe
1               5                   10                  15

Arg Lys Tyr

<210> SEQ ID NO 88
<211> LENGTH: 7
<212> TYPE: PRT
<213> ORGANISM: Artificial Sequence
<220> FEATURE:
<223> OTHER INFORMATION: derived from homo sapiens Nav1.7

<400> SEQUENCE: 88

Cys Glu Gly Ser Lys Asp Ala
1               5

<210> SEQ ID NO 89
<211> LENGTH: 8
<212> TYPE: PRT
<213> ORGANISM: Artificial Sequence
<220> FEATURE:
<223> OTHER INFORMATION: derived from homo sapiens Nav1.7

<400> SEQUENCE: 89

Cys Phe Ser Thr Asp Ser Gly Gln
1               5

<210> SEQ ID NO 90
<211> LENGTH: 9
<212> TYPE: PRT
<213> ORGANISM: Artificial Sequence
<220> FEATURE:
<223> OTHER INFORMATION: peptide derived from homo sapiens Nav1.7

<400> SEQUENCE: 90

Cys Pro Met Thr Glu Glu Phe Lys Asn
1               5

<210> SEQ ID NO 91
<211> LENGTH: 11
<212> TYPE: PRT
<213> ORGANISM: Artificial Sequence
```

```
<220> FEATURE:
<223> OTHER INFORMATION: derived from homo sapiens Nav1.7

<400> SEQUENCE: 91

Asp Asp Cys Thr Leu Pro Arg Trp His Met Asn
1               5                   10

<210> SEQ ID NO 92
<211> LENGTH: 10
<212> TYPE: PRT
<213> ORGANISM: Artificial Sequence
<220> FEATURE:
<223> OTHER INFORMATION: derived from homo sapiens Nav1.7

<400> SEQUENCE: 92

Cys Ile Glu Arg Lys Lys Thr Ile Lys Ile
1               5                   10

<210> SEQ ID NO 93
<211> LENGTH: 8
<212> TYPE: PRT
<213> ORGANISM: Artificial Sequence
<220> FEATURE:
<223> OTHER INFORMATION: derived from homo sapiens Nav1.7

<400> SEQUENCE: 93

Cys Asn Val Ser Gln Asn Val Arg
1               5

<210> SEQ ID NO 94
<211> LENGTH: 8
<212> TYPE: PRT
<213> ORGANISM: Artificial Sequence
<220> FEATURE:
<223> OTHER INFORMATION: derived from homo sapiens Nav1.7

<400> SEQUENCE: 94

Val Asn Val Asp Lys Gln Pro Cys
1               5

<210> SEQ ID NO 95
<211> LENGTH: 12
<212> TYPE: PRT
<213> ORGANISM: Artificial Sequence
<220> FEATURE:
<223> OTHER INFORMATION: derived from homo sapiens Nav1.7

<400> SEQUENCE: 95

Cys Glu Lys Glu Gly Gln Ser Gln His Met Thr Glu
1               5                   10

<210> SEQ ID NO 96
<211> LENGTH: 9
<212> TYPE: PRT
<213> ORGANISM: Artificial Sequence
<220> FEATURE:
<223> OTHER INFORMATION: derived from homo sapiens Nav1.7

<400> SEQUENCE: 96

Lys Lys Glu Asp Gly Ile Asn Asp Cys
1               5

<210> SEQ ID NO 97
<211> LENGTH: 9
<212> TYPE: PRT
<213> ORGANISM: Artificial Sequence
<220> FEATURE:
```

<223> OTHER INFORMATION: derived from homo sapiens Nav1.7

<400> SEQUENCE: 97

Cys Thr Met Asn Asn Pro Pro Asp Trp
1               5

<210> SEQ ID NO 98
<211> LENGTH: 12
<212> TYPE: PRT
<213> ORGANISM: Artificial Sequence
<220> FEATURE:
<223> OTHER INFORMATION: derived from homo sapiens Nav1.7

<400> SEQUENCE: 98

Cys Glu His His Pro Met Thr Glu Glu Phe Lys Asn
1               5                   10

<210> SEQ ID NO 99
<211> LENGTH: 6
<212> TYPE: PRT
<213> ORGANISM: Artificial Sequence
<220> FEATURE:
<223> OTHER INFORMATION: derived from homo sapiens Nav1.7

<400> SEQUENCE: 99

Cys Gly Gln Ser Gln His
1               5

<210> SEQ ID NO 100
<211> LENGTH: 11
<212> TYPE: PRT
<213> ORGANISM: Artificial Sequence
<220> FEATURE:
<223> OTHER INFORMATION: derived from homo sapiens Nav1.7

<400> SEQUENCE: 100

Cys Phe Arg Asn Ser Leu Glu Asn Asn Glu Thr
1               5                   10

<210> SEQ ID NO 101
<211> LENGTH: 6
<212> TYPE: PRT
<213> ORGANISM: Artificial Sequence
<220> FEATURE:
<223> OTHER INFORMATION: derived from homo sapiens Nav1.7

<400> SEQUENCE: 101

Cys Lys Ile Asn Asp Asp
1               5

<210> SEQ ID NO 102
<211> LENGTH: 11
<212> TYPE: PRT
<213> ORGANISM: Artificial Sequence
<220> FEATURE:
<223> OTHER INFORMATION: derived from homo sapiens Nav1.7

<400> SEQUENCE: 102

Cys Thr Leu Pro Arg Trp His Met Asn Asp Asp
1               5                   10

<210> SEQ ID NO 103
<211> LENGTH: 20
<212> TYPE: PRT
<213> ORGANISM: Artificial Sequence
<220> FEATURE:
<223> OTHER INFORMATION: derived from homo sapiens Nav1.7

```
<400> SEQUENCE: 103

Cys Ile Asn Thr Thr Asp Gly Ser Arg Phe Pro Ala Ser Gln Val Pro
1               5                   10                  15

Asn Arg Ser Glu
            20

<210> SEQ ID NO 104
<211> LENGTH: 23
<212> TYPE: PRT
<213> ORGANISM: Artificial Sequence
<220> FEATURE:
<223> OTHER INFORMATION: derived from homo sapiens Kv3.2

<400> SEQUENCE: 104

Cys Lys Asn Lys Thr Glu Pro Val Ile Asn Gly Thr Ser Pro Val Leu
1               5                   10                  15

Gln Tyr Glu Ile Glu Thr Asp
            20

<210> SEQ ID NO 105
<211> LENGTH: 17
<212> TYPE: PRT
<213> ORGANISM: Artificial Sequence
<220> FEATURE:
<223> OTHER INFORMATION: derived from homo sapiens Kv3.2

<400> SEQUENCE: 105

Cys Arg Val Gly Ala Gln Pro Asn Asp Pro Ser Ala Ser Glu His Thr
1               5                   10                  15

Gln

<210> SEQ ID NO 106
<211> LENGTH: 7
<212> TYPE: PRT
<213> ORGANISM: Artificial Sequence
<220> FEATURE:
<223> OTHER INFORMATION: derived from homo sapiens Nav1.3

<400> SEQUENCE: 106

Cys Thr Leu Ser Asn Pro Pro
1               5

<210> SEQ ID NO 107
<211> LENGTH: 8
<212> TYPE: PRT
<213> ORGANISM: Artificial Sequence
<220> FEATURE:
<223> OTHER INFORMATION: derived from homo sapiens Nav1.3

<400> SEQUENCE: 107

Cys Thr Asp Asp Gln Gly Lys Tyr
1               5

<210> SEQ ID NO 108
<211> LENGTH: 10
<212> TYPE: PRT
<213> ORGANISM: Artificial Sequence
<220> FEATURE:
<223> OTHER INFORMATION: derived from homo sapiens Nav1.3

<400> SEQUENCE: 108

Cys Asp Ser Ala Phe Glu Thr Asn Thr Thr
1               5                   10
```

```
<210> SEQ ID NO 109
<211> LENGTH: 10
<212> TYPE: PRT
<213> ORGANISM: Artificial Sequence
<220> FEATURE:
<223> OTHER INFORMATION: derived from homo sapiens Nav1.3

<400> SEQUENCE: 109

Cys Thr Met Ser Thr Phe Asn Trp Lys Asp
1               5                   10

<210> SEQ ID NO 110
<211> LENGTH: 6
<212> TYPE: PRT
<213> ORGANISM: Artificial Sequence
<220> FEATURE:
<223> OTHER INFORMATION: derived from homo sapiens Nav1.3

<400> SEQUENCE: 110

Cys Lys Ile Asn Asp Asp
1               5

<210> SEQ ID NO 111
<211> LENGTH: 14
<212> TYPE: PRT
<213> ORGANISM: Artificial Sequence
<220> FEATURE:
<223> OTHER INFORMATION: derived from homo sapiens Nav1.3

<400> SEQUENCE: 111

Cys Val Asn Met Thr Thr Gly Asn Met Phe Asp Ile Ser Asp
1               5                   10

<210> SEQ ID NO 112
<211> LENGTH: 9
<212> TYPE: PRT
<213> ORGANISM: Artificial Sequence
<220> FEATURE:
<223> OTHER INFORMATION: derived from homo sapiens Nav1.3

<400> SEQUENCE: 112

Cys Gln Ala Leu Gly Lys Gln Ala Arg
1               5

<210> SEQ ID NO 113
<211> LENGTH: 8
<212> TYPE: PRT
<213> ORGANISM: Artificial Sequence
<220> FEATURE:
<223> OTHER INFORMATION: derived from homo sapiens Nav1.3

<400> SEQUENCE: 113

Cys Arg Asp Val Lys Leu Gln Pro
1               5

<210> SEQ ID NO 114
<211> LENGTH: 10
<212> TYPE: PRT
<213> ORGANISM: Artificial Sequence
<220> FEATURE:
<223> OTHER INFORMATION: derived from homo sapiens Nav1.8

<400> SEQUENCE: 114

Cys Met Thr Arg Thr Asp Leu Pro Glu Lys
1               5                   10
```

```
<210> SEQ ID NO 115
<211> LENGTH: 9
<212> TYPE: PRT
<213> ORGANISM: Artificial Sequence
<220> FEATURE:
<223> OTHER INFORMATION: derived from homo sapiens Nav1.8

<400> SEQUENCE: 115

Cys Gly Met Ser Pro Thr Phe Glu Ala
1               5

<210> SEQ ID NO 116
<211> LENGTH: 9
<212> TYPE: PRT
<213> ORGANISM: Artificial Sequence
<220> FEATURE:
<223> OTHER INFORMATION: derived from homo sapiens Nav1.8

<400> SEQUENCE: 116

Cys Pro Met Thr Asp Ala Phe Asp Ala
1               5

<210> SEQ ID NO 117
<211> LENGTH: 13
<212> TYPE: PRT
<213> ORGANISM: Artificial Sequence
<220> FEATURE:
<223> OTHER INFORMATION: derived from homo sapiens Nav1.8

<400> SEQUENCE: 117

Cys Met Glu His His Gly Met Ser Pro Thr Phe Glu Ala
1               5                   10

<210> SEQ ID NO 118
<211> LENGTH: 13
<212> TYPE: PRT
<213> ORGANISM: Artificial Sequence
<220> FEATURE:
<223> OTHER INFORMATION: derived from homo sapiens Nav1.8

<400> SEQUENCE: 118

Cys Met Glu His Tyr Pro Met Thr Asp Ala Phe Asp Ala
1               5                   10

<210> SEQ ID NO 119
<211> LENGTH: 8
<212> TYPE: PRT
<213> ORGANISM: Artificial Sequence
<220> FEATURE:
<223> OTHER INFORMATION: derived from homo sapiens Nav1.8

<400> SEQUENCE: 119

Cys Asp Gln Lys Pro Thr Val Lys
1               5

<210> SEQ ID NO 120
<211> LENGTH: 8
<212> TYPE: PRT
<213> ORGANISM: Artificial Sequence
<220> FEATURE:
<223> OTHER INFORMATION: derived from homo sapiens Nav1.8

<400> SEQUENCE: 120

Cys Glu Glu Lys Pro Arg Val Lys
1               5

<210> SEQ ID NO 121
```

```
<211> LENGTH: 8
<212> TYPE: PRT
<213> ORGANISM: Artificial Sequence
<220> FEATURE:
<223> OTHER INFORMATION: derived from homo sapiens Nav1.8

<400> SEQUENCE: 121

Cys Gln Ser Glu Glu Lys Thr Lys
1               5

<210> SEQ ID NO 122
<211> LENGTH: 8
<212> TYPE: PRT
<213> ORGANISM: Artificial Sequence
<220> FEATURE:
<223> OTHER INFORMATION: derived from homo sapiens Nav1.8

<400> SEQUENCE: 122

Cys Asp Asp Gln Ser Glu Glu Lys
1               5

<210> SEQ ID NO 123
<211> LENGTH: 8
<212> TYPE: PRT
<213> ORGANISM: Artificial Sequence
<220> FEATURE:
<223> OTHER INFORMATION: derived from homo sapiens Nav1.8

<400> SEQUENCE: 123

Cys Asp Asn Gln Ser Glu Glu Lys
1               5

<210> SEQ ID NO 124
<211> LENGTH: 10
<212> TYPE: PRT
<213> ORGANISM: Artificial Sequence
<220> FEATURE:
<223> OTHER INFORMATION: derived from homo sapiens Nav1.8

<400> SEQUENCE: 124

Cys Val Lys Asn Asp Met Ala Val Asn Lys
1               5                   10

<210> SEQ ID NO 125
<211> LENGTH: 10
<212> TYPE: PRT
<213> ORGANISM: Artificial Sequence
<220> FEATURE:
<223> OTHER INFORMATION: derived from homo sapiens Nav1.8

<400> SEQUENCE: 125

Cys Ile Lys Asn Gly Thr Asp Pro His Lys
1               5                   10

<210> SEQ ID NO 126
<211> LENGTH: 9
<212> TYPE: PRT
<213> ORGANISM: Artificial Sequence
<220> FEATURE:
<223> OTHER INFORMATION: derived from homo sapiens Nav1.8

<400> SEQUENCE: 126

Cys Thr Asn Tyr Ser Ser His Arg Lys
1               5

<210> SEQ ID NO 127
<211> LENGTH: 9
```

```
<212> TYPE: PRT
<213> ORGANISM: Artificial Sequence
<220> FEATURE:
<223> OTHER INFORMATION: derived from homo sapiens NAv1.8

<400> SEQUENCE: 127

Cys Asp Asn Leu Ser Ser Glu Met Ala
1               5

<210> SEQ ID NO 128
<211> LENGTH: 9
<212> TYPE: PRT
<213> ORGANISM: Artificial Sequence
<220> FEATURE:
<223> OTHER INFORMATION: derived from homo sapiens Nav1.8

<400> SEQUENCE: 128

Cys Ala Pro His Glu Asp Trp Pro Arg
1               5

<210> SEQ ID NO 129
<211> LENGTH: 9
<212> TYPE: PRT
<213> ORGANISM: Artificial Sequence
<220> FEATURE:
<223> OTHER INFORMATION: derived from homo sapiens Nav1.8

<400> SEQUENCE: 129

Cys Val Trp Asn Gly Glu Arg Leu Arg
1               5

<210> SEQ ID NO 130
<211> LENGTH: 10
<212> TYPE: PRT
<213> ORGANISM: Artificial Sequence
<220> FEATURE:
<223> OTHER INFORMATION: derived from homo sapiens Nav1.8

<400> SEQUENCE: 130

Cys Ile Asn Tyr Thr Asp Gly Glu Phe Ser
1               5                   10

<210> SEQ ID NO 131
<211> LENGTH: 10
<212> TYPE: PRT
<213> ORGANISM: Artificial Sequence
<220> FEATURE:
<223> OTHER INFORMATION: derived from homo sapiens Nav1.8

<400> SEQUENCE: 131

Cys Val Asp Thr Arg Ser Asn Pro Phe Ser
1               5                   10

<210> SEQ ID NO 132
<211> LENGTH: 9
<212> TYPE: PRT
<213> ORGANISM: Artificial Sequence
<220> FEATURE:
<223> OTHER INFORMATION: derived from homo sapiens Nav1.8

<400> SEQUENCE: 132

Cys Lys Ile Gln Asn Ser Thr Gly Ser
1               5

<210> SEQ ID NO 133
<211> LENGTH: 9
<212> TYPE: PRT
```

```
<213> ORGANISM: Artificial Sequence
<220> FEATURE:
<223> OTHER INFORMATION: derived from homo sapiens Nav1.8

<400> SEQUENCE: 133

Cys Tyr Asn Gln Asn Asn Thr Gly His
1               5

<210> SEQ ID NO 134
<211> LENGTH: 12
<212> TYPE: PRT
<213> ORGANISM: Artificial Sequence
<220> FEATURE:
<223> OTHER INFORMATION: derived from homo sapiens Nav1.9

<400> SEQUENCE: 134

Cys Thr Gly Pro Ala Lys Asn Ser Asn Ser Asn Asn
1               5                   10

<210> SEQ ID NO 135
<211> LENGTH: 15
<212> TYPE: PRT
<213> ORGANISM: Artificial Sequence
<220> FEATURE:
<223> OTHER INFORMATION: derived from homo sapiens Nav1.9

<400> SEQUENCE: 135

Cys Ala Thr Gly Pro Ala Lys Asn Ser Asn Ser Asn Asn Thr Asp
1               5                   10                  15

<210> SEQ ID NO 136
<211> LENGTH: 7
<212> TYPE: PRT
<213> ORGANISM: Artificial Sequence
<220> FEATURE:
<223> OTHER INFORMATION: derived from homo sapiens Nav1.9

<400> SEQUENCE: 136

Cys Glu Ala Ser Phe Glu Lys
1               5

<210> SEQ ID NO 137
<211> LENGTH: 12
<212> TYPE: PRT
<213> ORGANISM: Artificial Sequence
<220> FEATURE:
<223> OTHER INFORMATION: derived from homo sapiens Nav1.9

<400> SEQUENCE: 137

Cys Glu His His Lys Met Glu Ala Ser Phe Glu Lys
1               5                   10

<210> SEQ ID NO 138
<211> LENGTH: 9
<212> TYPE: PRT
<213> ORGANISM: Artificial Sequence
<220> FEATURE:
<223> OTHER INFORMATION: derived from homo sapiens Nav1.9

<400> SEQUENCE: 138

Cys Glu Asn Gln Pro Lys Ile Gln Glu
1               5

<210> SEQ ID NO 139
<211> LENGTH: 12
<212> TYPE: PRT
<213> ORGANISM: Artificial Sequence
```

```
<220> FEATURE:
<223> OTHER INFORMATION: derived from homo sapiens Nav1.9

<400> SEQUENCE: 139

Cys Glu Ser Tyr Asn Gln Pro Lys Ala Met Lys Ser
1               5                   10

<210> SEQ ID NO 140
<211> LENGTH: 9
<212> TYPE: PRT
<213> ORGANISM: Artificial Sequence
<220> FEATURE:
<223> OTHER INFORMATION: derived from homo sapiens Nav1.9

<400> SEQUENCE: 140

Cys Tyr Asn Gln Pro Lys Ala Met Lys
1               5

<210> SEQ ID NO 141
<211> LENGTH: 12
<212> TYPE: PRT
<213> ORGANISM: Artificial Sequence
<220> FEATURE:
<223> OTHER INFORMATION: derived from homo sapiens Nav1.9

<400> SEQUENCE: 141

Cys Lys Asn Ile Ser Asn Pro Glu Ala Tyr Asp His
1               5                   10

<210> SEQ ID NO 142
<211> LENGTH: 13
<212> TYPE: PRT
<213> ORGANISM: Artificial Sequence
<220> FEATURE:
<223> OTHER INFORMATION: derived from homo sapiens Nav1.9

<400> SEQUENCE: 142

Cys Phe Glu Lys Lys Glu Asn Ser Pro Glu Phe Lys Met
1               5                   10

<210> SEQ ID NO 143
<211> LENGTH: 9
<212> TYPE: PRT
<213> ORGANISM: Artificial Sequence
<220> FEATURE:
<223> OTHER INFORMATION: derived from homo sapiens Nav1.9

<400> SEQUENCE: 143

Cys Gly Ile Trp Met Gly Asn Ser Ala
1               5

<210> SEQ ID NO 144
<211> LENGTH: 6
<212> TYPE: PRT
<213> ORGANISM: Artificial Sequence
<220> FEATURE:
<223> OTHER INFORMATION: derived from homo sapiens Nav1.9

<400> SEQUENCE: 144

Cys Ser Ile Gln Tyr Glu
1               5

<210> SEQ ID NO 145
<211> LENGTH: 7
<212> TYPE: PRT
<213> ORGANISM: Artificial Sequence
<220> FEATURE:
```

```
<223> OTHER INFORMATION: derived from homo sapiens Nav1.9

<400> SEQUENCE: 145

Cys Lys His Thr Lys Ile Asn
1               5

<210> SEQ ID NO 146
<211> LENGTH: 9
<212> TYPE: PRT
<213> ORGANISM: Artificial Sequence
<220> FEATURE:
<223> OTHER INFORMATION: derived from homo sapiens Nav1.9

<400> SEQUENCE: 146

Cys Asn Ser Gln Lys Ser Pro Lys Leu
1               5

<210> SEQ ID NO 147
<211> LENGTH: 9
<212> TYPE: PRT
<213> ORGANISM: Artificial Sequence
<220> FEATURE:
<223> OTHER INFORMATION: derived from homo sapiens Nav1.9

<400> SEQUENCE: 147

Cys Asn Pro Thr Gly Pro Thr Val Ser
1               5

<210> SEQ ID NO 148
<211> LENGTH: 6
<212> TYPE: PRT
<213> ORGANISM: Artificial Sequence
<220> FEATURE:
<223> OTHER INFORMATION: derived from homo sapiens Nav1.9

<400> SEQUENCE: 148

Cys Ile Asn Gly Thr Asp
1               5

<210> SEQ ID NO 149
<211> LENGTH: 5
<212> TYPE: PRT
<213> ORGANISM: Artificial Sequence
<220> FEATURE:
<223> OTHER INFORMATION: derived from homo sapiens Nav1.9

<400> SEQUENCE: 149

Cys Asn Lys Ser Gln
1               5

<210> SEQ ID NO 150
<211> LENGTH: 7
<212> TYPE: PRT
<213> ORGANISM: Artificial Sequence
<220> FEATURE:
<223> OTHER INFORMATION: derived from homo sapiens Nav1.9

<400> SEQUENCE: 150

Cys Glu Ser Gly Asn Phe Ser
1               5

<210> SEQ ID NO 151
<211> LENGTH: 11
<212> TYPE: PRT
<213> ORGANISM: Artificial Sequence
<220> FEATURE:
<223> OTHER INFORMATION: derived from homo sapiens Nav1.9
```

```
<400> SEQUENCE: 151

Cys Thr Glu Lys Glu Gln Gln Pro Glu Phe Glu
1               5                   10

<210> SEQ ID NO 152
<211> LENGTH: 8
<212> TYPE: PRT
<213> ORGANISM: Artificial Sequence
<220> FEATURE:
<223> OTHER INFORMATION: derived from homo sapiens Nav1.9

<400> SEQUENCE: 152

Cys Asn Ser Ser Ser Lys Glu Ser
1               5

<210> SEQ ID NO 153
<211> LENGTH: 7
<212> TYPE: PRT
<213> ORGANISM: Artificial Sequence
<220> FEATURE:
<223> OTHER INFORMATION: derived from homo sapiens HCN1

<400> SEQUENCE: 153

Cys Thr Glu Gln Thr Thr Thr
1               5

<210> SEQ ID NO 154
<211> LENGTH: 7
<212> TYPE: PRT
<213> ORGANISM: Artificial Sequence
<220> FEATURE:
<223> OTHER INFORMATION: derived from homo sapiens HCN1

<400> SEQUENCE: 154

Cys Gln Asp Phe Pro Pro Asp
1               5

<210> SEQ ID NO 155
<211> LENGTH: 8
<212> TYPE: PRT
<213> ORGANISM: Artificial Sequence
<220> FEATURE:
<223> OTHER INFORMATION: derived from homo sapiens HCN1

<400> SEQUENCE: 155

Cys Leu Asn Glu Met Val Asn Asp
1               5

<210> SEQ ID NO 156
<211> LENGTH: 7
<212> TYPE: PRT
<213> ORGANISM: Artificial Sequence
<220> FEATURE:
<223> OTHER INFORMATION: derived from homo sapiens HCN2

<400> SEQUENCE: 156

Cys Lys Asp Glu Thr Thr Ala
1               5

<210> SEQ ID NO 157
<211> LENGTH: 7
<212> TYPE: PRT
<213> ORGANISM: Artificial Sequence
<220> FEATURE:
<223> OTHER INFORMATION: derived from homo sapiens HCN2
```

```
<400> SEQUENCE: 157

Cys Gln Asp Phe Pro Arg Asn
1               5

<210> SEQ ID NO 158
<211> LENGTH: 8
<212> TYPE: PRT
<213> ORGANISM: Artificial Sequence
<220> FEATURE:
<223> OTHER INFORMATION: derived from homo sapiens HCN2

<400> SEQUENCE: 158

Cys Ile Asn Gly Met Val Asn His
1               5

<210> SEQ ID NO 159
<211> LENGTH: 12
<212> TYPE: PRT
<213> ORGANISM: Artificial Sequence
<220> FEATURE:
<223> OTHER INFORMATION: derived from homo sapiens Nav1.1

<400> SEQUENCE: 159

Cys Glu His Tyr Pro Met Thr Asp His Phe Asn Asn
1               5                   10

<210> SEQ ID NO 160
<211> LENGTH: 12
<212> TYPE: PRT
<213> ORGANISM: Artificial Sequence
<220> FEATURE:
<223> OTHER INFORMATION: derived from homo sapiens Nav1.2 and Nav1.3

<400> SEQUENCE: 160

Cys Glu His Tyr Pro Met Thr Glu Gln Phe Ser Ser
1               5                   10

<210> SEQ ID NO 161
<211> LENGTH: 12
<212> TYPE: PRT
<213> ORGANISM: Artificial Sequence
<220> FEATURE:
<223> OTHER INFORMATION: derived from homo sapiens Nav1.4

<400> SEQUENCE: 161

Cys Glu His Tyr Pro Met Thr Glu His Phe Asp Asn
1               5                   10

<210> SEQ ID NO 162
<211> LENGTH: 12
<212> TYPE: PRT
<213> ORGANISM: Artificial Sequence
<220> FEATURE:
<223> OTHER INFORMATION: derived from homo sapiens Nav1.5

<400> SEQUENCE: 162

Cys Glu His Tyr Asn Met Thr Ser Glu Phe Glu Glu
1               5                   10

<210> SEQ ID NO 163
<211> LENGTH: 12
<212> TYPE: PRT
<213> ORGANISM: Artificial Sequence
<220> FEATURE:
<223> OTHER INFORMATION: derived from homo sapiens Nav1.6

<400> SEQUENCE: 163
```

```
Cys Glu His His Pro Met Thr Pro Gln Phe Glu His
1               5                   10
```

<210> SEQ ID NO 164
<211> LENGTH: 12
<212> TYPE: PRT
<213> ORGANISM: Artificial Sequence
<220> FEATURE:
<223> OTHER INFORMATION: derived from homo sapiens Nav.18

<400> SEQUENCE: 164

```
Cys Glu His His Gly Met Ser Pro Thr Phe Glu Ala
1               5                   10
```

<210> SEQ ID NO 165
<211> LENGTH: 12
<212> TYPE: PRT
<213> ORGANISM: Artificial Sequence
<220> FEATURE:
<223> OTHER INFORMATION: derived from homo sapiens Nav1.9

<400> SEQUENCE: 165

```
Cys Glu His His Lys Met Glu Ala Ser Phe Glu Lys
1               5                   10
```

<210> SEQ ID NO 166
<211> LENGTH: 4
<212> TYPE: PRT
<213> ORGANISM: Artificial Sequence
<220> FEATURE:
<223> OTHER INFORMATION: hinge of CTLA-4 antibody

<400> SEQUENCE: 166

```
Cys Pro Pro Cys
1
```

<210> SEQ ID NO 167
<211> LENGTH: 4
<212> TYPE: PRT
<213> ORGANISM: Artificial Sequence
<220> FEATURE:
<223> OTHER INFORMATION: hinge of IgG1-Fc

<400> SEQUENCE: 167

```
Ser Pro Pro Ser
1
```